US010167525B2

(12) United States Patent
Steinmetzer et al.

(10) Patent No.: US 10,167,525 B2
(45) Date of Patent: *Jan. 1, 2019

(54) ASSAYS

(71) Applicant: ALERE TECHNOLOGIES GMBH, Jena (DE)

(72) Inventors: Katrin Steinmetzer, Jena (DE); Eugen Ermantraut, Jena (DE); Torsten Schulz, Jena (DE); Thomas Kaiser, Hohlstedt (DE); Thomas Ullrich, Jena (DE)

(73) Assignee: ALERE TECHNOLOGIES GMBH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/499,221

(22) Filed: Sep. 28, 2014

(65) Prior Publication Data

US 2015/0197822 A1 Jul. 16, 2015

Related U.S. Application Data

(63) Continuation of application No. 12/513,597, filed as application No. PCT/EP2007/061953 on Nov. 6, 2007, now Pat. No. 8,846,313.

(60) Provisional application No. 60/856,782, filed on Nov. 6, 2006, provisional application No. 60/951,364, filed on Jul. 23, 2007.

(51) Int. Cl.
| *C12Q 1/68* | (2018.01) |
| *C12Q 1/70* | (2006.01) |
| *B01J 19/00* | (2006.01) |
| *B01L 3/00* | (2006.01) |
| *C12Q 1/6825* | (2018.01) |
| *C12Q 1/6837* | (2018.01) |
| *B01L 7/00* | (2006.01) |
| *B01L 9/00* | (2006.01) |
| *C12Q 1/6813* | (2018.01) |

(52) U.S. Cl.
CPC .......... *C12Q 1/703* (2013.01); *B01J 19/0046* (2013.01); *B01L 3/502738* (2013.01); *B01L 3/502746* (2013.01); *B01L 3/502753* (2013.01); *B01L 3/502761* (2013.01); *C12Q 1/6825* (2013.01); *C12Q 1/6837* (2013.01); *C12Q 1/701* (2013.01); *B01J 2219/0072* (2013.01); *B01J 2219/00527* (2013.01); *B01J 2219/00576* (2013.01); *B01J 2219/00605* (2013.01); *B01J 2219/00659* (2013.01); *B01J 2219/00695* (2013.01); *B01J 2219/00704* (2013.01); *B01J 2219/00722* (2013.01); *B01L 7/52* (2013.01); *B01L 9/527* (2013.01); *B01L 2200/0647* (2013.01); *B01L 2200/10* (2013.01); *B01L 2300/0636* (2013.01); *B01L 2300/0681* (2013.01); *B01L 2300/0816* (2013.01); *B01L 2400/0481* (2013.01); *B01L 2400/0487* (2013.01); *B01L 2400/0655* (2013.01); *C12Q 1/6813* (2013.01); *C12Q 2600/158* (2013.01)

(58) Field of Classification Search
CPC ... C12Q 1/68; B01J 19/00; B01L 3/50; G01N 33/48
See application file for complete search history.

(56) References Cited

U.S. PATENT DOCUMENTS

| 5,104,791 | A |   | 4/1992  | Abbott et al. |
| 5,536,648 | A |   | 7/1996  | Kemp et al. |
| 5,561,043 | A |   | 10/1996 | Cantor et al. |
| 5,580,970 | A |   | 12/1996 | Hendricks et al. |
| 5,702,896 | A | * | 12/1997 | Collins ................ C12Q 1/6813 435/6.12 |
| 6,238,866 | B1 | * | 5/2001  | Yeh ...................... C12Q 1/6837 422/68.1 |
| 6,875,619 | B2 |   | 4/2005  | Blackburn |
| 6,960,437 | B2 |   | 11/2005 | Enzelberger et al. |
| 7,323,305 | B2 |   | 1/2008  | Leamon et al. |
| 8,216,810 | B2 |   | 7/2012  | Lipkin et al. |
| 2003/0008308 | A1 |   | 1/2003 | Enzelberger et al. |
| 2003/0054376 | A1 |   | 3/2003 | Mullis et al. |
| 2003/0175947 | A1 |   | 9/2003 | Liu et al. |
| 2003/0190608 | A1 |   | 10/2003 | Blackburn |
| 2003/0190680 | A1 |   | 10/2003 | Rothschild et al. |
| 2004/0086867 | A1 | * | 5/2004 | Han ..................... C12Q 1/6816 435/6.12 |
| 2005/0130173 | A1 |   | 6/2005 | Leamon et al. |
| 2005/0239086 | A1 |   | 10/2005 | Lipkin et al. |
| 2007/0051412 | A1 |   | 3/2007 | Heath et al. |

FOREIGN PATENT DOCUMENTS

| CN | 1548957  | 11/2004 |
| EP | 1 418 243 | 5/2004 |
| EP | 1652912  | 5/2006 |

(Continued)

OTHER PUBLICATIONS

Esch et al, Detection of Cryptosporidium parvum Using Oligonucleotide-Tagged Liposomes in a Competitive Assay Format, 2001, Anal. Chem., 73, 3162-3167.*
Casper et al, Development and evaluation of a method to detect and quantify enteroviruses using NASBA and internal control RNA (IC-NASBA), 2005, Journal of Virological Methods 124, 149-155.*

*Primary Examiner* — Narayan K Bhat
(74) *Attorney, Agent, or Firm* — Casimir Jones, S.C.; David Casimir; Tanya Arenson

(57) ABSTRACT

A method includes forming a composition of matter including an amount of a reporter compound, a binding member capable of capturing the reporter compound, and an amount of a target nucleic acid capable of forming complexes with the reporter compound.

27 Claims, 36 Drawing Sheets

Specification includes a Sequence Listing.

(56) References Cited

FOREIGN PATENT DOCUMENTS

| | | | |
|---|---|---|---|
| JP | 2002527254 | | 8/2002 |
| JP | 2004257993 | | 9/2004 |
| JP | WO 2004/097048 | * | 11/2004 |
| JP | 2006197906 | | 8/2006 |
| JP | 2006217818 | | 8/2006 |
| WO | WO 1994/26414 | | 11/1994 |
| WO | WO 1997/22825 | | 6/1997 |
| WO | 00/21659 | | 4/2000 |
| WO | WO 02/31206 | * | 4/2002 |
| WO | 2006/007567 | | 1/2006 |

* cited by examiner

2. Step - Capture of RNA complexes onto solid matrix

Capture assay with 10 µl streptavidin sepharose, RNA and 10 µl whole blood test stability of lyophilized streptavidin sepharose → streptavidin sepharose can be lyophilized without significant loss of function, long term stability tests will have to be performed

5. Step - Detection

RT-PCR with streptavidin sepharose after capture assay with whole blood (negative control: with blood and capture probe, but no RNA)

- HIV RNA in presence of 10 μl blood was captured onto streptavidin sepharose
- aliquot of streptavidin sepharose (SA) with purified RNA was used as template for RT-PCR
- another aliquot of streptavidin sepharose with purified RNA was elutetd and used as template for RT-PCR
- after RT-PCR samples with SA was incubated with Cy3-probe 1...RT-PCR negativ control
2...RT-PCR positive control
3...elution negative control
4...elution positive control
5...SA negative control
6...SA positive control
7...SA negative control, no taqman probe
8...SA positive control, no taqman probe
MW...molecular weight standard RT-PCR product

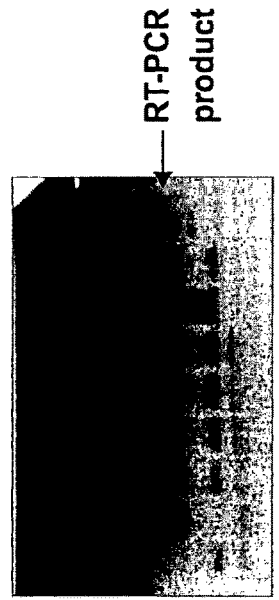

fluorescent images of SA next page.....

Fig. 15

5. Step - Detection (cont.)
negative control (#7 on gel, for description see page before)
positive control (#8 on gel, for description see page before)
→ more fluorescent beads are visible in postive control, but detection needs to be optimized (non-specific binding of fluorescent probe to SA)
Fig. 16

FIG. 24
A
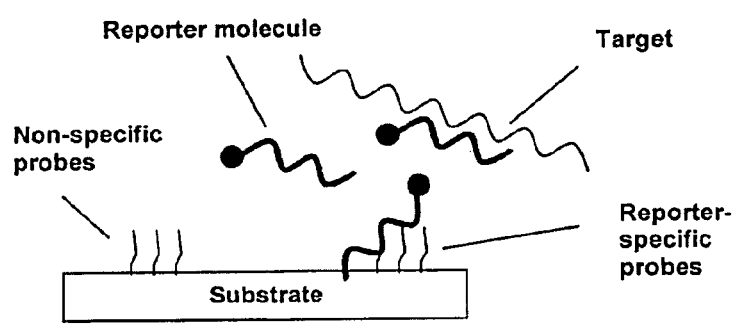
B
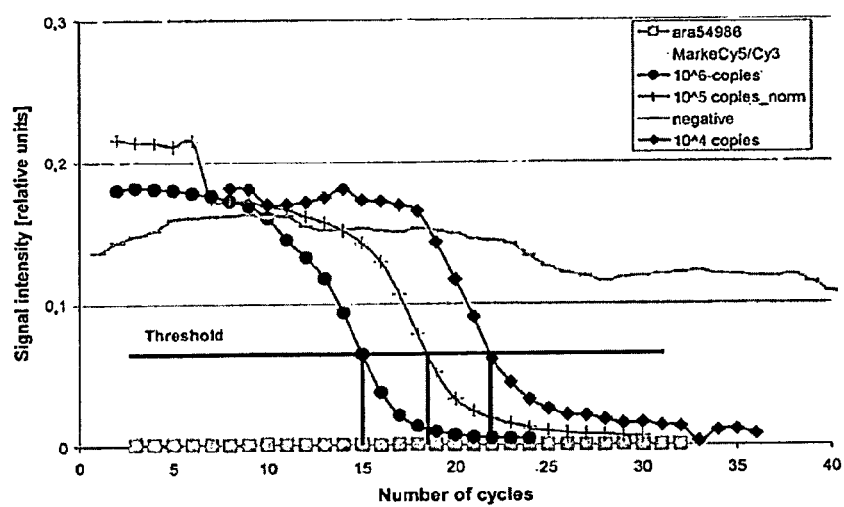
C
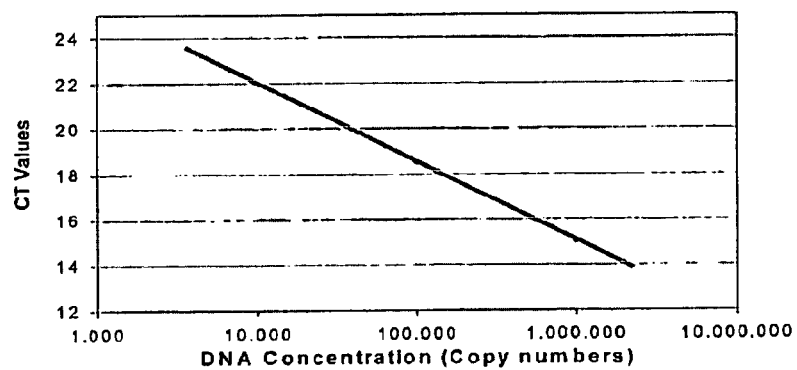

FIG. 25
A
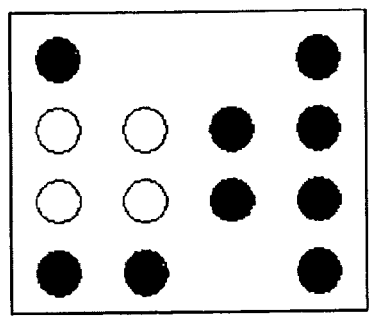
B
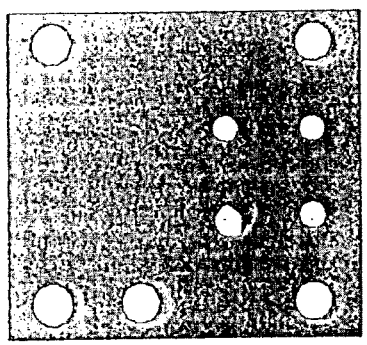
CYCLE 1
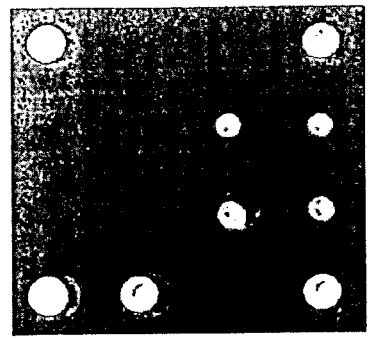
CYCLE 12
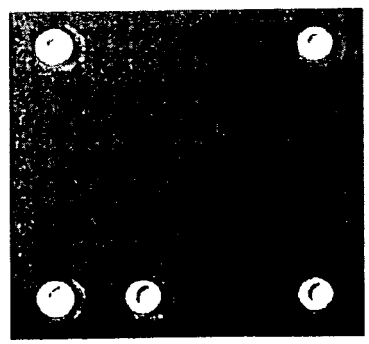
CYCLE 18
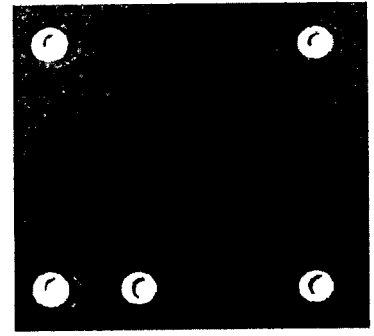
CYCLE 21

ASSAYS

PRIORITY CLAIM

This application claims priority from U.S. application Ser. No. 60/951,364, filed Jul. 23, 2007 and U.S. application Ser. No. 60/856,782, filed Nov. 6, 2006, each of which is incorporated by reference in its entirety.

FIELD OF THE INVENTION

The present invention relates to assays, for example, assays for polynucleotides.

RELATED APPLICATIONS

This application is related to the U.S. continuation of International Patent Application PCT/EP2005/004923, filed on May 6, 2005, which designates the United States and claims priority to German Patent Application DE 10 2004 022 263, filed May 6, 2004, the U.S. continuation having Ser. No. 11/593,021 entitled "Method and Device for the Detection of Molecular Interactions" and being filed Nov. 6, 2006, each of which applications is hereby incorporated by reference in its entirety.

BACKGROUND

The presence of a pathogen in a biological sample can be determined by assaying the sample for a polynucleotide associated with the presence of the pathogen. Bacteria, mold, and viruses are examples of pathogens that can be determined based on an assay for associated polynucleotides.

EP 0 637 999 discloses devices for amplifying a preselected polynucleotide in a sample by conducting a polynucleotide polymerization reaction. The devices include a substrate microfabricated to define a sample inlet port and a mesoscale flow system, which extends from the inlet port. The mesoscale flow system includes a polynucleotide polymerization reaction chamber in fluid communication with the inlet port which is provided with reagents required for polymerization and amplification of a preselected polynucleotide. The devices can be utilized to implement a polymerase chain reaction (PCR) in the reaction chamber (PCR chamber). The PCR chamber is provided with the sample polynucleotide, polymerase, nucleoside triphosphates, primers and other reagents required for the polymerase chain reaction, and the device is provided with means for thermally controlling the temperature of the contents of the reaction chamber at a temperature controlled to dehybridize double-stranded polynucleotide, to anneal the primers, and to polymerize and amplify the polynucleotide.

However, it can be difficult to properly coordinate various tasks of conventional microfluidic devices.

SUMMARY

There can be a need for a device and a method enabling sample analysis in a simple manner.

In one aspect, a device includes a rigid substrate, a flexible cover element at least partially covering the substrate, a first structure formed in the substrate, adapted for accommodating liquids and adapted for releasing contents of one or more cells, spores, or viruses, the contents including the target molecules (for instance a dried buffer in the structure or chamber or well), a second structure (which can differ from the first structure) formed in the substrate, adapted for accommodating liquids and including at least one binding member adapted for capturing the target molecules and for determining a value indicative of the presence and/or amount of the target molecules, a microfluidic network interconnecting at least the first structure and the second structure, and an actuator member adapted for effecting a fluid flow between the first structure and the second structure by pressing the flexible cover element against the substrate to selectively close a portion of the microfluidic network.

In another aspect, a device includes a structure adapted for accommodating liquids, wherein the structure includes at least one binding member and is in fluid communication with a microfluidic network, and a control unit adapted for controlling a fluid flow through the microfluidic network in such a manner that target molecules are captured at the at least one binding member, adapted for controlling an amplification of the target molecules in the structure, and adapted for controlling detection of compounds indicative of the presence and/or amount of the target molecules and captured at the at least one binding member.

In another aspect, a method includes accommodating liquids in a structure including at least one binding member and being in fluid communication with a microfluidic network, controlling a fluid flow through the microfluidic network in such a manner that target molecules are captured at the at least one binding member, amplifying the target molecules in the structure, and detecting compounds indicative of the presence and/or amount of the target molecules and captured at the at least one binding member.

In another aspect, a device includes a structure adapted for accommodating liquids, wherein the structure includes a first binding member adapted for capturing a first compound and includes a second binding member (which can differ from the first binding member) adapted for capturing a second compound (which can differ from the first compound) indicative of the presence and/or amount of the first compound.

In another aspect, a device can be provided in which a sample is guided, under the control of a control unit, through a microfluidic device in such a manner as to perform a predefined analysis task. In the device, a central well/central structure (which can also be denoted as second well or second structure) can be provided which can perform several or all solid phase coupling procedures needed during the analysis. In the structure (which can be denoted as a central well), it can be possible to capture target molecules of a sample (for purification or separation purposes), to amplify target molecules (for instance by polymerase chain reaction, PCR), and to perform a (for instance optical) detection procedure which allows to derive information regarding the presence/absence or even the quantity of target molecules.

Therefore, a powerful and fully automatic biochemical analysis system can be provided, which can allow deriving, in a fast and accurate manner and without the requirement of much manpower, a biochemical or medical result. For instance, with such a device, it can be possible to detect nucleic acids associated with an HIV infection in a whole blood sample of a patient, in a qualitative or in a quantitative manner.

Next, further exemplary embodiments of the devices and methods will be explained. The compounds being detected in the central well can be the target molecules. For this purpose, the central well can be provided with specific binding members (for instance binding members which differ from other binding members needed for capturing the target molecules). The target molecules can be bound to the binding members. Target molecules can be, for example, nucleic acids originating from free and from cell-associated viruses such as HIV including RNA originating from free viruses, RNA originating from cell-associated viruses, pro-viral DNA, reverse transcribed viral DNA (i.e., the "intermediates" of viral replication), and transcripts derived from pro-viral DNA (i.e., RNA molecules obtained by transcription of the host DNA genome).

Alternatively, specific compounds can be provided such as reporter compounds which can bind, for instance, to a PCR product, to RNA or to DNA. In such a scenario, the reporter compounds can be the compounds which are detected, thereby allowing to indirectly derive information regarding the presence and/or amount of target molecules in a sample.

The at least one binding member can be adapted for capturing the target molecules. For example, the at least one binding member can include labelled beads capable of capturing complexes including target molecules such as total viral nucleic acids.

The at least one binding member can be adapted for capturing compounds indicative of the presence and/or amount of the target molecules. Thus, not only the separate individual target molecules can be detected directly, but it is also possible to detect target molecules indirectly, for instance by detecting reporter compounds captured on a binding member.

The at least one binding member can include a first binding member adapted for capturing the target molecules and can include a second binding member (which can differ from the first binding member) adapted for capturing reporter compounds indicative of the presence and/or amount of the target molecules. Therefore, two different kinds of compounds can be provided, one specifically for capturing the target molecules after lysing, e.g., capture molecules including a binding portion specific to a region of a target polynucleotide and an anchor group; the other one for detection purposes, e.g., reporter compounds capable of forming complexes with the target polynucleotide, where the formation of complexes with the target polynucleotide inhibits capture of the reporter compound by the second binding member. In other words, capture can be functionally decoupled from detection. For example, the first binding member can be beads being configured to bind complexes including a capture molecule and a target molecule, e.g., by binding an anchor group of the capture molecule, whereas the second binding member can be a surface of the central well capable of capturing reporter compounds. The surface of the central well being the second binding member can include one or more different reporter specific capture molecules each capable of capturing a reporter compound on the surface.

The structure, i.e., the central member at which the various solid phase coupling procedures occur, can be a well. A "well" can be an indentation or a recess formed in a substrate and providing a sample chamber in which various analysis procedures can be performed. Such a well can be a cylindrical structure or pot having a volume on the order of microliters to milliliters.

The microfluidic network can include a channel or a plurality of interconnected channels. A "channel" can denote a fluidic structure (for instance an essentially one-dimensional structure) having a length which is significantly larger than a width and a height, thereby providing a path along which liquids can be transported. A single channel can be provided, or several channels can be interconnected to form a channel system. Such a channel system can allow a liquid flow from one channel to another channel at bifurcations of such a system. One or more wells can be integrated in such a channel system.

In addition to a structure as described above, e.g., the "central" structure, the microfluidic network can include at least one further structure. In other words, apart from the channels and the central well, further microfluidic members can be provided, such as further channels and/or further wells. Therefore, a complex system of wells and channels can be provided.

At least one further structure (such as a lysis structure or a lysis well) can be adapted for releasing contents of one or more cells, spores, or viruses, the contents including the target molecules. Thus, such a further structure can be denoted as a lysis chamber in which biological compounds such as cells are forced to release their contents for subsequent analysis. A lysis chamber can include a structure including biochemical agents performing such tasks for releasing the contents, thereby providing a modified sample to be transported to the central well. To this end, the lysis chamber can include a lysing reagent, for example chaotropic salts or a reagent including one or more detergents which disintegrate the cellular membranes and/or viral capsids. Alternatively or in addition, the further structure, e.g., the lysis chamber, can be adapted to heat the sample in order to destroy cellular membranes and/or viral capsids (e.g., by employing or including a temperature control unit and/or temperature regulating unit as described below).

The at least one further structure can also include capture probes capable of forming complexes with the target molecules. Therefore, it can be possible to lyse a sample in the presence of capture molecules with anchor groups.

At least one further structure (such as a well including PCR reagents) can include at least one substance promoting amplification of the target molecules. In other words, a further well can be provided which includes biochemical agents needed for promoting the amplification. Although PCR agents can be included in the further structure, the actual PCR amplification procedure can be carried out at another position, such as in the central well. As will be explained below in more detail, it can be advantageous in some circumstances to transport the sample from the central well through the well including the amplification substances well back to the central well again to avoid loss of sample material. Substances promoting amplification can be substances needed for PCR (such as enzyme, primer, buffer, etc.) and are described in detail below.

The at least one further structure can also be a well. Therefore, a plurality of wells connected by the microfluidic network can be provided. However, it can also be possible to perform lysing and/or to provide amplification material in other structures than wells, for instance in channels.

The device can include a substrate, on and/or in which the structure(s) can be formed. Therefore, fluid accommodating components of the device can be monolithically integrated in the substrate. Alternatively, structure(s) can be formed on a substrate, for instance printed or spotted. Examples for materials of a rigid substrate which can properly cooperate with a flexible cover element are polycarbonate, polypropylene, polystyrene, PET, PMMA, polyethylene, acrylic glass, PU, PEEK, PVC, glass, and the like.

Particularly, the substrate can be rigid allowing it to cooperate with a flexible cover element at least partially covering the substrate in a very efficient manner. Particularly, the flexible cover element can cover the rigid substrate, and an actuator can press the cover element against the substrate to selectively close channels (for performing valve functions or the like).

According to an exemplary embodiment, the substrate can have a first surface and a second surface opposing the first surface. The structure can be provided on and/or in the first surface (particularly a first main surface) of the substrate. A further structure can be provided on and/or in the second surface (particularly a second main surface) of the substrate. A fluidic connection structure can be provided, particularly a through hole penetrating the substrate and/or a groove in a surface portion of the substrate connecting the first surface with the second surface. Such a fluidic connection structure can be arranged between the first and the second surface and can be configured to provide a fluid communication of the structure with the further structure. In such an embodiment, the substrate can be processed at two opposing main surfaces to thereby form microfluidic structures. These structures can be connected by the connection structure which can include channels formed along a surface of the substrate, or directly going through the substrate. Therefore, a device can be provided in which both main surface portions of the substrate can be used in a very efficient manner, since both main surfaces of such a substrate can be processed for providing liquid transport tasks. Optionally, such a substrate can be covered on one or both sides with a (particularly flexible) cover element, thereby allowing to control fluid flow through fluidic structures on both surfaces efficiently, for instance by actuators acting on flexible portions on one or both main surfaces. Thus, a central substrate can be provided having fluidic structures on both sides. Particularly, this can allow manufacturing a cartridge formed by three layers, namely the substrate and two at least partially flexible cover elements. Such a three layer structure can have a (for instance flexible) base element and a (for instance flexible) cover element sandwiching an intermediate layer (for instance being rigid) accommodating the microfluidic structures. Base element and/or cover element can cover the central substrate entirely or only partially, for instance at positions at which a cover function is desired as a basis for an actuator based control (see, for instance, FIG. 21).

In addition to the substrate, the device can include at least one further substrate, wherein a further structure can be provided on and/or in the further substrate. The substrate and the further substrate can be adapted to be connectable or mountable or assemblable or installable reversibly or detachably to one another in such a manner that the structure and the further structure can be brought in fluid communication in an operation state in which the substrate is connected or mounted or assembled or installed with the further substrate. In such an embodiment, a modular construction can be provided in which a device can be formed by combining several modules which can be flexibly connected to one another. A corresponding cartridge can be formed by a modular construction set, wherein each of the modules can have the following properties and can be used in combination with other cooperatively formed modules:

- it includes a chamber having at least two fluid connections;
- the chamber includes a rigid component and an elastic component;
- at least one fluid connection can be closable by the motion of the elastic component, and a mixing of the content of the chamber can be effected.

The at least one binding member can be adapted such that a plurality of solid phase coupling procedures during an analysis of the target molecules occur at the at least one binding member. The term "solid phase coupling procedure" can particularly include any kind of anchoring and hybridization, etc., at a functionalization/binding member. In this context, the "binding member or support member" can include any substance, surface or functionalization being configured to bind an anchor group of capture molecules and/or a surface being configured to capture polynucleotides. Solid phase coupling procedures can include any procedure in which molecules to be analyzed or detected are specifically bound to a solid surface, that is to say, are bound not in a solution but on a solid surface.

The at least one binding member can be adapted such that all solid phase coupling procedures during an analysis of the target molecules occur at the at least one binding member. In other words, in such an embodiment, no solid phase coupling procedures occur at another well than at the central well/structure. This can allow performing all solid phase coupling procedures in a single well, allowing for a miniature and high performance device. The at least one binding member can be adapted such that exactly two solid phase coupling procedures during an analysis of the target molecules occur at the at least one binding member. These two solid phase coupling procedures can relate to capturing target molecules from a multi-component sample, and to detecting compounds indicative of the presence or absence or the quantity of the target molecules. In the described embodiment, these two procedures are performed in a single well allowing to synergistically use provisions of the well for both such tasks. Combining such two tasks in one well can keep liquid flow paths short, keep the device small, and keep the analysis time short.

In some embodiments, the at least one binding member can be adapted such that exactly three solid phase coupling procedures during an analysis of the target molecules occur at the at least one binding member. These three solid phase coupling procedures can relate to capturing target molecules from a multi-component sample, capturing nucleic acids resulting from reverse transcription of target nucleic acids, and to detecting compounds indicative of the presence or absence or the quantity of the target molecules. In the described embodiment, these three procedures are performed in a single well allowing to synergistically use provisions of the well for all such tasks. Combining such three tasks in one well can keep liquid flow paths short, keep the device small, and keep the analysis time short.

Alternatively, the at least one binding member can be adapted such that exactly one solid phase coupling procedure during an analysis of the target molecules in the sample occurs at the at least one binding member. Such an embodiment can be particularly advantageous, when the entire biochemical analysis or experiment only includes a single solid phase coupling procedure, for instance is only foreseen for sample purification, not for detection.

At least a portion of the device located adjacent to the at least one binding member can be transparent for electromagnetic radiation in a range of wavelengths between about 1 nm and about 10 μm to thereby allow for an electromagnetic radiation based detection of the compounds indicative of the presence and/or amount of the target molecules and captured at the at least one binding member. In such embodiments, particularly a portion of the substrate close to the central well can be transparent for electromagnetic radiation used for detection purposes, particularly for electromagnetic radiation in the near-infrared, optical and/or ultraviolet wavelengths. Thus it can be possible to perform the detection on the basis of electromagnetic radiation (for instance a fluorescence-based detection) in the central well. When the portion of the device located adjacent to the at least one binding member is transparent for electromagnetic radiation in a range of wavelengths between about 400 nm and about 800 nm, an optical detection of the compounds is enabled.

The device can include or can be connectable with a temperature manipulation unit adapted for manipulating a temperature of liquids located in the structure. Such a temperature manipulation unit can include a heating and/or cooling element which allows to bring a sample to a specific temperature, or to conduct a specific temperature pattern or sequence.

The temperature manipulation unit can be adapted for manipulating a temperature of liquids located in the structure in accordance with a temperature sequence for performing a polymerase chain reaction (PCR). Such a polymerase chain reaction can require temperature cycles to, for instance about 95° C., about 55° C. and about 72° C. This sequence can be performed for specific predefined time intervals, and can be repeated a predefined number of cycles.

The at least one binding member can be configured to bind an anchor group of a capture molecule. Particularly, the at one least binding member can be configured to capture polynucleotides.

The at least one binding member can include at least one of the group consisting of capture molecules (e.g., reporter specific capture molecules, arranged on a surface of the structure (for instance immobilized in the well)), capture molecules arranged on particles (for instance on beads), capture molecules arranged on a porous surface of the structure (for instance a porous glass structure), and one or more different capture molecules (e.g., reporter specific capture molecules, arranged on different locations with respect to a surface of the structure (for instance different kinds of capture molecules being immobilized in an array-like manner in the well, for instance in the context of a competitive assay)). In some embodiments, the at least one binding member also can include capture molecules for capturing an anchor group such as biotin.

The structure can have a volume in a range between about 1 μL and about 1 mL, particularly in a range between about 20 μL and about 300 μL. For example, a well having a volume of about 100 μL can be provided.

The substrate can have a groove configured to receive a cannula for supplying liquids to the device. In such an embodiment, it can be very easy for a user to handle the device, since the cannula for sample supply simply has to be placed in the groove to be brought in proper accordance and cooperation with the microfluidic channel system, thereby allowing for an easy analysis which can be performed even by users who are not specifically skilled or trained.

The substrate can have a window portion adjacent the structure and being transparent for electromagnetic radiation in a range of wavelengths between about 1 nm and about 10 μm (that is to say for near infrared, optical or ultraviolet radiation), particularly in a range of wavelengths between essentially 400 nm and essentially 800 nm (that is to say particularly for optical radiation), to thereby allow for an electromagnetic radiation based detection of a meniscus of a liquid flowing through (more precisely reaching) the structure or the microfluidic network. In such an embodiment, an optically transparent window portion of the substrate can be detected by a radiation detector. When a meniscus of a fluid pumped through the microfluidic network or the structure passes the window portion, the transmission properties through the window portion can change abruptly in a characteristic manner, thereby generating a signal at a radiation detector indicating that the meniscus has reached a specific location in the device. This signal can be useful for triggering purposes, or as a control signal for actuators, because the cooperative motion of actuators and/or the control of temperature manipulation units can be brought in proper accordance with the present position of a sample being pumped through the device. For instance, by taking such a measure, it can be detected that a predefined volume of water or buffer has been pumped into the device, when an overflow occurs.

At least one of the group consisting of the structure and the further structure can include two fluid openings. Such fluid openings can be a fluid inlet and a fluid outlet.

The cover element can be a flexible cover element. Particularly in cooperation with a rigid substrate, the cover element and the substrate can form three-dimensionally sealed channels which can be properly controlled by actuators acting on the cover element. When the cover element is at least partially deformable at a specific position under the influence of an external force, it can be possible to selectively enable or disable a flow of liquids by opening or closing the structure or the microfluidic network. Beyond this, a transport of liquids along the structure is possible with such a cover element.

Particularly when an actuator member is provided and adapted for being actuated to deform the cover element, a high performance lab-on-chip can be provided which has integrated mixing, pumping and/or valve functions.

Any one of the structures can include one or more substances which are biologically, biochemically and/or chemically active. Therefore, when such substances, which can include capture molecules, reporter-specific capture molecules, detectable markers, lysing reagents and PCR reagents, are present in the wells in dried form, particularly in lyophilized form, it is possible to provide a device which a user simply has to fill with liquids (such as water, buffers and sample) to perform a fully automatic analysis. When the necessary biochemical components are provided in the different wells, a user can simply start an experiment on the basis of a sequence stored in the control unit and can provide water or buffers to different inlet chambers. The remainder will be performed by the fully automatic device.

The channel can have a width (that is a dimension in a surface plane of the substrate and perpendicular to a fluid flow direction) in a range between about 50 μm and about 1 mm, particularly in a range between about 100 μm and about 300 μm. For example, a width of the channel can be about 200 μm. A height (that is a dimension in a direction perpendicular to a surface plane of the substrate and perpendicular to a fluid flow direction) of the channel can be in a range between about 20 μm and about 300 μm, particularly in a range between about 50 μm and about 200 μm. For example, a height of the channel can be about 100 μm. In contrast to this, a length of the channel can be much larger than the width and the height, for instance can be larger than 1 mm, particularly can be larger than 1 cm or can even be several centimeters.

The structure can include a material adapted as a transport medium for liquids. For example, the material can include at least one of the group consisting of a solid material, a gel material, a liquid material, and a combination thereof. Therefore, the structure can be a recess or can be formed by material serving as a carrier for the liquids.

The cover element can include a flexible membrane or a flexible sealing. Such a flexible membrane or flexible sealing can be made of materials such as latex, thereby enabling the cover element to be flexibly deformed under the influence of a mechanical force (for instance generated by an actuator member).

The device can include an actuator member adapted for being actuated for deforming the cover element to thereby control a fluid flow property of liquids in the structure and/or in the microfluidic network. Such an actuator member can be under the control of the control unit and can have a plurality of cooperating pins or stencils acting on the flexible cover element to thereby selectively open or close channels, temporarily reduce the volume of a channel or well for pumping or mixing purposes, etc.

The actuator member can particularly be adapted for controlling a fluid flow property of liquids along a straight portion of a channel. When a fluid flows along a straight channel, a perpendicularly arranged actuator member can efficiently disable a fluid flow when this channel is closed at a specific portion.

The actuator member can be adapted for functioning as a valve, as a fluid mixer, and/or as a fluid pump.

More particularly, the actuator member can include a plurality of actuator elements adapted for being cooperatively actuated for deforming the cover element to thereby control the fluid flow property of liquids in accordance with a fluid flow scheme defined by the control unit. Therefore, when a user has selected a specific experiment or assay, which involves the transport of fluids and samples through various channels, the control unit simply controls the individual stencils of the actuator member to provide such a reversible compression of the flexible cover element, to thereby fully automatically perform the assay.

The control unit can be adapted to control the actuator member to deform the cover element in such a manner that target molecules are captured at the at least one binding member, that the target molecules are amplified in the structure, and that compounds indicative of the presence and/or amount of the target molecules and captured at the at least one binding member are detected. Thus, the control unit can be the central regulator of the device harmonizing the function of the various components.

The actuator member can include one or more pins configured to be reciprocated, e.g., moved alternately in forward and backward directions. By moving a pin in a forward direction, a channel can be closed by pressing the flexible cover element towards the substrate in this channel. When the pin is moved backwardly, the channel can be opened again to allow for a fluid flow. In some embodiments, the one or more pins can have an at least partially elastic tip.

The actuator member can further be provided to be movable in a direction perpendicular to a main surface of the substrate. By reciprocating in a direction which is perpendicular to the planar substrate, an efficient opening and closing can be made possible. Particularly, the actuator member can be provided movably to selectively close at least a part of the structure to disable a transport of liquids through the structure. In another operation mode, the actuator member can be moved to selectively open at least a part of the structure to enable a transport of liquids through the structure.

The actuator member can be adapted for reciprocating perpendicular to a main surface of the substrate for selectively enabling or disabling a fluid flow of liquids through the structure. The use of reciprocating actuators can allow for reversibly and selectively enabling or disabling fluid flows, allowing for a very flexible operation of the device and allowing for using the device multiple times (in contrast to approaches in which channels are closed irreversibly for performing a one-way valve function).

The actuator member can be adapted for reciprocating in a perpendicular direction to a main surface of the substrate for pumping liquids through the structure. Therefore, it is possible that the actuator member controls a volume or height of the structure. The actuator member can also selectively close the structure. Closing a structure can be performed in the context of a valve function, of a mixing function or of a pumping function. However, it is also possible to use such an actuator during a detection phase, since it is possible to compress the structure and/or binding members for detection purposes to increase the local concentration of target molecules to be detected and/or to remove background signals. This can allow increasing the accuracy.

A drive unit can be provided for mechanically driving the actuator member, wherein the drive unit can be controllable by the control unit. Such a drive unit can include a pneumatic drive mechanism, a hydraulic drive mechanism, or an electromagnetic drive mechanism.

The at least one binding member can include a three-dimensional medium, for instance particles, beads or a porous matrix. The three-dimensional medium can be arranged and configured to be reversibly compressible by moving the actuator member. By taking this measure, a very accurate detection can be made possible, because the local concentration of the molecules to be detected can be selectively increased by compressing the three-dimensional medium (such as beads) having attached thereto compounds or complexes indicative of the presence or the quantity of the target molecules.

The device can be adapted as a biosensor assay device, a microfluidic cartridge, or a lab-on-chip. Therefore, on a small scale, various biochemical functions can be combined to perform an entire biochemical experiment.

A temperature sensor can be provided and adapted for sensing a temperature of liquids transported through the device. The temperature sensor can be integrated in a substrate to thereby sense the temperature of the liquids flowing through the microfluidic network. Alternatively, the temperature sensor can be arranged at the actuator member, for instance at a tip of a stencil-like actuator, so that the actuator, when pressing the cover element against the substrate, can simultaneously measure the local temperature of the fluid.

The device can include a temperature manipulation unit adapted for manipulating a temperature of liquids, and preferably arranged at the actuator member. Such a temperature manipulation unit can also be integrated within the substrate, for example in the form of heating wires integrated in the substrate and heating sample in the well. Alternatively, such a temperature manipulation unit can be an external device such as an external electromagnetic radiation source wherein electromagnetic radiation (for instance from a laser) can be directed onto a well resulting in a heating of the fluid in the well using the electromagnetic radiation as an energy source. Further alternatively, the temperature manipulation unit can include not or not only a heating element, but also a cooling element. For such an embodiment, a Peltier cooler can be implemented with low effort.

A temperature manipulation unit can be provided and adapted for manipulating a temperature of liquids, wherein the temperature manipulation unit can include a first heating element and a second heating element, the structure being arranged between the first heating element and the second heating element. By providing two such heating plates, one being a continuous plate and the other one being an annular plate, a heating can be performed without disabling the device to be operated with an electromagnetic radiation based detector, since a recess in the annular plate can allow electromagnetic radiation to be directed onto the central well and can allow fluorescence radiation to be detected through the recess and the second heating element.

A temperature regulation unit can be provided and adapted for regulating a temperature of liquids in the structure. Such a regulation entity can include the measurement of the actual temperature and, on the basis of this measurement, the performance of a heating and/or cooling performance to thereby adjust the temperature to a desired value.

A detection unit can be provided and adapted for detecting, in the structure, compounds indicative of the presence and/or amount of the target molecules and captured at the at least one binding member. Such a detection unit can include an optical detection unit, particularly a fluorescence detection unit.

The substrate and the cover element can be separate components which are connected to one another. Alternatively, the substrate and the cover element can be made of different materials.

A transport unit can be provided and adapted for transporting liquids through the structure and/or the microfluidic network. Such a transport unit can include a pump, particularly one of the group consisting of a compressed-air pump, a hydraulic pump, a peristaltic pump, and a vacuum pump. Furthermore, the device can be adapted in such a manner, during normal use, the gravitational force promotes the flow of liquids through the device in a desired manner. Therefore, in the absence of the activity of a transport unit, liquids can directly flow in a desired direction. However, when the transport unit is switched on, the influence of the transport unit can be larger than the influence of the gravitation, thereby allowing to selectively initiate a fluid flow in a direction against the gravitational force. Therefore the combination of gravity and a special transport unit can be highly advantageous and can allow for an energy-saving operation.

The transport unit can be adapted for transporting liquids by actuating a gas bubble in the structure and/or in the microfluidic network. By moving a gas bubble through the device, the transport of the liquids through the device can be supported or promoted.

At least one filter, particularly at least one frit, can be arranged at the structure (that is to say at an inlet and/or at an outlet of the central well) and can be adapted for preventing the at least one binding member (for instance beads) arranged in the structure, from being washed out of the structure. Under the influence of a fluid flow, a mechanical force can act on the beads or other binding members in the structure. However, when a frit, that is to say a porous filter element which can be made of a sinter material, is provided at an inlet and/or an outlet of the structure it can be securely prevented that the beads are washed out of the central chamber. The frit can be provided with an annular shape to allow for being inserted into a correspondingly shaped annular groove in the device.

The at least one binding member can include a surface functionalization. The term "surface functionalization" can denote the fact that the surface is processed in such a manner as to perform a specific binding function. In such an embodiment, the binding member can be part of or coupled to or attached to the surface of the well.

The substrate and the cover element can be in direct contact to one another. Alternatively, the substrate can be free of a direct contact with the cover element. Various geometrical realizations are possible.

A portion of the substrate located adjacent to the structure can be transparent for electromagnetic radiation in a range of wavelengths between about 400 nm and about 800 nm to thereby allow for an optical detection in the structure. Therefore, visible light can be used for detection purposes. Such a detection can be performed on the basis of light absorption, light reflection, or fluorescence generation, for instance using fluorescence labels attached to molecules or complexes to be detected.

The at least one binding member can be adapted such that at least two solid phase coupling procedures during an analysis of the target molecules occur at exactly one of the at least one binding member. In other words, one and the same binding member can be used for multiple solid phase coupling procedures. For example, beads with attached groups can be used for capturing target molecules out of the sample, and can be used later for capturing compounds such as amplified and labelled target molecules as a basis for a subsequent detection.

Alternatively, the at least one binding member can be adapted such that at least two solid phase coupling procedures during an analysis of the target molecules occur at different ones of the at least one binding member. In such a configuration, for example, capturing molecules from a sample on the one hand, and detecting components indicative of the target molecules on the other hand are captured using two different kinds of binding members. For example, beads can be provided for capturing the target molecules out of a sample. On the other hand, capture molecules, e.g., reporter specific capture molecules immobilized in the well can be used in the context of a competitive assay for capturing the components indicative of the presence or amount of target molecules in the sample, e.g., reporter compounds.

In another aspect, a method includes forming complexes, each including a target nucleic acid and a capture molecule, wherein each capture molecule includes a binding portion specific to a region of the target nucleic acid and an anchor group; contacting the complexes with a binding member, the binding member being configured to bind the anchor group of the capture molecule to bind the complexes to the binding member; subjecting one or more target nucleic acids to a amplification; capturing the amplified target nucleic acids with respect to the binding member; and determining a value indicative of the presence and/or amount of the captured target nucleic acids.

The one or more target nucleic acids can be single-stranded or double-stranded nucleic acids.

The method can further including subjecting the target nucleic acids to reverse transcription prior to subjecting one or more target nucleic acids to amplification.

The method can further include releasing the captured amplified target nucleic acids from the binding member and repeating the steps of subjecting one or more target nucleic acids to amplification and capturing the amplified target nucleic acid with respect to the binding member. In such an embodiment, the cycle of releasing the captured amplified target nucleic acids from the binding member and repeating the steps of subjecting one or more target nucleic acids to amplification and capturing the amplified target nucleic acids with respect to the binding member can be performed at least 10 times or at least 20 times.

A value indicative of the presence and/or amount of the captured target nucleic acids can be determined after at least one cycle, e.g., after each cycle, of releasing the captured amplified target nucleic acids from the binding member and repeating the steps of subjecting one or more target nucleic acids to amplification and capturing the amplified target nucleic acids with respect to the binding member.

The binding member can include one or more capture molecules capable of capturing the target nucleic acids. In such an embodiment, the target nucleic acids are captured with respect to the binding member by the one or more capture molecules. The binding member can further include particles.

The step of forming complexes each including a target nucleic acid and a capture molecule can be performed spatially separated from the step of contacting the complexes with a binding member.

The method can further include labeling the target nucleic acids. The target nucleic acids can be labelled by adding or more detectable markers, e.g., prior to or during subjecting one or more target nucleic acids to amplification and/or prior to capturing the amplified target nucleic acids with respect to the binding member. The one or more detectable markers can be fluorescent markers.

Determining a value indicative of the presence and/or amount of the captured target nucleic acids can include time-dependent monitoring of the one or more indicative values obtained.

The method can further include providing the one or more target nucleic acids prior to forming complexes each including a target nucleic acid and a capture molecule. The step of providing one or more target nucleic acids can include releasing the target nucleic acids from biological material. In such an embodiment, the biological material can be selected from the group consisting of one or more prokaryotic cells, one or more eukaryotic cells, one or more erythrocytes, and one or more viral particles as well as mixtures thereof. Further, releasing the target nucleic acids from biological material can include contacting the biological material with a lysing reagent.

Providing the one or more target nucleic acids can include providing a sample including the one or more target nucleic acids wherein the sample can be selected from the group consisting of whole blood, plasma, serum, urine, sputum, saliva and cerebrospinal fluid.

Providing the one or more target nucleic acids can be performed spatially separated from the steps of contacting complexes each including a target nucleic acid and a capture molecule, subjecting the one or more target nucleic acids to amplification, capturing the amplified target nucleic acids with respect to the binding member and determining a value indicative of the presence and/or amount of the captured target nucleic acids.

The method can further include separating the one or more target nucleic acids from concomitant material.

In a further embodiment, the method according to this exemplary embodiment is performed in a device as described above. For example, the method can be performed in a device, including a rigid substrate; a flexible cover element at least partially covering the substrate; a first structure formed in the substrate, adapted for accommodating liquids and adapted for releasing contents of one or more cells, spores, or viruses, the contents including target molecules such as target nucleic acids; a second structure formed in the substrate, adapted for accommodating liquids and including at least one binding member adapted for capturing the target molecules and for determining a value indicative of the presence and/or amount of the target molecules; a microfluidic network interconnecting at least the first structure and the second structure; and an actuator unit adapted for effecting a fluid flow between the first structure and the second structure by pressing the flexible cover element against the substrate to selectively close a portion of the microfluidic network. Further, the method can be performed in a device, including a structure adapted for accommodating liquids, wherein the structure includes at least one binding member and is in fluid communication with a microfluidic network; and a control unit adapted for controlling a fluid flow through the microfluidic network in such a manner that target molecules such as target nucleic acids are captured at the at least one binding member, adapted for controlling an amplification of the target molecules in the structure, and adapted for controlling detection of compounds captured at the at least one binding member.

The device can include a first structure adapted for accommodating liquids. In such an embodiment, the complexes each include a target nucleic acid and a capture molecule are formed in the first structure.

Further, the device can include a second structure configured for detecting one or more target nucleic acids and including a cover element covering the second well and an actuator unit adapted for being actuated to deform the cover element. In such an embodiment, determining a value indicative of the presence and/or amount of the captured target nucleic acids can be performed in the second structure.

Further, subjecting one or more target nucleic acids to amplification and/or capturing the amplified target nucleic acids with respect to a binding member can also be performed in the second structure.

Determining a value indicative of the presence and/or amount of the captured target nucleic acids can be performed with the actuator actuated to deform the cover element. The cover element can be deformed in such a way that the volume of the detection well is reduced. In such an embodiment, the volume of the second well can be re-increased after determining a value indicative of the presence and/or amount of the captured target nucleic acids.

According to another exemplary embodiment of the invention, a method is provided, including: providing an amount of a reporter compound; a first binding member being configured to bind an anchor group of a capture molecule; a second binding member capable of capturing the reporter compound; an amount of a target nucleic acid capable of forming complexes with the reporter compound; the forming of complexes with a reporter compound inhibiting capturing of the reporter compound by the second binding member; and amount of capture molecules wherein each capture molecule includes a binding portion specific to a region of the target nucleic acids and an anchor group; forming complexes each including a target nucleic acid and a capture molecule; contacting the complexes with the first binding member to bind the complexes to the first binding member; releasing at least a subset of the amount of target nucleic acid from the first binding member; forming complexes of a subset of the amount of a reporter compound with at least a subset of the amount of target nucleic acid; capturing a remaining subset of the amount of reporter compound not in complex with a target nucleic acid on the second binding member; and determining a value indicative of the presence and/or amount of reporter compound captured on the second binding member.

The reporter compound can include one or more detectable labels. The one or more detectable labels can be fluorescent labels. Further, the reporter compounds can be oligonucleotides.

The method can further include determining a value indicative of the presence and/or amount of target nucleic acid based on the value indicative of the presence and/or amount of reporter compound captured on the second binding member.

The method can further include releasing the remaining subset of the amount of reporter compound from the second binding member after the step of determining a value indicative of the presence and/or amount of reporter compound captured on the second binding member; forming complexes of a subset of the amount of reporter compound with at least a subset of the amount of target nucleic acid; capturing a remaining subset of the amount of reporter compound not in complex with a target nucleic acid on the second binding member; and determining the value indicative of the presence and/or amount of reporter compound captured on the second binding member. In such an embodiment, the steps of releasing, forming complexes, capturing and determining can be performed N additional times, wherein N is an integer greater than or equal to 1, e.g., N≥5, N≥10 or N≥20.

Further, the step of forming complexes of a subset of the amount of reporter compound with at least a subset of the amount of target nucleic acid and the step of capturing a remaining subset of the amount of reporter compound not in complex with a target nucleic acid on the second binding member can be performed concomitantly.

The method can further include subjecting the target nucleic acid to amplification. In such an embodiment, amplification of the target nucleic acid can be initiated prior to the step of forming complexes of a subset of the amount of reporter compound with at least a subset of the amount of target nucleic acid.

The value indicative of the presence and/or amount of reporter compound captured on the second binding member can be determined before the steps of forming of complexes of a subset of the amount of reporter compound with at least a subset of the amount of target nucleic acid and of capturing a remaining subset of the amount of reporter compound not in complex with a target nucleic acid on the second binding member are in chemical equilibrium. Particularly, the value indicative of the presence and/or amount of reporter compound captured on the second binding member can be determined 1 seconds to 120 seconds after initiating the steps of forming complexes of a subset of the amount of reporter compound with at least a subset of the amount of target nucleic acid, and of capturing a remaining subset of the amount of reporter compound not in complex with a target nucleic acid on the second binding member.

The method can further include subjecting the target nucleic acids to reverse transcription prior to subjecting them to amplification.

The second binding member can include one or more different reporter specific capture molecules being capable of capturing a reporter compound on the second binding member. The capture molecules can be oligonucleotides. The different reporter specific capture molecules can be arranged on different locations with respect to the second binding member. Further, the reporter compounds can be captured on the second binding member by forming complexes with the reporter-specific capture molecules. At least a part of an interaction site of the reporter compound being capable of forming a complex with a target nucleic acid can also be capable of forming a complex with a reporter specific capture molecule. The reporter specific capture molecules and the target nucleic acid can compete for forming a complex with the reporter compound.

The amplification can include a step of denaturing double-stranded nucleic acids. Double-stranded nucleic acids can include complexes of reporter compounds with target nucleic acids, complexes of reporter compounds with reporter specific capture molecules, double strands of reporter compounds and double strands of target nucleic acids.

The amplification can further include a step of annealing primer molecules to target nucleic acids. In this embodiment, the annealing step can be performed concomitantly with the step of forming complexes of a subset of the amount of reporter compound with at least a subset of the amount of target nucleic acid and/or the step of capturing a remaining subset of the amount of reporter compound not in complex with a target nucleic acid on the second binding member.

The amplification can be a cyclic amplification, e.g., a PCR. Performing the PCR can include using a polymerase having exonuclease activity. The cyclic amplification can include at least 10 cycles or at least 20 cycles.

The value indicative of the presence and/or amount of reporter compound captured on the second binding member can be determined after at least one cycle, e.g., after each cycle, of the cyclic amplification. Further, the value indicative of the presence and/or amount of target nucleic acid can be determined each time after determining the value indicative of the presence and/or amount of reporter compound captured on the second binding member.

Determining the value indicative of the presence and/or amount of reporter compound captured on the second binding member can include time-dependent monitoring of the indicative value.

Further, the value indicative of the presence and/or amount of target nucleic acid can be determined based on a calibration curve correlating the value indicative of the presence and/or amount of reporter compound with a value indicative of the presence and/or amount of target nucleic acid.

The method can also be performed in a device as described above. For example, the method can be performed in a device, including a rigid substrate; a flexible cover element at least partially covering the substrate; a first structure formed in the substrate, adapted for accommodating liquids and adapted for releasing contents of one or more cells, spores, or viruses, the contents including target nucleic acids; a second structure formed in the substrate, adapted for accommodating liquids and including at least one binding member adapted for capturing the target nucleic acids and for determining a value indicative of the presence and/or amount of the target nucleic acids; a microfluidic network interconnecting at least the first structure and the second structure; and an actuator unit adapted for effecting a fluid flow between the first structure and the second structure by pressing the flexible cover element against the substrate to selectively close a portion of the microfluidic network. The method can also be performed in a device, including a structure adapted for accommodating liquids, wherein the structure includes at least one binding member and is in fluid communication with a microfluidic network; and a control unit adapted for controlling a fluid flow through the microfluidic network in such a manner that target nucleic acids are captured at the at least one binding member, adapted for controlling an amplification of the target molecules in the structure, and adapted for controlling detection of compounds captured at the at least one binding member.

The device can further include a first structure adapted for accommodating liquids. In such an embodiment, the step of forming complexes each including a target nucleic acid and a capture molecule is performed in the first structure.

The device can further include a second structure adapted for accommodating liquids and the first and, optionally, the second binding member can be provided in the second structure. In such an embodiment, forming complexes each including a target nucleic acid and a capture molecule; contacting the complexes with the first binding member to bind the complexes to the first binding member; releasing at least a subset of the amount of target nucleic acid from the first binding member; forming complexes of a subset of the amount of a reporter compound with at least a subset of the amount of target nucleic acid; capturing a remaining subset of the amount of reporter compound not in complex with a target nucleic acid on the second binding member; and determining a value indicative of the presence and/or amount of reporter compound captured on the second binding member is performed in the second structure, e.g., the central well.

Providing the one or more target nucleic acids can include providing a sample including the one or more target nucleic acids. The sample can be a liquid sample having a volume of 1 μL to 50 μL Further, the sample can be a liquid whole blood sample.

In another aspect, a method includes amplifying at least one target polynucleotide to form double-stranded amplicons, contacting the amplicons with a surface configured to selectively bind the amplicons, and with the amplicons bound to the surface by an anchor group, optically determining the presence of the amplicons. The method can further include releasing the amplicons from the surface after the step of optically detecting, subjecting the released amplicons to at least one more amplification cycle, contacting the resulting amplicons with the surface, and with the amplicons bound to the surface by the anchor group, optically determining the presence of the amplicons. The method can further include performing the steps of releasing, subjecting, contacting, and optically determining a number N additional times, where N is an integer greater than or equal to 1. Particularly, N≥5, more particularly N≥10, and still more particularly N≥20.

The method can further include, prior to the step of amplifying, providing the target polynucleotides, forming complexes each including a target polynucleotide released from a pathogen and at least one capture molecule, each capture molecule including a binding portion specific to a region of the target polynucleotide and an anchor group, and contacting the complexes with the surface, the surface being configured to non-selectively bind the anchor group of the capture molecule to non-selectively bind the complexes and the surface. In such a method, providing the polynucleotides can include releasing contents of one or more cells, spores, or viruses, the contents including the target polynucleotides. The step of releasing can include contacting a sample including the one or more cells, spores, or viruses with a lysing reagent and the capture molecules. The step of contacting the sample with the lysing reagent and capture molecules can include contacting the sample with the lysing reagent and capture molecules in lyophilized form.

In such a method, the step of providing the target polynucleotides can include providing concomitant materials, and the method can further include separating the surface-bound complexes and the concomitant materials. In such a method, the concomitant materials can include contents of at least one cell, spore, or virus from which the polynucleotides have been released. The surface can be a surface of a particle.

In yet another aspect, a method includes providing one or more target polynucleotides, forming complexes each including a target polynucleotide and at least one capture molecule, each capture molecule including a binding portion specific to a region of the target polynucleotide and an anchor group, and contacting the complexes with a surface, the surface being configured to non-selectively bind the anchor group of the capture molecule to non-selectively bind the complexes and the surface. In such a method, the step of providing can include releasing the contents of one or more cells, spores, or viruses and the contents including the polynucleotides. The method can further include separating the surface-bound complexes and other contents released from the one or more cells, spores, or viruses.

In another aspect, a method includes forming a composition of matter including an amount of a reporter compound, a binding member capable of capturing the reporter compound, and an amount of a target nucleic acid capable of forming complexes with the reporter compound, the forming of complexes with the reporter compound inhibiting capturing of the reporter compound by the binding member; forming complexes of a subset of the amount of reporter compound with at least a subset of the amount of target nucleic acid; capturing a remaining subset of the amount of reporter compound not in complex with a target nucleic acid on the binding member; and determining a value indicative of the presence and/or amount of reporter compound captured on the binding member.

In other words, the method can include allowing a subset of the amount of reporter compound to form a complex with at least a subset of the amount of target nucleic acid, and allowing a remaining subset of the amount of reporter compound not in complex with a target nucleic acid to be captured on the binding member.

The method can be performed in a device selected from the group consisting of a biosensor assay device, a microfluidic cartridge, and a lab-on-chip.

In some embodiments, the method further includes determining a value indicative of the presence and/or amount of target nucleic acid based on the value indicative of the presence and/or amount of reporter compound captured on the binding member. The determination of the value indicative of the presence and/or amount of reporter compound captured on the binding member can include time-dependent monitoring of the indicative value. In specific embodiments, the value indicative of the presence and/or amount of target nucleic acid is determined based on a calibration curve correlating the value indicative of the presence and/or amount of reporter compound with the value indicative of the presence and/or amount of target nucleic acid.

In other embodiments, the method further includes releasing the remaining subset of the amount of reporter compound from the binding member after the steps of forming complexes of a subset of the amount of reporter compound with at least a subset of the amount of target nucleic acid, capturing a remaining subset of the amount of reporter compound not in complex with a target nucleic acid on the binding member, and determining a value indicative of the presence and/or amount of reporter compound captured on the binding member.

The steps of releasing, forming complexes, capturing, and determining a value indicative of the presence and/or amount of target nucleic acid can be performed a number N additional times, where N is an integer greater than or equal to 1. In specific embodiments, N is ≥5,≥10 or ≥20.

The method can further include, prior to the step of forming complexes: capturing at least a subset of the amount of reporter compound on the binding member; determining a value indicative of the presence and/or amount of reporter compound captured on the binding member; and releasing captured reporter compounds from the binding member.

In some embodiments, the step of forming complexes of a subset of the amount of reporter compound with at least a subset of the amount of target nucleic acid and the step of capturing a remaining subset of the amount of reporter compound not in complex with a target nucleic acid on the binding member are performed concomitantly.

In further embodiments, the method includes subjecting the target nucleic acid to amplification. Amplification of the target nucleic acid can be initiated prior to the step of forming complexes of a subset of the amount of reporter compound with at least a subset of the amount of target nucleic acid.

The value indicative of the presence and/or amount of reporter compound captured on the binding member can be determined before the forming of complexes of a subset of the amount of reporter compound with at least a subset of the amount of target nucleic acid and the capturing of a remaining subset of the amount of reporter compound not in complex with a target nucleic acid on the binding member are in chemical equilibrium. In some embodiments, the value indicative is determined 1 seconds to 120 seconds after initiating the steps of forming complexes of a subset of the amount of reporter compound with at least a subset of the amount of target nucleic acid and of capturing a remaining subset of the amount of reporter compound not in complex with a target nucleic acid on the binding member.

The reporter compounds can include one or more detectable labels. In specific embodiments, the one or more detectable labels are fluorescent labels. In other specific embodiments, the reporter compounds are oligonucleotides.

In other embodiments, the method further includes subjecting the target nucleic acids to reverse transcription prior to subjecting them to amplification.

In other embodiments, the step of forming a composition of matter includes forming a composition of matter including an amount of a first reporter compound, an amount of a first target nucleic acid capable of forming complexes with the first reporter compound, the forming of complexes with the first reporter compound inhibiting capturing of the first reporter compound by the binding member, an amount of a second reporter compound, and an amount of a second target nucleic acid capable of forming complexes with the second reporter compound, the forming of complexes with the second reporter compound inhibiting capturing of the second reporter compound by the binding member.

The binding member used in the method can include one or more different capture molecules being capable of capturing a reporter compound on the binding member. The capture molecules can also be denoted as reporter specific capture molecules. In specific embodiments, the capture molecules are oligonucleotides. The different capture molecules can also be arranged on different locations with respect to the binding member.

The reporter compounds can be captured on the binding member by forming complexes with the capture molecules. In specific embodiments, at least a part of an interaction site of the reporter compound being capable of forming a complex with a target nucleic acid is also capable of forming a complex with a capture molecule. In other specific embodiments, the capture molecules and the target nucleic acid compete for forming a complex with the reporter compound.

In other embodiments, the amplification includes a step of denaturing double stranded nucleic acids. The double stranded nucleic acids can include complexes of reporter compounds with target nucleic acids, complexes of reporter compounds with capture molecules, double strands of reporter compounds, and double strands of target nucleic acids.

The amplification can also include a step of annealing primer molecules to target nucleic acids. The annealing step can be performed concomitantly with the step of forming complexes of a subset of the amount of reporter compound with at least a subset of the amount of target nucleic acid and/or with the step of capturing a remaining subset of the amount of reporter compound not in complex with a target nucleic acid on the binding member.

The amplification can be a cyclic amplification. In specific embodiments, the cyclic amplification is a PCR. The cyclic amplification can include at least 10 or at least 20 cycles. In other embodiments, performing the PCR includes using a polymerase having exonuclease activity.

The value indicative of the presence and/or amount of reporter compound captured on the binding member can be determined after at least one cycle of the cyclic amplification. In specific embodiments, this value is determined after each cycle of the cyclic amplification. In other embodiments, the value indicative of the presence and/or amount of target nucleic acid is determined each time after determining the value indicative of the presence and/or amount of reporter compound captured on the binding member.

A device can be provided which is configured to perform any one of the above described methods.

Further aspects, objects and advantages will be apparent from the description below, the drawings, and the claims.

BRIEF DESCRIPTION OF THE DRAWINGS

The illustration in the drawings are schematic. In different drawings, similar or identical elements are provided with the same reference signs.

FIG. 1b is a view of a detection system useful in performing the method of FIG. 1a.

FIG. 1c is a view of the detection system of FIG. 1b, with the detection system being shown in an actuated state for performing a detection step of the method of FIG. 1a.

FIG. 15 illustrates that the agarose gel electrophoresis shows that polynucleotides (i.e., HIV-RNA) captured on strepavidin sepharose particles can be used directly as a template for the amplification without further processing steps (i.e., elution, dilution or concentration).

FIG. 16 shows the respective fluorescent images of strepavidin sepharose particles, wherein more fluorescent strepavidin sepharose particles are detected in the positive probe as compared to the negative probe.

FIG. 24 shows the principle as well as the results of an array-based competitive assay for determining the amount of a HIV gag/env PCR product in a sample.

FIG. 25 illustrates different steps during the assay shown in FIG. 24.

DETAILED DESCRIPTION

Figure 1A:
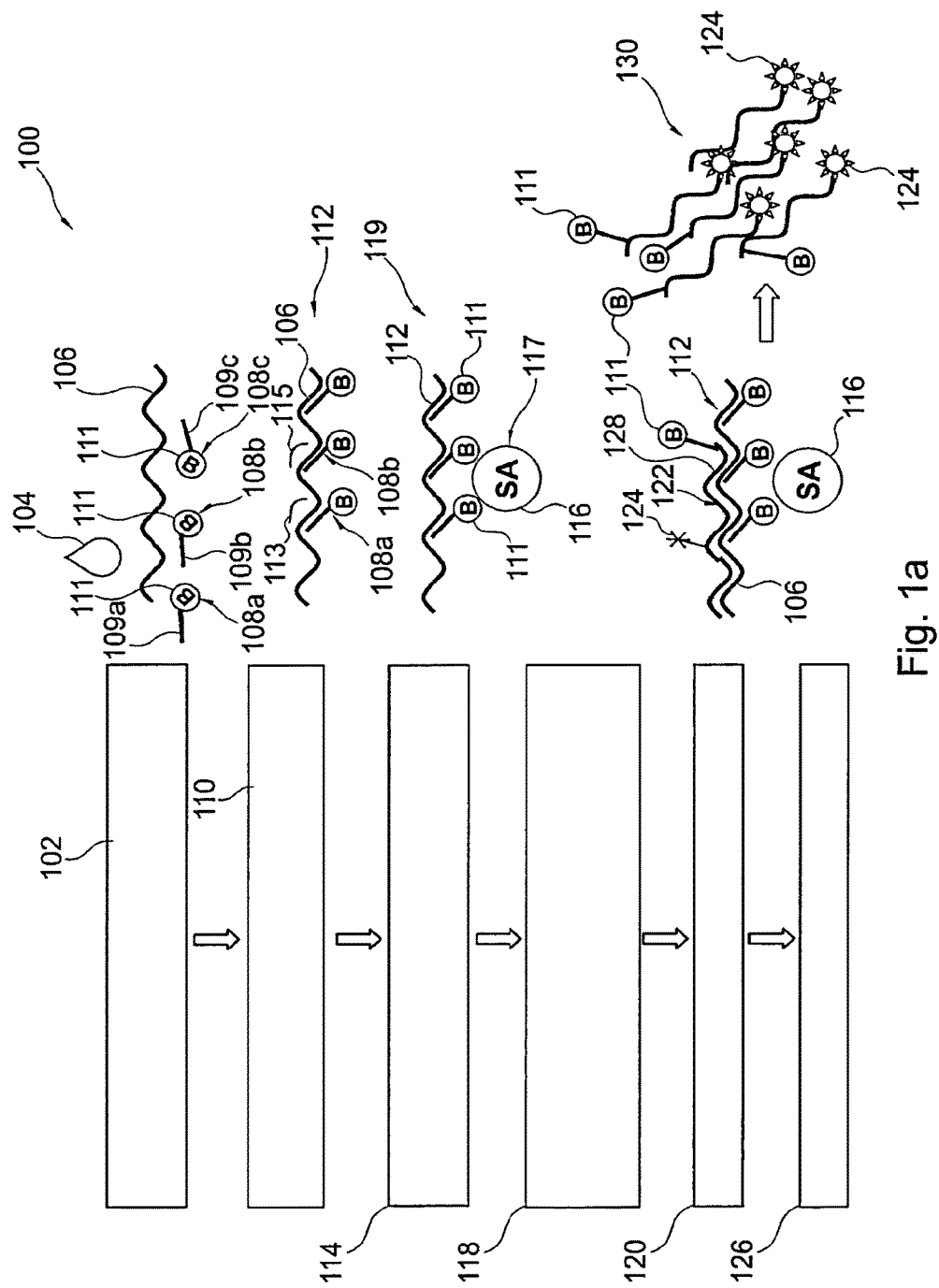
FIG. 1a is a flow chart of a polynucleotide assay method.

Analysis of biological samples can include determining whether one or more polynucleotides (for instance, a DNA, RNA, mRNA, or rRNA) are present in the sample. For example, one can analyze a sample to determine whether a polynucleotide indicative of the presence of a particular pathogen is present.

In one embodiment, a method for the analysis includes forming complexes, each including a target nucleic acid and a capture molecule, wherein each capture molecule includes a binding portion specific to a region of the target nucleic acid and an anchor group; contacting the complexes with a binding member, the binding member being configured to bind the anchor group of the capture molecule to bind the complexes to the binding member; subjecting one or more target nucleic acids to a amplification; capturing the amplified target nucleic acids with respect to the binding member; and determining a value indicative of the presence and/or amount of the captured target nucleic acids.

The term target nucleic acid can refer to a nucleic acid molecule that can be detected by the method (i.e., target nucleic acids that are capable of forming complexes with a capture molecule; see below). Examples of such nucleic acid molecules include naturally occurring nucleic acids such as deoxyribonucleic acid (DNA) or ribonucleic acid (RNA) as well as artificially designed nucleic acids, e.g., nucleic acid analogs such as, inter alia, peptide nucleic acids (PNA) or locked nucleic acids (LNA), that are chemically synthesized or generated by means of recombinant gene technology (see, for example, Sambrook, J. et al. (1989) *Molecular, Cloning: A Laboratory Manual,* 2nd ed., Cold Spring Harbor Laboratory Press, Cold Spring Harbor, N.Y., which is incorporated by reference in its entirety). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, target nucleic acids are 10 to 10,000 nucleotides in length, e.g., 20 to 2,000 nucleotides, 30 to 1,000 nucleotides or 50 to 500 nucleotides. As used herein, the term "nucleotide" is to be understood as referring to both ribonucleotides and deoxyribonucleotides (i.e., RNA and DNA molecules).

The target nucleic acid can be a nucleic acid associated with viral infections. A nucleic acid associated with viral infections denotes any nucleic acid molecule of viral origin (i.e., whose nucleotide sequence is identical or complementary to a corresponding sequence within the virus genome) that is present in a liquid sample to be analyzed that has been infected by one or more virus species. The viruses infecting the host, from which the liquid sample is obtained, can be a DNA virus (i.e., a virus having a DNA genome) or an RNA virus (i.e., a virus having a RNA genome) (reviewed, e.g., in: Büchen-Osmond, C. (2003). *Taxonomy and Classification of*

*Viruses*. In: Manual of Clinical Microbiology, 8th ed., vol. 2, p. 1217-1226, ASM Press, Washington D.C., which is incorporated by reference in its entirety). Examples of DNA viruses include, inter alia, the families of Papovaviridae (e.g., papillomavirus), Adenoviridae (e.g., adenovirus), and Herpesviridae (e.g., Epstein-Barr virus, cytomegalovirus). Examples of RNA viruses include, inter alia, the families of Picornaviridae (e.g., poliovirus, rhinovirus) Flaviviridae (e.g., hepatitis C virus), Filoviridae (e.g., Marburg virus, ebolavirus), and Retroviridae (e.g., human immunodeficiency virus (HIV)). In some embodiments, the nucleic acids to be detected are associated with infections caused by members of the Retroviridae, particularly they are associated with HIV infections. The term "HIV", as used herein, refers to both the HIV-1 and HIV-2 species and to any subtypes derived thereof.

Since many DNA viruses as well as the Retroviridae (notably, the replication of the Retroviridae generally requires reverse transcription of the RNA virus genome into DNA), can integrate their genetic information into the host cell's genome in form of a latent pro-virus, the term "nucleic acids associated with viral infections" does not only refer to nucleic acids originating from free and from cell-associated viruses but also includes pro-viral DNA molecules being integrated into the host's genome, reverse transcribed viral DNA molecules (i.e., the "intermediates" of viral replication), and transcripts derived from pro-viral DNA (i.e., RNA molecules obtained by transcription of the host DNA genome).

Typically, the target nucleic acids are not subjected to the method in isolated form, but in the form of a sample that is suspected of including one or more species of target nucleic acids. The term "one or more species" refers to one or more different types of nucleic acids such as molecules having different nucleotide sequences and/or molecules descending from different origins (e.g., nucleic acids derived from different pathogens infecting a host cell).

The term sample refers to any liquid which is to be analyzed, and which is suspected of including one or more species of target nucleic acids to be detected. Thus, a sample can include purified nucleic acid preparations dissolved in water or a suitable buffer (e.g., Tris/EDTA) as well as various biological samples. Examples of liquid samples that can be analyzed using the invention include, inter alia, organic and inorganic chemical solutions, drinking water, sewage, human and non-human body fluids such as whole blood, plasma, serum, urine, sputum, salvia or cerebrospinal fluid, cellular extracts from animals, plants or tissue cultures, prokaryotic and eukaryotic cell suspensions, phage preparations and the like.

Whole blood can refer to blood with all its constituents. In other words, whole blood includes both blood cells such as erythrocytes, leukocytes, and thrombocytes, and blood plasma in which the blood cells are suspended.

The sample can further include one or more additional agents such as diluents, solvents or buffers that can result from an optional purification and/or processing of the sample prior to subjecting it to the method. However, in some embodiments, the sample analyzed is an untreated sample such as an untreated whole blood sample. The term untreated can indicate that after collecting the sample (e.g., by blood withdrawal from a patient) and before subjecting it to the method, no further sample processing (e.g., fractionation methods, drying/reconstitution, or the like) occurs.

The volume of the fluid sample to be analyzed can be in the range of 1 μL to typically in the range of 1 μL to 45 μL or 1 μL to 40 μL or 1 μL to 30 μL or 1 μL to 25 μL or 1 μL to 20 μL or 1 μL to 15 μL. In particular embodiments, the volume of the fluid sample is in the range of 1 μL to 10 μL. Samples of whole blood can be analyzed using sample volumes exceeding 50 μL as well.

A capture molecule refers a molecule that shows a specific binding behavior and/or a characteristic reactivity, which makes it suitable for the formation of complexes with a target nucleic acid. Nucleic acids are typically used as capture molecules. Examples of nucleic acids that can be used as capture molecules include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, nucleic acid capture molecules are single-stranded oligonucleotides having a length of 10 to 150 nucleotides, e.g., of 20 to 100 nucleotides or 30 to 70 nucleotides. In specific embodiments, the capture molecules can be used as primers in a PCR in order to amplify any target nucleic acid of interest being present in a given fluid sample.

In some embodiments, the capture molecules can include at least one specific sequence region (i.e., the binding portion referred to above), which is complementary to a sequence region of a target nucleic acid (e.g., a nucleic acid associated with a viral infection), thus allowing base-pairing between the capture molecules and the nucleic acid to be detected. Typically, the specific binding region is at least 20 nucleotides in length, e.g., at least 30 nucleotides, or at least 40 nucleotides. Particularly, the nucleotide sequence of the binding region of the capture molecules is complementary to the corresponding nucleotide sequence of the target nucleic acid.

The capture molecules can be provided (e.g., in lyophilized or dried form) in one or more of the at least one structure adapted for accommodating liquids of the device as described above prior to the introduction of the fluid sample to be analyzed. Alternatively, the capture molecules can be introduced into the device along with the sample (e.g., concomitantly) or after the sample has already been introduced.

One or more species of capture molecules can be employed. In other words, one or more different types of capture molecules such as one or more nucleic acid molecules having different nucleotide sequences can be used. More than one species of capture molecule concomitantly used can also be referred to as "library". Such libraries include at least two different molecules but can also include many more different molecules, e.g., at least 5 different species, at least 10 different species, at least 30 different species and so forth. The libraries can also be present in form of array elements or any other spatial arrangement.

In some embodiments, the analysis performed in the device further includes contacting the complexes including a target nucleic acid to be detected and a capture molecule with a binding member of the device, the binding member being configured to bind the anchor group of the capture molecule in order to bind the complexes to the binding member.

The terms binding member or support member refer to any matrix to which capture molecules (and thus also any complexes including such capture molecule) can be coupled via the anchor group of the capture molecules by covalent or non-covalent interactions. Examples of such matrices include, inter alia, the substrates of array elements or synthetic particles such as magnetic beads (e.g., paramagnetic polystyrol beads, also known as Dynabeads®) and latex beads as well as porous surfaces such as CPG and the like. Depending on the type of capture molecule, the type of anchor group, and the intended application, in each case a large variety of linkages are possible. For example, in case the anchor group of the capture molecules can be a biotin moiety, which can be coupled to an avidin or a streptavidin group being attached to the binding member. Alternatively, the capture molecules can include a stretch of adenosine residues (e.g., 10 adenosine residues) that will interact with a corresponding stretch of thymidine residues bound to the binding member. Specific coupling reagents including anchor groups are commercially available from different providers and well established in the art (see, for example, Sambrook, J. et al., supra; Ausubel, F. M. et al., supra, and Lottspeich, F., and Zorbas H., supra).

The binding member can be provided in one or more of the structures of the device prior to the introduction of the fluid sample to be analyzed. The binding member can be provided in the same structure as the capture molecules or in at least one different structure. Typically, the step of forming complexes of capture molecules with target nucleic acids is performed spatially separated from the step of contacting the complexes with the binding member, i.e., in different structures or wells or reaction chambers of the device. For example, the step of forming complexes of capture molecules with target nucleic acids can be performed in a lysis well and the step of contacting the complexes with the binding member can be performed in a central well, depicted for example in FIGS. 17A-D. In such embodiments, 10 capture molecules and the binding member are usually provided in different structures adapted for accommodating liquids. Instead of providing the binding member in the device prior to adding the sample, the binding member can be introduced into the device along with the sample (i.e., concomitantly) or after the sample has already been introduced.

In particular embodiments, the method further includes subjecting the target nucleic acid to amplification, that is, to increase their amount present in the sample before subjecting the same to the further analysis in order to facilitate further detection. Typically, target nucleic acid amplification is achieved by means of a cyclic amplification. The cyclic amplification can include any number of amplification cycles that is equal or greater than two. Usually, cyclic amplification reaction includes at least 10 or at least 20 cycles.

An exemplary cyclic amplification is a polymerase chain reaction (PCR). PCR is an established standard method in molecular biology that is described in detail, e.g., in Sambrook et al., supra; and in Ausubel, F. M. et al., supra. Typically, PCR is used for the amplification of double-stranded DNA molecules by employing a thermostable DNA polymerase. In some embodiments, the DNA polymerase used in the cyclic amplification has exonuclease activity, particularly 5'→3' exonuclease activity. Examples of such DNA polymerases include, inter alia, Taq DNA polymerase or Tth DNA polymerase (which are commercially available from multiple providers).

When the target nucleic acid is a RNA molecule, the target nucleic acid can be subjected to reverse transcription (that is, to produce a DNA molecule from a corresponding RNA molecule) prior to subjecting them to amplification. Reverse transcription is another standard method in molecular biology and also described, e.g., in Sambrook et al., supra; and in Ausubel, F. M. et al., supra.

For nucleic acid amplification, the device can include one or more temperature control units and/or temperature regulating units for controlling and/or regulating the temperature within the reaction chamber. Such a temperature control unit and/or temperature regulating unit can include one or more separate heating and/or cooling elements, which can directly contact one or more reaction chambers of the device. Typically, the one or more heating and/or cooling elements are made of a heat conductive material. Examples of such heat conductive materials include, inter alia, silicon, ceramic materials like aluminium oxide ceramics, and/or metals like high-grade steel, aluminium, copper, or brass. An exemplary description of a suitable temperature control unit and/or temperature regulating unit can also be found in the International Patent Application WO 01/02094, which is incorporated by reference in its entirety.

For example, controlling/regulating the temperature within a structure adapted for accommodating liquids can also be achieved by using a chamber body made of an electrically conductive material. The chamber body can be a solid body surrounding at least partially the at least one structure or reaction chamber of the device. The structure can be, at least in part, an integral component of the chamber body (i.e., is made of the same material as the chamber body). Examples of electrically conductive materials include electrically conductive synthetic materials, such as polyamide with 5 to 30% carbon fibres, polycarbonate with 5 to 30% carbon fibres, polyamide with 2 to 20% stainless steel fibres, and polyphenylene sulfide with 5 to 40% carbon fibres. Furthermore, the chamber body can be designed to include swellings and diminutions, which allow specific heating of the reaction chamber or the corresponding surfaces.

Measuring the temperature in the structure can be performed by various methods well established in the art, for example by using integrated resistance sensors, semi-conductor sensors, light waveguide sensors, polychromatic dyes or liquid crystals. Furthermore, the temperature in the reaction chamber can be determined by using an integrated temperature sensor in the chamber body, a pyrometer or an infrared sensor, or by measuring the temperature-dependent alteration of parameters such as the refraction index at the surface on which detection takes place or the pH value of the sample, for example by measuring the colour alteration of a pH-sensitive indicator.

Usually, amplification such as a PCR includes three basic steps—denaturation, annealing of the primers, and extension of the primers—that are iteratively performed in a cyclic manner. However, the amplification can further include an initial denaturation step prior to the first "true" amplification cycle and/or a final extension step after completion of the final amplification cycle, respectively. In some embodiments, target nucleic acid amplification includes (at least) a step of denaturing double-stranded nucleic acids and/or a combined step of annealing and extending the primer molecules at the target nucleic acids (i.e., a "two-step PCR").

Typically, the denaturation step involves the heating of the sample to be analyzed to a temperature of 94-95° C., typically for 0.5 seconds to 5 minutes, thus resulting in the strand-dissociation of double-stranded nucleic acid templates. Subjecting a sample to be analyzed to such denaturation step results in (i.e., allows) the simultaneous denaturation of the double stranded nucleic acids in the sample including double-stranded target nucleic acids and complexes of capture molecules with target nucleic acids (attached to the binding member), the latter resulting in the release of the target nucleic acids from the binding member.

Typically, the annealing step involves the cooling down of the sample to be analyzed to a temperature of 40-65° C., typically for 1 second to 5 minutes, to allow the association (i.e., the hybridization/base-pairing) of the primer molecules to the denatured nucleic acid template strands. The reaction temperature employed depends on the chemical and/or physical properties of the primer molecules to be annealed such as their nucleotide sequence composition, melting temperature, their tendency for intra-molecular folding (e.g., the formation of double-stranded hairpin or turn structures), and the like. Within some embodiments, subjecting a sample to be analyzed to such annealing step results in (i.e., allows) the re-association of double-stranded target molecules, and the forming of complexes of target nucleic acids with capture molecules, the latter resulting in the capturing or re-capturing of the target nucleic acids on the binding member. Thus, in some embodiments, the annealing step is performed concomitantly with the step of capturing target nucleic acids on the binding member by forming complexes with the capture molecules.

Finally, a typical extension step involves the extension of the hybridized primer molecules to produce full-length copies of the DNA template strands by a DNA polymerase. The length of the amplified DNA fragment is determined by the 5' ends of the pair of primers employed. Typically, the elongation step is performed at a temperature of 70-72° C. for 1 second to 10 minutes. Within some embodiments, subjecting a sample to be analyzed to such extension step can result in the replication of the target nucleic acids to be analyzed by allowing the complexes of a primer with a target nucleic that have been formed during the annealing step to be extended to generate double-stranded amplified nucleic acid fragments optionally having incorporated a detectable marker that subsequently can be detected.

In specific embodiments, the method further includes capturing the target nucleic acids that have been amplified, typically by subjecting the sample to be analyzed to PCR, with respect to the binding member (i.e., immobilizing the target nucleic acids thereon). As already described above, the target nucleic acids can be captured with respect to the binding member by forming complexes with the capture molecules which are still coupled to the binding member via the anchor group.

The method can further include releasing the captured amplified target nucleic acids from the binding member and repeating the steps of subjecting one or more target nucleic acids to amplification and capturing the amplified target nucleic acid with respect to the binding member. Releasing can include the detachment or unbinding of the target nucleic acids from the binding member. This can be accomplished, for example, enzymatically via the cleavage of any covalent bonds or in cases, where the target nucleic acids are bound to the binding member by nucleic acid capture molecules via complementary base-pairing, by increasing the temperature in the structure, in which the assay is performed, thus resulting in nucleic acid strand separation (i.e., denaturation).

In such an embodiment, the cycle of releasing the captured amplified target nucleic acids from the binding member and repeating the steps of subjecting one or more target nucleic acids to amplification and capturing the amplified target nucleic acids with respect to the binding member can be performed at least 5 times, at least 10 times, at least 20 times, at least 30 times, at least 50 times or at least 100 times. The step of determining a value indicative of the presence and/or amount of the captured target nucleic acids can be performed after at least one cycle, e.g., after each cycle of releasing the captured amplified target nucleic acids from the binding member and repeating the steps of subjecting one or more target nucleic acids to amplification and capturing the amplified target nucleic acids with respect to the binding member.

Figure 18:
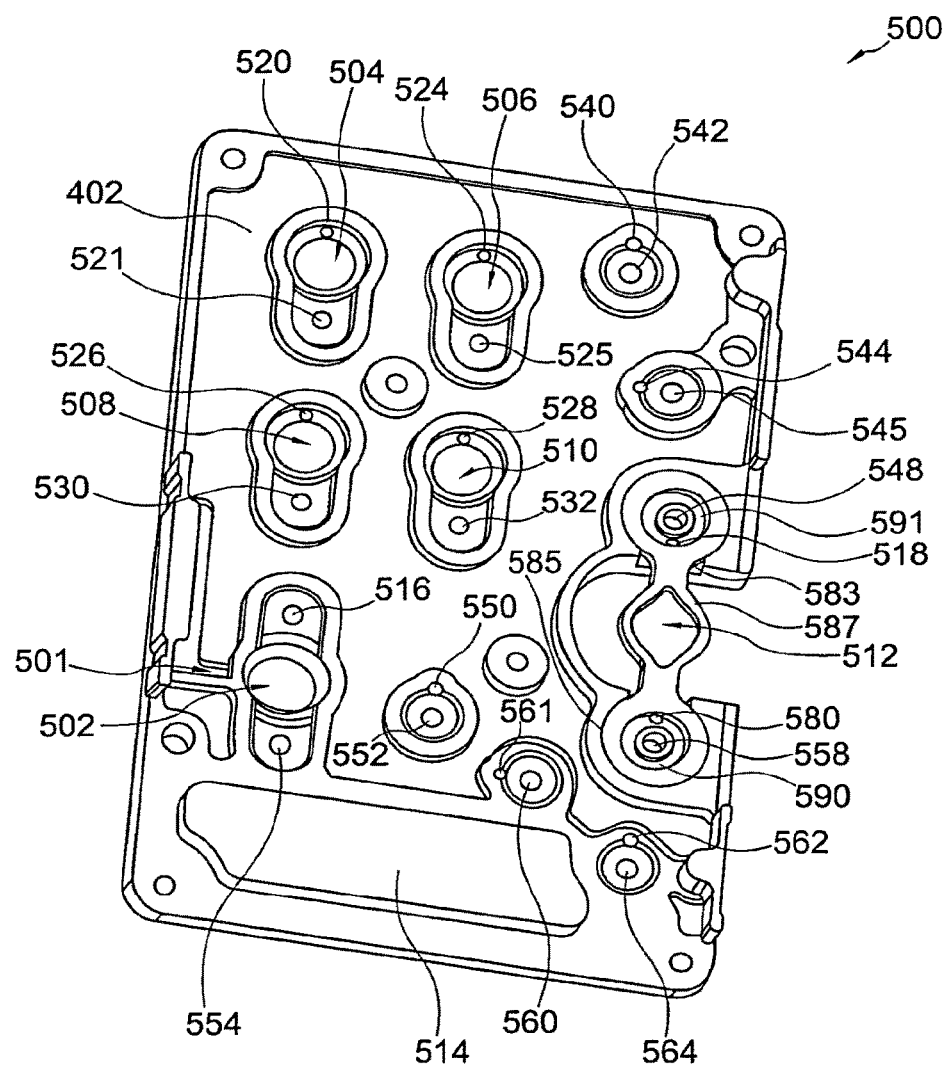
FIG. 18 illustrates a front side of a device.
Figure 19:
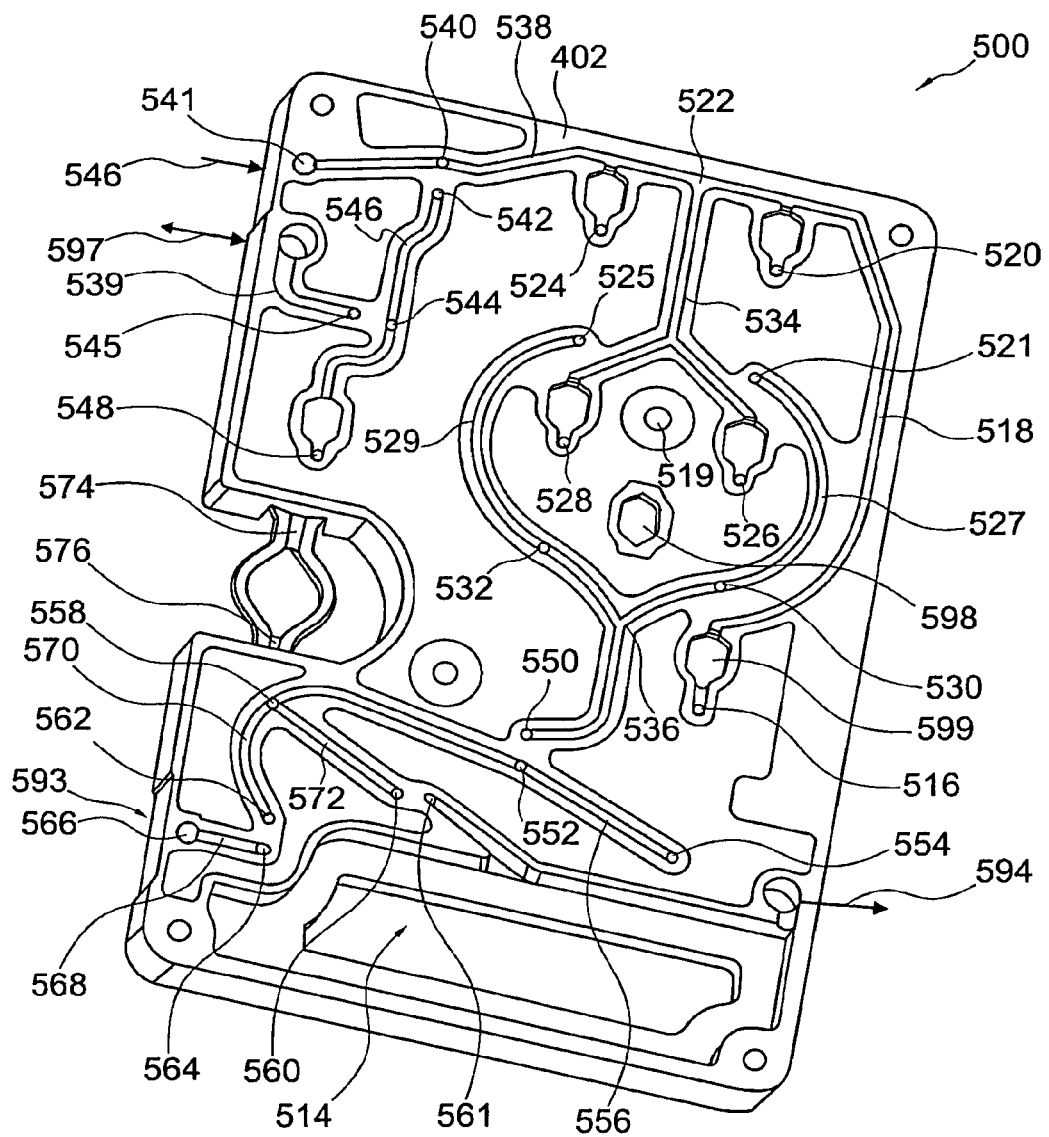
FIG. 19 illustrates a back side of the device of FIG. 18.

The step of forming complexes, each including a target nucleic acid and a capture molecule, wherein each capture molecule includes a binding portion specific to a region of the target nucleic acid and an anchor group can be performed spatially separated from the step of contacting the complexes with a binding member, the binding member being configured to bind the anchor group of the capture molecule to bind the complexes to the binding member. In such an embodiment, the method is performed in a device which includes at least two structures adapted for accommodating liquids. The at least two structures can be in fluid communication, e.g., with a microfluidic network. For example, the method can be performed in device 500 as illustrated in FIGS. 18 and 19. The complexes each including a target nucleic acid and a capture molecule can be formed in the first structure 502. The complex can then be transferred to the second structure 512, in which the complexes are contacted with a binding member as described above which is configured to bind an anchor group of the capture molecule.

Determining a value indicative of the presence and/or amount of the captured target nucleic acids can include the detection/determination of parameters such as electrical conductivity, redox potential, optical absorption, fluorescence intensity or bioluminescence that allow for qualitative and/or quantitative measurements of the target nucleic acids captured (or re-captured) on the binding member. Only one of these parameters can be determined but it is also possible to determine more than one parameter (e.g., electrical conductivity and the intensity of a fluorescence signal caused by a suitable label), either concomitantly or consecutively.

For performing the detection reaction, the target nucleic acids can be labelled with one or more detectable labels. A detectable label can be any compound or moiety that includes one or more appropriate chemical substances or enzymes, which directly or indirectly generate a detectable compound or signal in a chemical, physical or enzymatic reaction. Such a label can thus be necessary for or will facilitate detection of the reporter compound of interest by being capable of forming interactions with said reporter compound. As used herein, the term is to be understood to include both detectable labels as such (also referred to as "markers") as well as any compounds coupled to one or more such detectable markers. Furthermore, moieties interfering with the generation of a detectable signal by a label (e.g., a quencher "hijacking" the emissions that resulted from excitation of the fluorophor, as long the quencher and the fluorophor are in close proximity to each other) can also belong to the detectable labels. The detectable labels can be incorporated or attached to the target nucleic acids, e.g., in form of modified and/or labelled ribonucleotides, deoxynucleotides or dideoxynucleotides.

Labeling can be achieved by methods well known in the art (see, for example, Sambrook, J. et al., supra; and Lottspeich, F., and Zorbas H., supra). The labels can be selected from, inter alia, fluorescent labels, enzyme labels, colored labels, chromogenic labels, luminescent labels, radioactive labels, haptens, biotin, metal complexes, metals, and colloidal gold. All these types of labels are well established in the art. An example of a physical reaction that is mediated by such labels is the emission of fluorescence or phosphorescence upon irradiation or excitation or the emission of X-rays when using a radioactive label. Alkaline phosphatase, horseradish peroxidase, β-galactosidase, and β-lactamase are examples of enzyme labels, which catalyze the formation of chromogenic reaction products. In specific embodiments, the detectable labels are fluorescent labels. Numerous fluorescent labels are well established in the art and commercially available from different suppliers (see, for example, *The Handbook—A Guide to Fluorescent Probes and Labeling Technologies,* 10th ed. (2006), Molecular Probes, Invitrogen Corporation, Carlsbad, Calif., USA, which is incorporated by reference in its entirety).

For detecting such labels, a detection system can be used which is suitable for determining values indicative of the presence and/or amount of reporter compound captured on a support member. The detection system can be connected to the device 500. Typically, the detection system is positioned opposite to one of the second structure 512, optionally opposite to a particular surface region where detection takes place. The selection of a suitable detection system depends on several parameters such as the type of labels used for detection or the kind of analysis performed. Various optical and non-optical detection systems are well established in the art. A general description of detection systems that can be used with the method can be found, e.g., in Lottspeich, F., and Zorbas H., supra.

Typically, the detection system is an optical detection system. In some embodiments, performing the method involves simple detection systems, which can be based on the measurement of parameters such as fluorescence, optical absorption, resonance transfer, and the like.

In further embodiments, detection systems are based on the comparison of the fluorescence intensities of spectrally excited nucleic acids labelled with fluorophores. Fluorescence is the capacity of particular molecules to emit their own light when excited by light of a particular wavelength resulting in a characteristic absorption and emission behavior. In particular, quantitative detection of fluorescence signals is performed by means of modified methods of fluorescence microscopy (for review see, e.g., Lichtman, J. W., and Conchello, J. A. (2005) *Nature Methods* 2, 910-919; Zimmermann, T. (2005) *Adv. Biochem. Eng. Biotechnol.* 95, 245-265, which is incorporated by reference in its entirety). Thereby, the signals resulting from light absorption and light emission, respectively, are separated by one or more filters and/or dichroites and imaged on suitable detectors. Data analysis is performed by means of digital image processing. Image processing can be achieved with several software packages well known in the art (such as Mathematica Digital Image Processing, EIKONA, or Image-PRO). Another suitable software for such purposes is the Iconoclust software (Clondiag Chip Technologies GmbH, Jena, Germany).

Suitable detection systems can be based on classical methods for measuring a fluorescent signal such as epifluorescence or darkfield fluorescence microscopy (reviewed, e.g., in: Lakowicz, J. R. (1999) *Principles of Fluorescence Spectroscopy,* $2^{nd}$ ed., Plenum Publishing Corp., NY, which is incorporated by reference in its entirety).

Another optical detection system that can be used is confocal fluorescence microscopy, wherein the object is illuminated in the focal plane of the lens via a point light source. Importantly, the point light source, object and point light detector are located on optically conjugated planes. Examples of such confocal systems are described in detail, for example, in Diaspro, A. (2002) *Confocal and 2-photon-microscopy: Foundations, Applications and Advances,* Wiley-Liss, Hobroken, N.J., which is incorporated by reference in its entirety. The fluorescence-optical system is usually a fluorescence microscope without an autofocus, for example a fluorescence microscope having a fixed focus.

Further fluorescence detection methods that can also be used include, inter alia, total internal fluorescence microscopy (see, e.g., Axelrod, D. (1999) *Surface fluorescence microscopy with evanescent illumination,* in: Lacey, A. (ed.) *Light Microscopy in Biology,* Oxford University Press, New York, 399-423), fluorescence lifetime imaging microscopy (see, for example, Dowling, K. et al. (1999) *J. Mod. Optics* 46, 199-209), fluorescence resonance energy transfer (FRET; see, for example, Periasamy, A. (2001) *J. Biomed. Optics* 6, 287-291), bioluminescence resonance energy transfer (BRET; see, e.g., Wilson, T., and Hastings, J. W. (1998) *Annu. Rev. Cell Dev. Biol.* 14, 197-230), and fluorescence correlation spectroscopy (see, e.g., Hess, S. T. et al. (2002) *Biochemistry* 41, 697-705); each of the above is incorporated by reference in its entirety.

In specific embodiments, detection is performed using FRET or BRET, which are based on the respective formation of fluorescence or bioluminescence quencher pairs. The use of FRET is also described, e.g., in Liu, B. et al. (2005) *Proc. Natl. Acad. Sci. USA* 102, 589-593; and Szollosi, J. et al. (2002) *J. Biotechnol.* 82, 251-266. The use of BRET is detailed, for example, in Prinz, A. et al. (2006) *Chembiochem.* 7, 1007-1012; and Xu, Y. et al. (1999) *Proc. Natl. Acad. Sci. USA* 96, 151-156; each of the above is incorporated by reference in its entirety.

Determining one or more values indicative of the presence and/or amount of the captured target nucleic acids can include time-dependent monitoring of the one or more indicative values obtained (i.e., the repeated performing of the determination/detection step and monitoring the course of the indicative value over time).

The step of providing the target nucleic acids can include releasing the target nucleic acids from biological material included in the sample. To this end, the sample can be heated in order to destroy cellular membranes and/or viral capsids (e.g., by employing a temperature control unit and/or temperature regulating unit as described below). In some embodiments, this releasing step includes contacting the fluid sample with a lysing reagent, for example a reagent including one or more detergents which disintegrate the cellular membranes and/or viral capsids. Such lysing reagents are well known in the art (see, for example, Sambrook, J. et al. (1989) *Molecular, Cloning: A Laboratory Manual,* 2nd ed., Cold Spring Harbor Laboratory Press, Cold Spring Harbor, N.Y.) and commercially available by many suppliers.

The method can further include separating the one or more target nucleic acids from concomitant material.

Providing the target nucleic acids can be performed spatially separated from the steps of contacting the complexes each including a target nucleic acid and a capture molecule with the binding member, subjecting the target nucleic acids to amplification, capturing the amplified target nucleic acids with respect to the binding member and determining a value indicative of the presence and/or amount of the captured target nucleic acids. E.g., the target nucleic acids can be provided in the same structure 502 in which the complexes each including a target nucleic acid and a capture molecule are formed.

In a further embodiment, the method is performed in a device as described above. For example, the device can include a first well 502 and the complexes each including a target nucleic acid and a capture molecule are formed in the first well 502. Further, the device can include a second well 512 and determining a value indicative of the presence and/or amount of the captured target nucleic acids can be performed in the second well 512 configured for detecting one or more target nucleic acids. The second well 512 can include a cover element covering the second well and an actuator unit adapted for being actuated to deform the cover element. Further, subjecting one or more target nucleic acids to amplification and/or recapturing the amplified target nucleic acids with respect to the binding member can also be performed in the second well 512.

Determining a value indicative of the presence and/or amount of the captured target nucleic acids can be performed with the actuator actuated to deform the cover element. In such an embodiment, the cover element can be deformed in such a way that the volume of the detection well 512 is reduced. Further, the volume of the second well can be re-increased after determining the value indicative of the presence and/or amount of the captured target nucleic acids.

According to another embodiment, a method is provided, including
a) providing an amount of a reporter compound; a first binding member being configured to bind an anchor group of a capture molecule; a second binding member capable of capturing the reporter compound; an amount of a target nucleic acid capable of forming complexes with the reporter compound; the forming of complexes with a reporter compound inhibiting capturing of the reporter compound by the second binding member; an amount of capture molecules wherein each capture molecule includes a binding portion specific to a region of the target nucleic acids and an anchor group;
b) forming complexes each including a target nucleic acid and a capture molecule;
c) contacting the complexes with the first binding member to bind the complexes to the first binding member;
d) releasing at least a subset of the amount of target nucleic acid from the first binding member;
e) forming complexes of a subset of the amount of a reporter compound with at least a subset of the amount of target nucleic acid;
f) capturing a remaining subset of the amount of reporter compound not in complex with a target nucleic acid on the second binding member; and
g) determining a value indicative of the presence and/or amount of reporter compound captured on the second binding member.

A reporter molecule or reporter compound can be any molecule that is capable of forming complexes with one or more target nucleic acids and that can be captured on a support member, e.g., the second binding member, wherein the forming of complexes with the target nucleic acids inhibits the capturing of the reporter compound on the support member, e.g., the second binding member. The term "capable of forming complexes" can refer to any interaction between a reporter molecules and a target nucleic acid. In other words, the term denotes the binding of the molecules to each other that can be accomplished via a common or different binding regions included in the reporter molecule that mediate the interaction with the target (such as via Watson-Crick base pairing between complementary nucleotide sequences). Typically, the interaction is reversible. Analogously, being captured on a support member or being captured on the second binding member includes any direct or indirect (for example, via capture molecules; see below) interaction of a reporter molecule with a given support member. This interaction is generally reversible as well.

In general, the reporter molecules can be nucleic acid molecules (i.e., RNA or DNA molecules as described above) having a length of 10 to 100 nucleotides, for example 15 to 50 nucleotides, 15 to 40 nucleotides or 20 to 30 nucleotides. Usually, the reporter molecules are single-stranded nucleic acid molecules (i.e., oligonucleotides). The reporter compound is configured such that the binding of such a reporter molecule to a target nucleic acid to be detected inhibits the capturing of the reporter molecule on the second binding member. The nucleic acid reporter molecules can include at least one specific binding region (herein also referred to as "interaction site") that is not only capable of interacting with the target nucleic acid (e.g., by binding to an at least partially complementary sequence region of the target nucleic acid, thus allowing, e.g., Watson-Crick base-pairing between the reporter molecule and the target nucleic acid to be detected), but also of being captured on the second binding member. Typically, the specific binding region included in the reporter molecule is at least 12 nucleotides in length, e.g., at least 15 nucleotides, at least 18 nucleotides or at least 22 nucleotides. In particular embodiments, the nucleotide sequence of the binding portion of the reporter molecules is complementary to the corresponding nucleotide sequence of the target nucleic acid.

One or more species of reporter molecules can be employed; in other words one or more different types of reporter molecules such as one or more nucleic acid molecules having different nucleotide sequences can be used.

A first binding member can be a binding member as described above. For example, a first binding member can refer to any solid matrix to which capture molecules, and thus also any complexes including such capture molecules, can be coupled via the anchor group of the capture molecules by covalent or non-covalent interactions. Examples of such matrices include, inter alia, synthetic particles such as magnetic beads (e.g., paramagnetic polystyrol beads, also known as Dynabeads®) and latex beads.

A second binding member can be a binding member as described above. For example, a second binding member refers to any solid matrix, on which the reporter molecules can be captured either directly (e.g., via an anchor group included in the reporter molecule) or in an indirect manner via one or more species of reporter specific capture molecules capable of capturing a reporter molecule to the second binding member by covalent or non-covalent interactions. Examples of second binding members that can be used include, inter alia, the substrates of array elements (e.g., microscope slides, wafers or ceramic materials).

A reporter specific capture molecule can be any molecule being included on (e.g., that attached to or immobilized on) the second binding member that shows a specific binding behavior and/or a characteristic reactivity, which makes it suitable for the formation of complexes with a reporter molecule (i.e., the binding to the reporter molecule). Nucleic acids are typically used as capture molecules. Examples of nucleic acids that can be used as reporter specific capture molecules include naturally occurring nucleic acids such as deoxyribonucleic acid (DNA) or ribonucleic acid (RNA) as well as nucleic acid analogs such as inter alia peptide nucleic acids (PNA) or locked nucleic acids (LNA). Specific examples of naturally occurring nucleic acids include DNA sequences such as genomic DNA or cDNA molecules as well as RNA sequences such as hnRNA, mRNA or rRNA molecules or the reverse complement nucleic acid sequences thereof. Such nucleic acids can be of any length and can be either single-stranded or double-stranded molecules. Typically, reporter specific capture molecules are single-stranded oligonucleotides having a length of 10 to 100 nucleotides, e.g., of 15 to 50 nucleotides or 20 to 30 nucleotides.

The reporter specific capture molecules can include at least one specific sequence region (i.e., the binding region), which is configured to bind a reporter molecule, for example, to interact with a complementary sequence region of a reporter molecule via base-pairing between the reporter specific capture molecules and the nucleic acid to be detected. Typically, the specific binding region is at least 12 nucleotides in length, e.g., at least 15 nucleotides, at least 18 nucleotides or at least 22 nucleotides. In particular embodiments, the nucleotide sequence of the binding region of the reporter specific capture molecules is complementary to the corresponding nucleotide sequence of the reporter molecule.

In some embodiments, at least a part of an interaction site of the reporter compound being capable of forming a complex with a target nucleic acid is also capable of forming a complex with a reporter specific capture molecule. In other words, the reporter specific capture molecules and the target nucleic acids compete for forming a complex with the reporter compound, that is, the respective binding regions included in the reporter specific capture molecules and the target nucleic acids recognize the same or at least similar corresponding sequence(s) of a reporter molecule. The term "similar sequences", as used herein, denotes sequences that differ only in one or more single nucleotide mismatches (i.e., non-complementary pairs of nucleotides) or by one or more single nucleotide addition, insertion or deletion (i.e., additional or lacking nucleotide residues). Thus, the respective binding regions included in the reporter specific capture molecules and the target nucleic acids are at least partially identical. The term "partially identical", as used herein, denotes sequences differing only in one or more single nucleotides, as described above, or sequences having overlapping binding sites, i.e., sequences sharing a common nucleotide sequence but differ in at least one other part of the sequence region. However, it is also possible that the respective binding regions included in the reporter specific capture molecules and the target nucleic acids recognize different, non-overlapping (e.g., adjacent) sequences of a reporter molecule but binding of either the reporter specific capture molecule or the target nucleic acid to the reporter molecule sterically interferes with the binding of the other one.

One or more species of reporter specific capture molecules can be employed; in other words, one or more different types of reporter specific capture molecules such as one or more nucleic acid molecules having different nucleotide sequences can be used. More than one species of reporter specific capture molecule concomitantly used are also referred to as library. Such libraries include at least two but can also include many more different molecules, e.g., at least 10 different species, at least 20 different species, at least 50 different species and so forth. The libraries can also be arranged on different locations with respect to the second binding member. For example, they can be present in form of arrays or any other spatial arrangement.

An array (or microarray) can be a defined spatial arrangement (layout) of capture molecules such as reporter specific capture molecules on a binding member, e.g., the second binding member (also referred to as substrate), where the position of each molecule in the array is determined separately. Typically, the microarray includes defined sites or predetermined regions (also called array elements or spots), which can be arranged in a particular pattern, where each array element typically includes only one species of capture molecules. The arrangement of the capture molecules such as reporter specific capture molecules on the support, e.g., the second binding member can be generated by means of covalent or non-covalent interactions. However, the capture molecules can also be directly immobilized within the reaction chamber of a device used for performing the method (see below).

Typically, the target nucleic acids are not subjected to the method in isolated form but in form of a sample that is suspected of including one or more species of target nucleic acids, i.e., one or more different types of nucleic acids such as molecules having different nucleotide sequences and/or molecules descending from different origins (e.g., nucleic acids derived from different pathogens infecting a host cell).

In some embodiments, the method further includes determining a value indicative of the presence and/or amount of target nucleic acid based on the value indicative of the presence and/or amount of reporter compound captured on the second binding member. That is, the presence and/or amount of the one or more target nucleic acids present in a particular sample can be calculated based on the difference between the presence and/or amount of reporter compound being present prior to the forming of target nucleic acid/reporter molecule complexes and the amount of reporter compound being captured on the second binding member after said complex formation.

For performing the detection reaction, the reporter compound can include one or more detectable labels as described above. In specific embodiments, the detectable labels are fluorescent labels. Numerous fluorescent labels are well established in the art and commercially available from different suppliers (see, for example, *The Handbook—A Guide to Fluorescent Probes and Labeling Technologies*, 10th ed. (2006), Molecular Probes, Invitrogen Corporation, Carlsbad, Calif., USA).

For detecting such labels, the device used for performing the method can further include a detection system suitable for determining values indicative of the presence and/or amount of reporter compound captured on the second binding member. E.g., a detection system suitable for determining values indicative of the presence and/or amount of target nucleic acids captured on a binding member as described above can be used.

In some embodiments, the method further includes releasing the remaining subset of the amount of reporter compound from the second binding member after the steps of forming complexes of a subset of the amount of reporter compound with at least a subset of the amount of target nucleic acid, capturing a remaining subset of the amount of reporter compound not in complex with a target nucleic acid on the second binding member, and determining the value indicative of the presence and/or amount of reporter compound captured on the second binding member.

In further embodiments, the steps of releasing, forming complexes, capturing, and determining are repeated N additional times, where N is an integer greater than or equal to 1. In other words, the method is performed in a cyclic manner. In specific embodiments, the integer N is ≥5, ≥10 or ≥20.

Further, the step of forming complexes of a subset of the amount of reporter compound with at least a subset of the amount of target nucleic acid and the step of capturing a remaining subset of the amount of reporter compound not in complex with a target nucleic acid on the second binding member can be performed concomitantly.

In particular embodiments, the method further includes subjecting the target nucleic acids to amplification, that is, to increase their amount present in the sample before subjecting the same to the further analysis in order to facilitate further detection. Typically, target nucleic acid amplification is achieved by means of a cyclic amplification. The cyclic amplification can include any number of amplification cycles that is equal or greater than two. Usually, cyclic amplification reaction includes at least 10 or at least 20 cycles.

An exemplary cyclic amplification is a polymerase chain reaction (PCR) as described above. Typically, PCR is used for the amplification of double-stranded DNA molecules by employing a thermostable DNA polymerase. In some embodiments, the DNA polymerase used in the cyclic amplification has exonuclease activity, particularly 5'→3' exonuclease activity. Examples of such DNA polymerases include inter alia Taq DNA polymerase or Tth DNA polymerase (which are commercially available from multiple providers). By means of this 5'→3' exonuclease activity the DNA polymerase can nucleolytically attack the labelled 5'-termini of reporter molecules that are bound to the target nucleic acids resulting in a progressive degradation of such reporter molecules. As a result, the amount of reporter compound that is captured on the second binding member additionally decreases during each cycle of the amplification reaction. Optionally, the DNA polymerase employed can also exhibit 3'→5' exonuclease activity ("proofreading activity") for removing an incorrect nucleotide that has been added to the nascent DNA strand at a particular sequence position. Examples of such DNA polymerases having both exonuclease activities include inter cilia Pwo DNA polymerase, and Pfu DNA polymerase (both enzymes are also commercially available from various suppliers).

If the target nucleic acid is a RNA molecule, the method can further include subjecting the target nucleic acid to reverse transcription as described above prior to subjecting them to amplification.

Amplification of the target nucleic acid can be initiated prior to the step of forming complexes of a subset of the amount of reporter compound with at least a subset of the amount of target nucleic acid. That is, the target nucleic acid is subjected to amplification while allowing reporter compounds to form a complex with a target nucleic acid, and reporter compounds not in complex with a target nucleic acid to be re-captured on the second binding member.

For nucleic acid amplification, a device 500 as illustrated in FIGS. 18 and 19 can be used for performing the method which can further include one or more temperature control units and/or temperature regulating units as described above for controlling and/or regulating the temperature within the structure or reaction chamber, e.g., the central well 502. Measuring the temperature in the reaction chamber can be performed as described above.

The detection/determination of a value indicative of the presence and/or amount of the target nucleic acids can be performed only once or more than once during the assay performed. In case, more than one detection step during a single assay is performed, in some embodiments the mean value of the results obtained can be calculated. The data obtained in one or more cycles of detection can be analyzed and mathematically processed using appropriate computer software known by persons skilled in the art in order to determine inter alia the presence, the length or the sequence of one or more target nucleic acids and/or to calculate its/their amount.

In some embodiments, particularly if the reporter compound is in excess of the target nucleic acid, the value indicative of the presence and/or amount of reporter compound captured on the second binding member is determined before the forming of complexes of a subset of the amount of reporter compound with at least a subset of the amount of target nucleic acid and the capturing of a remaining subset of the amount of reporter compound not in complex with a target nucleic acid on the second binding member are in chemical equilibrium. For example, the determination/detection step is performed during the annealing step of an amplification reaction. However, it is also possible to perform the determination/detection reaction after completion of the annealing step (i.e., during or after completion of the elongation step).

In a further embodiment, the value indicative of the presence and/or amount of reporter compound captured on the second binding member is determined 1 seconds to 120 seconds (e.g., 1, 5, 10, 15, 20, 30, 60 or 120 s) after initiating the steps of forming complexes of a subset of the amount of reporter compound with at least a subset of the amount of target nucleic acid and of capturing a remaining subset of the amount of reporter compound not in complex with a target nucleic acid on the second binding member.

In other embodiments, the value indicative of the presence and/or amount of reporter compound captured on the second binding member is determined after at least one cycle of the cyclic amplification including denaturation, annealing, and elongation steps, e.g., during or after completion of the annealing step. In specific embodiments, said value is determined after each cycle of the cyclic amplification. In other specific embodiments, the value indicative of the presence and/or amount of target nucleic acid is determined each time after determining the value indicative of the presence and/or amount of reporter compound captured on the second binding member.

In some embodiments, determining the value indicative of the presence and/or amount of reporter compound captured on the second binding member includes time-dependent monitoring of the indicative value (i.e., the repeated performing of the determination/detection step and monitoring the course of the indicative value over time).

In further embodiments, the value indicative of the presence and/or amount of target nucleic acid is determined based on a calibration curve correlating the value indicative of the presence and/or amount of reporter compound with the value indicative of the presence and/or amount of target nucleic acid.

The method can be performed in a device as described above including a structure adapted for accommodating liquids, wherein the structure includes at least one binding member and is in fluid communication with a microfluidic network; and a control unit adapted for controlling a fluid flow through the microfluidic network in such a manner that target molecules are captured at the at least one binding member, adapted for controlling an amplification of the target molecules in the structure, and adapted for controlling detection of compounds captured at the at least one binding member. For example, the method can be performed in a device including a rigid substrate; a flexible cover element at least partially covering the substrate; a first structure formed in the substrate, adapted for accommodating liquids and adapted for releasing contents of one or more cells, spores or viruses, the contents including target molecules; a second structure formed in the substrate, adapted for accommodating liquids and including at least one binding member adapted for capturing the target molecules and for determining a value indicative of the presence and/or amount of the target molecules; a microfluidic network interconnecting at least the first structure and the second structure; and an actuator unit adapted for effecting a fluid flow between the first structure and the second structure by pressing the flexible cover element against the substrate to selectively close a portion of the microfluidic network.

E.g., a device 500 can be used which includes a first well 502. In such an embodiment, the step of forming complexes each including a target nucleic acid and a capture molecule is performed in the first well.

The device 500 can include a second well 512. In such an embodiment, the first binding member and the second binding member are provided in the second well and the steps of contacting the complexes with the first binding member to bind the complexes to the first binding member; releasing at least a subset of the amount of target nucleic acid from the first binding member; forming complexes of a subset of the amount of a reporter compound with at least a subset of the amount of target nucleic acid; capturing a remaining subset of the amount of reporter compound not in complex with a target nucleic acid on the second binding member; and determining a value indicative of the presence and/or amount of reporter compound captured on the second binding member are performed in the second well.

According to another exemplary embodiment of the invention the method includes:

forming a composition of matter including:
- an amount of a reporter compound,
- a binding member capable of binding the reporter compound, and
- an amount of a target nucleic acid capable of binding the reporter compound, the binding of the target nucleic acid to the reporter compound inhibiting binding of the reporter compound to the binding member;

binding a subset of the amount of reporter compound with at least a subset of the amount of target nucleic acid;

binding a remaining subset of the amount of reporter compound not in complex with a target nucleic acid on the binding member; and determining a value indicative of the presence and/or amount of reporter compound bound to the binding member.

In a first step, the method can include forming a composition of matter including an amount of a reporter compound, a binding member, and an amount of a target nucleotide. The term "forming a composition", as used herein, denotes any combining or mixing of the components described above. This can be achieved by introducing the components either simultaneously, consecutively or separately into one or more reaction chambers of an analytical device suitable for performing the method. Alternatively, it is also possible to mix the individual components before introducing the mixture into the device.

As already described above, the method can also be performed with more than one reporter compound and more than one target nucleotide. Thus, in some embodiments, the step of forming a composition of matter includes forming a composition of matter including:

- an amount of a first reporter compound,
  - an amount of a first target nucleic acid capable of forming complexes with the first reporter compound, the forming of complexes with the first reporter compound inhibiting capturing of the first reporter compound by the binding member,
- an amount of a second reporter compound, and
  - an amount of a second target nucleic acid capable of forming complexes with the second reporter compound, the forming of complexes with the second reporter compound inhibiting capturing of the second reporter compound by the binding member.

The device can be any instrumentation suitable for assaying samples by means of the method. Typical devices for use in the method are described herein. Exemplary embodiments of such a device are illustrated in FIGS. 17A-D to 19. Further devices suitable for performing the method are described in the European patent application EP 06 122 695 and the international patent application WO 2007/051861, each of which is hereby incorporated by reference in its entirety.

In some embodiments, the reaction chamber can include two or more sub-chambers. This can be achieved by providing the first surface and/or the second surface with one or more partitions or cavities, which serve as lateral sidewalls between the two or more sub-chambers.

In a further embodiment, a device used in the method includes more than one reaction chamber in order to perform multiple assays of one sample in parallel or to perform different steps of an assay in a serial manner in different reaction chambers. To this end, the reaction chambers can be in fluid communication with each other. Fluid communication includes any interconnection between the individual reaction chambers, either directly or indirectly via an additional means such as a common sample introduction passage, filling unit, processing unit or the like. However, as used herein, the term does not necessarily mean that, after introducing a sample, the reaction chambers are in permanent fluid communication with each other. It is also possible that the reaction chambers are in transient fluid communication, for example achieved by unidirectional or bidirectional valves at the connections between the reaction chambers.

After forming the composition of matter, the method can include the step of forming complexes of a subset of the amount of reporter compound with at least a subset of the amount of target nucleic acid. In other words, the reporter molecules can be allowed to bind to the target nucleic acids, for example by forming double-stranded nucleic acid molecules via base pairing of complementary nucleotide sequences of the reporter compound and the target nucleic acid, respectively. The fact that a subset of the amount of reporter compound forms complexes with at least a subset of the amount of target nucleic acid present denotes that the total concentration of reporter molecules present at the beginning of the assay can exceed the total concentration of target nucleic acids present.

Subsequently, the remaining amount of reporter compound that is not in complex with a target nucleic acid can be captured (i.e., bound) on the binding member via the one or more binding regions included in the reporter molecule described above (either directly or by binding to capture molecules being attached to the binding member). Since the forming of complexes of the target nucleic acids with the reporter molecules inhibits the capturing of the reporter molecule on the binding member, the forming of target nucleic acid/reporter molecule complexes decreases the amount of reporter molecules that can be captured on the binding member as compared to the amount being present prior to performing the step of forming target nucleic acid/reporter molecule complexes.

Finally, the method can include determining a value indicative of the presence and/or amount of reporter compound captured on the binding member. Determining a value indicative of the presence and/or amount of reporter compound captured on the binding includes the detection/determination of parameters such as electrical conductivity, redox potential, optical absorption, fluorescence intensity or bioluminescence that allow for qualitative and/or quantitative measurements of the reporter molecules captured (or recaptured) on the binding member. Only one of these parameters can be determined but it is also possible to determine more than one parameter (e.g., electrical conductivity and the intensity of a fluorescence signal caused by a suitable label), either concomitantly or consecutively.

For performing the detection reaction, the reporter compound can include one or more detectable labels as described above, e.g., fluorescent labels. The detectable labels can be incorporated or attached to the reporter molecules, e.g., in form of modified and/or labelled ribonucleotides, deoxynucleotides or dideoxynucleotides.

For detecting such labels, the device used for performing the method can further include a detection system as described above suitable for determining values indicative of the presence and/or amount of reporter compound captured on a binding member, e.g., an optical detection system. The detection system can be connected to the reaction chamber. Typically, the detection system is positioned opposite to one of the at least one reaction chamber, optionally opposite to a particular surface region where detection takes place.

In some embodiments, the method further includes releasing the remaining subset of the amount of reporter compound from the binding member after the steps of forming complexes of a subset of the amount of reporter compound with at least a subset of the amount of target nucleic acid, capturing a remaining subset of the amount of reporter compound not in complex with a target nucleic acid on the binding member, and determining the value indicative of the presence and/or amount of reporter compound captured on the binding member. The term "releasing", as used herein, denotes the detachment or unbinding of the reporter molecules from the binding member. This can be accomplished, for example, enzymatically via the cleavage any covalent bonds or in cases, where the nucleic acid reporter molecules are bound to the binding member by nucleic acid capture molecules via complementary base-pairing, by increasing the temperature in the reaction chamber, in which the assay is performed, thus resulting in nucleic acid strand separation (i.e., denaturation).

In further embodiments, the steps of releasing, forming complexes, capturing, and determining are repeated N additional times, where N is an integer greater than or equal to 1. In other words, the method is performed in a cyclic manner. In specific embodiments, the integer N is ≥5, ≥10 or ≥20.

In some embodiments, prior to the step of forming complexes, the method further includes capturing at least a subset of the amount of reporter compound on the binding member; determining a value indicative of the presence and/or amount of reporter compound captured on the binding member; and releasing captured reporter compounds from the binding member. Thus, performing these additional steps enables the determination of the amount of reporter compound initially present before allowing the formation of complexes between receptor compound and target nucleic acid. Comparing the value obtained with that determined after capturing the subset of reporter compound not in complex with a target nucleic acid on the binding member provides a measure for the presence and/or amount of target nucleic acid present in a sample.

In particular embodiments, the method further includes subjecting the target nucleic acid to amplification, that is, to increase their amount present in the sample before subjecting the same to the further analysis in order to facilitate further detection. Typically, target nucleic acid amplification is achieved by means of a cyclic amplification. The cyclic amplification can include any number of amplification cycles that is equal or greater than two. Usually, cyclic amplification reaction includes at least 10 or at least 20 cycles. An exemplary cyclic amplification is a polymerase chain reaction (PCR) as described above.

The detection/determination of a value indicative of the presence and/or amount of the target nucleic acids can be performed only once or more than once during the assay performed. In case, more than one detection step during a single assay is performed, the mean value of the results obtained is calculated. The data obtained in one or more cycles of detection can be analyzed and mathematically processed using appropriate computer software known by persons skilled in the art in order to determine inter alia the presence, the length or the sequence of one or more target nucleic acids and/or to calculate its/their amount.

Referring to FIG. 1a, a method 100 for determination of molecular targets includes a lysing step 102 (for lysing a sample, for instance whole blood, in the presence of capture molecules with anchor groups), a complex formation step 110 (for forming a complex of HIV nucleic acids and capture probes with anchor groups, for instance hybridization), a capture step 114 (for capturing complexes onto a solid matrix, via anchor groups), a wash step 118 (for removing all unbound material, for instance nucleic acids, proteins, low molecular weight contaminants etc.), an amplification step 120 (for amplifying and labelling captured nucleic acids) and a detection step 126 (for detecting amplicons). According to method 100, polynucleotides are released from one or more target pathogens of a sample. Released polynucleotides that are associated with the target pathogens are captured at a surface. The captured polynucleotides are separated from concomitant materials (for instance, amplification inhibitors) of the sample. The separated captured polynucleotides are amplified to form amplicons. The presence of the polynucleotides is determined by detecting the amplicons. Because the amplified polynucleotides are associated with the target pathogens, the presence and/or identity of the one or more target pathogens can be determined (for instance, qualitatively and/or quantitatively). In an exemplary embodiment, method 100 includes determination of viral load based on a determination of one or more viruses present in a blood sample. Next, various steps of method 100 will be discussed.

In lysing step 102, polynucleotides 106 are released from pathogens present in a blood sample 104. Polynucleotides can be released from target pathogens as desired (for instance, thermally, chemically, mechanically, or by combination thereof). In an exemplary embodiment, polynucleotides are released by combining sample 104 with a lysing liquid that includes materials that lyse pathogens in the sample. Examples of liquids capable of lysing pathogens are found in Boom R., Sol C. J., Salimans M. M., Jansen C. L., Wertheim-van Dillen P. M., van der Noordaa J., Rapid And Simple Method For Purification Of Nucleic Acids, J. Clin. Microbiol. 1990 March; 28(3):495-503, which is incorporated herein by reference.

An exemplary lysing liquid includes one or more of a denaturant (for instance, guanidine thiocyanate (GuSCN) (for instance, about 4.57 M)), a pH buffer (for instance, Tris-HCl, (for instance, pH 6.4, 45 mM), a chelator (for instance, EDTA 20 mM), and a detergent (for instance, Triton X-100 1.2% (w/v) and/or saponin (for instance, 0.2%)), a salt (for instance, $MgCl_2$ (for instance, 75 mM) and/or $ZnCl_2$ (for instance, 1 mM)).

Lysing step 102 typically includes forming a mixture including released polynucleotides 106, concomitants of sample 104 (for instance, cellular components, amplification inhibitors, proteins, and other materials), and capture molecules 108i. Each capture molecule 108i includes a polynucleotide binding portion 109i and a biotin anchor group 111. Each polynucleotide binding portion 109i is a polynucleotide sequence complementary to (for instance, specific for) a different region of polynucleotide 106. For example, capture molecule 108a includes a binding portion 109a complementary to a target region 113 of polynucleotide 106 and capture molecule 108b includes a binding portion 109b complementary to a different target region 115 of polynucleotide 106. Typically, at least one (for instance, two or more, three or more, four or more) different capture molecules are used for each polynucleotide to be determined.

In some embodiments, polynucleotides 106 are released from target pathogens in the presence of capture molecules 108i. This can be accomplished by, for example, essentially simultaneously combining sample 104 with the capture molecules 108i and lysing liquid components. Sample 104 can be combined with the capture molecules 108i and components of the lysing liquid can be combined with the capture molecules 108i and lysing liquid components a liquid state or in a dried (for instance, lyophilized) state.

In alternative embodiments, polynucleotides are released from pathogens of sample 104 and the resulting mixture is combined with capture molecules 108i. For example, sample 104 and the lysing liquid components excluding capture molecules 108i can be combined and allowed to incubate for a period of time prior to combining the incubated mixture with capture molecules 108i.

In an exemplary embodiment, polynucleotides 106 are HIV-RNA and binding portions 109i of capture molecules 108i are complementary to regions thereof.

Turning to complex formation step 110, one or more capture molecules 108i combine with (for instance, hybridize with) polynucleotide 106 to form a complex 112. Complex formation step 110 can be performed by, for example, allowing released polynucleotides 106 to incubate for a period of time in the presence of capture molecules 108i sufficient to form complexes 112. In some embodiments, the incubation period is at least about 60 seconds (for instance, at least about 120 seconds, at least about 360 seconds). In some embodiments, the incubation period is about 600 seconds or less (for instance, about 480 seconds or less, about 420 seconds or less). In an exemplary embodiment, the incubation period is about 5 minutes.

For each polynucleotide to be determined, the total concentration of capture molecules 108i is typically sufficient to capture most (for instance, at least 60%, at least 75%, at least 90%, essentially all) of the polynucleotide in complexes 112. In some embodiments, the concentration of each of one or more (for instance, most or all) of capture molecules 108i is at least about 0.1 µM (for instance, at least about 0.25 µM, at least about 0.5 µM). The concentration in of each of one or more (for instance, most or all) of capture molecules is typically about 2 µM or less (for instance, about 1.5 µM or less, about 1 µM or less). In an exemplary embodiment, the concentration of each of one or more (for instance, most or all) of capture molecules is about 0.625 µM.

Turning to capture step 114, complexes 112 and capture particles 117 are combined to form capture complexes 119. Each capture complex 119 includes one or more complexes 112 and a capture particle 117. Complexes 112 are typically bound non-selectively to particle 117. Each capture particle 117 includes a streptavidin capture surface 116. Capture particles 117 capture each complex 112 by interaction between one or more biotin anchor groups 111 of capture molecules 108i and streptavidin capture surface 116. Exemplary capture particles 117 include streptavidin sepharose beads (Amersham) having a diameter of about 34 µm pre-washed with diH$_2$O to remove ethanol. Approximately 10,000 to 20,000 beads are used per assays, corresponding to a binding capacity of about 3 nmol of biotin per 10 µL of whole blood.

Typically, capture step 114 is initiated after incubating sample 104 with polynucleotides 106 and capture molecules 108i for a time sufficient to form complexes 112. For example, sample 104 can be incubated in the presence of the lysing liquid and capture molecules 108i prior to combining the resulting mixture with capture particles 117.

Typically, the total concentration of capture molecules 108i and particles 117 is sufficient to quantitatively capture each of one or more selected polynucleotides 106 associated with each of one or more target pathogens in sample 104. Thus, for each polynucleotide 106 to be determined, substantially all (for instance, at least 75%, at least 90%, at least 95%, at least 97.5%, or essentially all) of the polynucleotide is captured by capture molecules 108i and particles 117.

Turning to wash step 118, capture complexes 119 are separated from concomitant material (for instance, nucleic acids, proteins, cellular components, lysing reagents, and the like) not captured by particles 117. In some embodiments, capture complexes 119 are filtered using a filter with pores small enough to prevent passage of complexes 119 but large enough to permit passage of material not captured by particles 117.

Capture complexes 119 can be washed with a wash liquid to enhance separation of concomitant material. In some embodiments, at two or more different wash liquids are used. In some embodiments, a first wash liquid contains a detergent to remove low molecular weight substances, proteins and other cellular components adhering to the particles via hydrophobic interaction and a second wash liquid removes the detergent which might otherwise interfere with the subsequent amplification process. An exemplary first wash liquid includes 0.15 M LiCl, 0.1% SDS (since SDS is a PCR inhibitor, it can be removed prior to a PCR procedure), 10 mM Tris-HCl pH 8.0, and 1 mM EDTA). An exemplary second wash liquid includes 0.15 M LiCl, 10 mM Tris-HCl pH 8.0, 1 mM EDTA. Suitable wash liquids are described in, for example, U.S. Patent Application Publication No. 20040215011A1, which is incorporated by reference in its entirety.

Turning to amplification step 120, polynucleotides 106 are amplified using probes 122. Typically, the amplification is a PCR amplification. In an exemplary embodiment, polynucleotides 106 are RNA and the amplification is RT-PCR. In some embodiments, the pathogen is HIV.

Figure 1B:
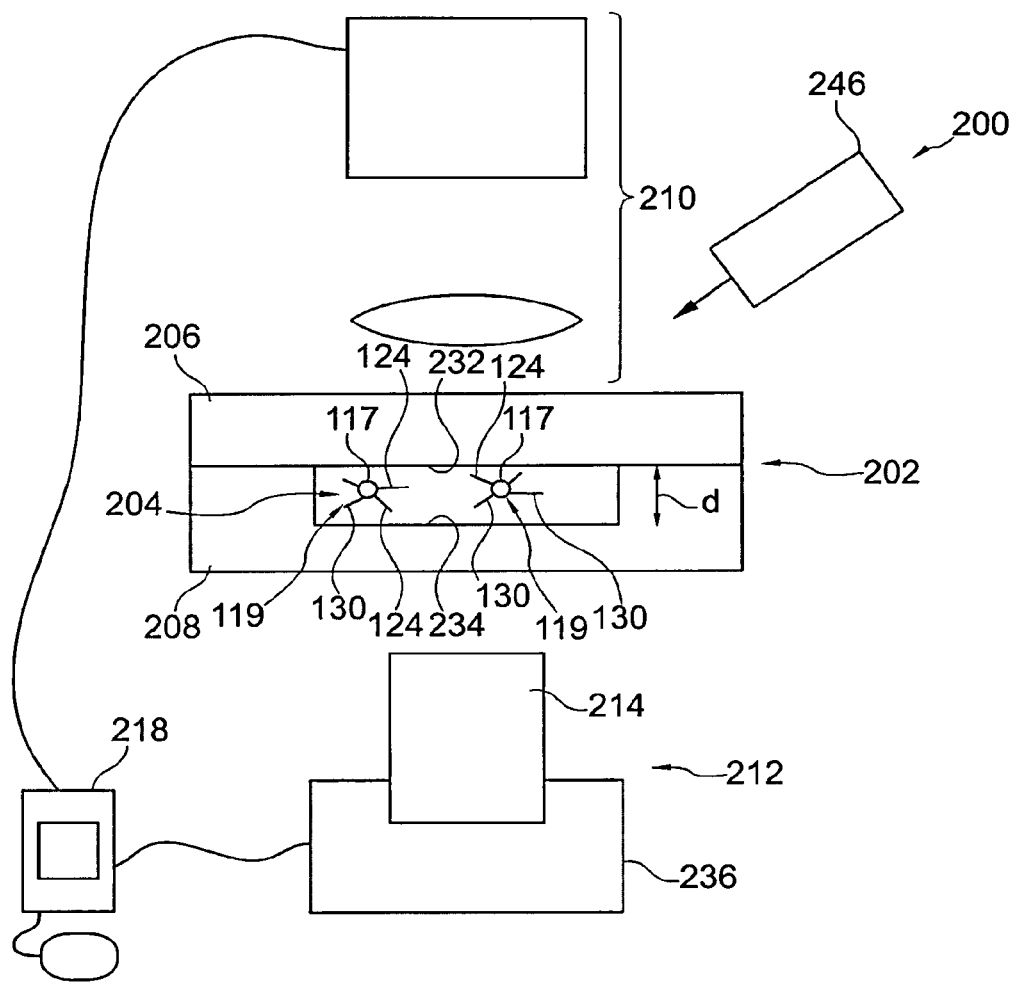
Figure 1C:
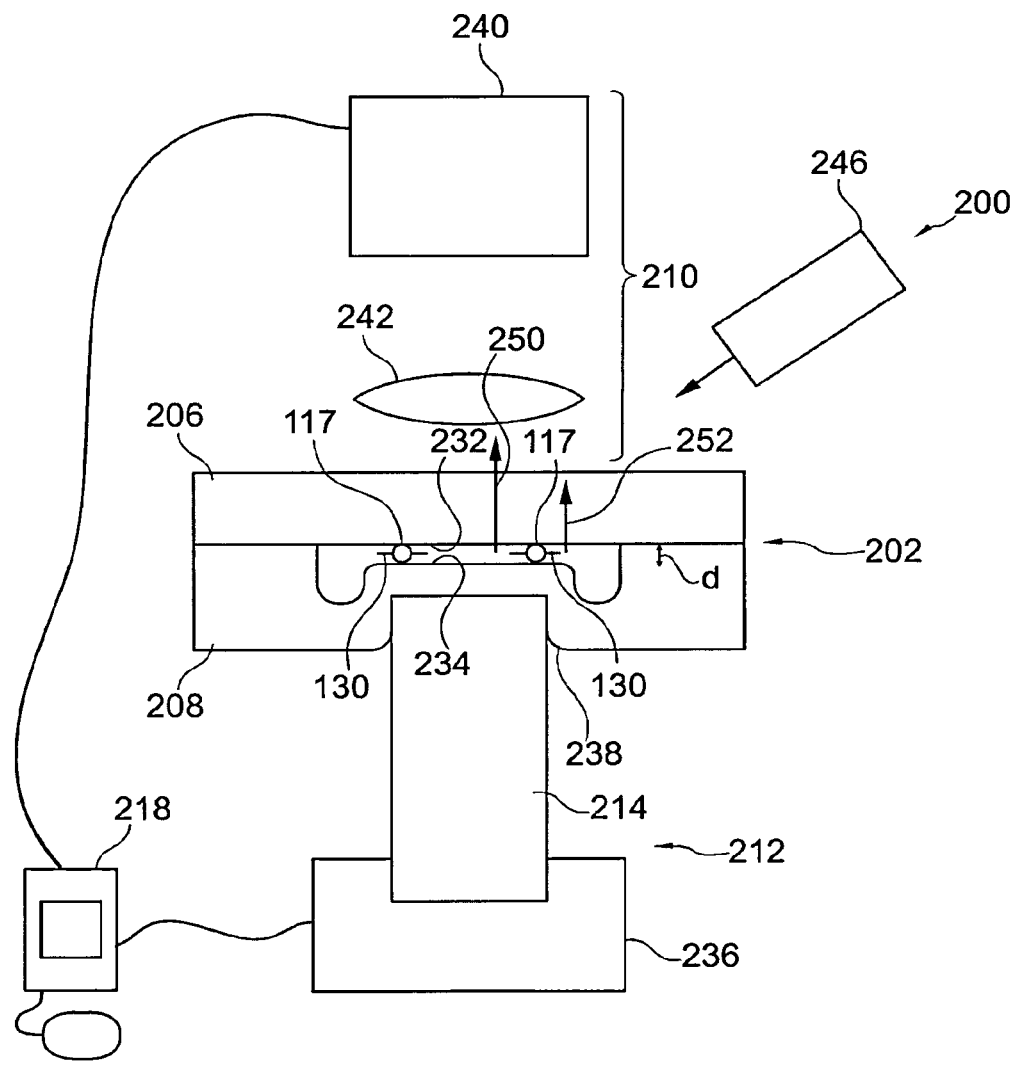
Figure 1D:
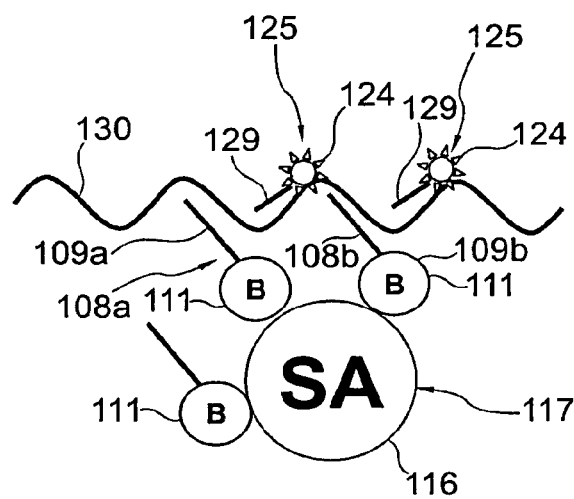
FIG. 1d shows an amplicon bound to a particle.

Referring to FIG. 1d, in some embodiments, amplification step 120 produces amplicons 130. Under hybridizing conditions (for instance, temperatures), amplicons 130 are captured by the immobilized capture probe molecules 108a, 108b and 108c at streptavidin surface 116 of particles 117. Amplicons are labelled with a fluorescent a labelling agent 125 including an optical label 124 (for instance, a fluorescent label) and a polynucleotide portion 129 complementary to a region of the amplicon 130.

Figure 1E:
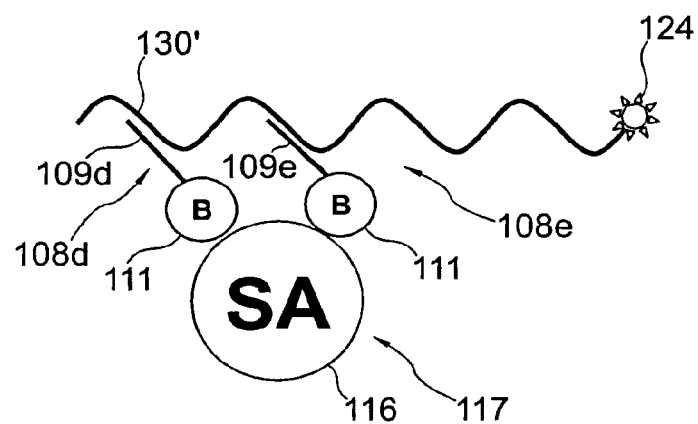
FIG. 1e shows an amplicon bound to a particle.

Referring to FIG. 1e, in an alternative embodiment, each probe 122 includes an optical label 124 (for instance, a fluorescent label). Other probes 108j include a polynucleotides portion 109j complementary to a region of amplicon 130 and also carry a biotin anchor group 111. Probe molecules 108j are captured to the streptavidin surface 116 of particles 117. Amplification step 124 produces directly labelled amplicons 130, each including a label 124. Amplicons 130 are captured by the immobilized probe molecules 108j onto the streptavidin surface 116 of particles 117. Binding portions 109j of probes 108j can be the same as, or different from, probes 108i used in capture step 114. Probes 108j and/or beads 117 can be combined with polynucleotides 106 along with other components used to perform amplification step 120.

In detection step 126, amplicons 130 are detected (for instance, by fluorescent detection of labels 111). Detection step 126 can be performed with amplicons 130 captured at streptavidin surface 116 of particles 117. Detection step 126 can be performed without first combining amplicons with a liquid free of probes 122. For example, detection step 126 can be performed with captured amplicons 130 present between first and second surfaces after reducing a distance the surfaces. An embodiment of this method for performing detection step 126 is discussed next with respect to FIG. 1b and FIG. 1c.

Referring to FIG. 1b and FIG. 1c, a system 200 for performing at least detection step 126 of method 100 includes a microfluidic cartridge 202, a detection system 210, a stencil actuator 212, and a processor 218, in communication with detection system 210 and actuator 212.

Cartridge 202 includes a first substrate 206 and a second substrate 208, which together define a detection chamber 204. First substrate 206 is typically optically transmissive (for instance, clear) with respect to a wavelength of light useful for exciting and detecting fluorescence from labels 124 of amplicons 130. First substrate 206 can be formed of, for example, a polymer, glass, or silica. Second substrate 208 is formed of a pliable or flexible material (for instance, an elastomeric polymer). First substrate 206 is generally less flexible than second substrate 208.

Actuator 212 includes a stencil 214 and a stencil driver 236 configured to drive stencil toward and away from second substrate 208. Stencil driver 236 can be actuated by, for example, compressed air, electromagnets, piezo electric or another suitable actuation. As seen in FIG. 1c, when actuated toward a wall 238 of second substrate 208, stencil 214 reduces a distance "d" between inner wall 232 of first substrate 206 and inner wall 234 of second substrate 208. In the reduced distance state of FIG. 1c, at least some capture particles 117 with captured amplicons 130 remain between surfaces 232, 234. In contrast, much of the liquid surrounding particles 117 is displaced from between surfaces 232, 234.

Detection system 210 is configured to detect the presence of amplicons 130 with cartridge 202 in the reduced distance state of FIG. 1c. Detection system 210 includes a light source 246 (for instance, a laser), an imaging detector 240, and an optical system 242. In use, light source 246 illuminates material present between inner surfaces 232, 234 of substrates 206, 208. Fluorescence 250 emitted from labels 124 from amplicons 130 is detected. The detected fluorescence 250 is indicative of the presence of amplicons 130. Processor 218 receives a signal from detection system 210 indicative of the detected fluorescence. Processor 218 can determine the presence of amplicons 130 and, therefore, the presence of the corresponding pathogens in sample 104.

In general, liquid remaining between inner surfaces 232, 234 emits background fluorescence 252 not associated with the presence of amplicons 130. The intensity of background fluorescence 252 is generally proportional to the amount of liquid remaining between inner surfaces 232, 234. The intensity of label fluorescence 250 from labels 124 of amplicons 130, however, is spatially localized in the vicinity of particles 117. Imaging detector 240 receives and detects both label fluorescence 250 and background fluorescence 252. However, because of the displacement of liquid from between inner surfaces 232, 234 in the reduced distance state of FIG. 1c, the signal-to-noise of label fluorescence 252 relative to background fluorescence 250 is higher than in the un-reduced state of FIG. 1b.

An exemplary embodiment of method 100 can be performed as follows. Between about 5 and 10 μL of capillary blood (for instance finger tip, earlap) is obtained from an individual. The blood sample is combined with about 90 μL of a lysis buffer including lysing components and capture molecules 108i. The resulting mixture is incubated with agitation for about 5 minutes at 21° C. The incubated mixture is combined with an amount of particles 117 equivalent to about 10 μL of slurry, corresponding to a binding capacity of 3 nmol biotin, i.e., particles are purchased as a slurry of particles in 20% ethanol). The mixture with particles is incubated with agitation for about 5 minutes at 21° C. After incubation, supernatant is removed by the stencil actuator system 350 for operating cartridge 300. The particles are washed with a first wash buffer (for instance, 3 times with 50 μl volume each time) and then with a second wash buffer (for instance, 3 times with 50 μl each time). After washing, the supernatant is removed. The washed particles are combined with an amplification medium and subjected to qRT-PCR amplification for detection (for instance, quantization) of captured polynucleotides 106.

Figure 14:
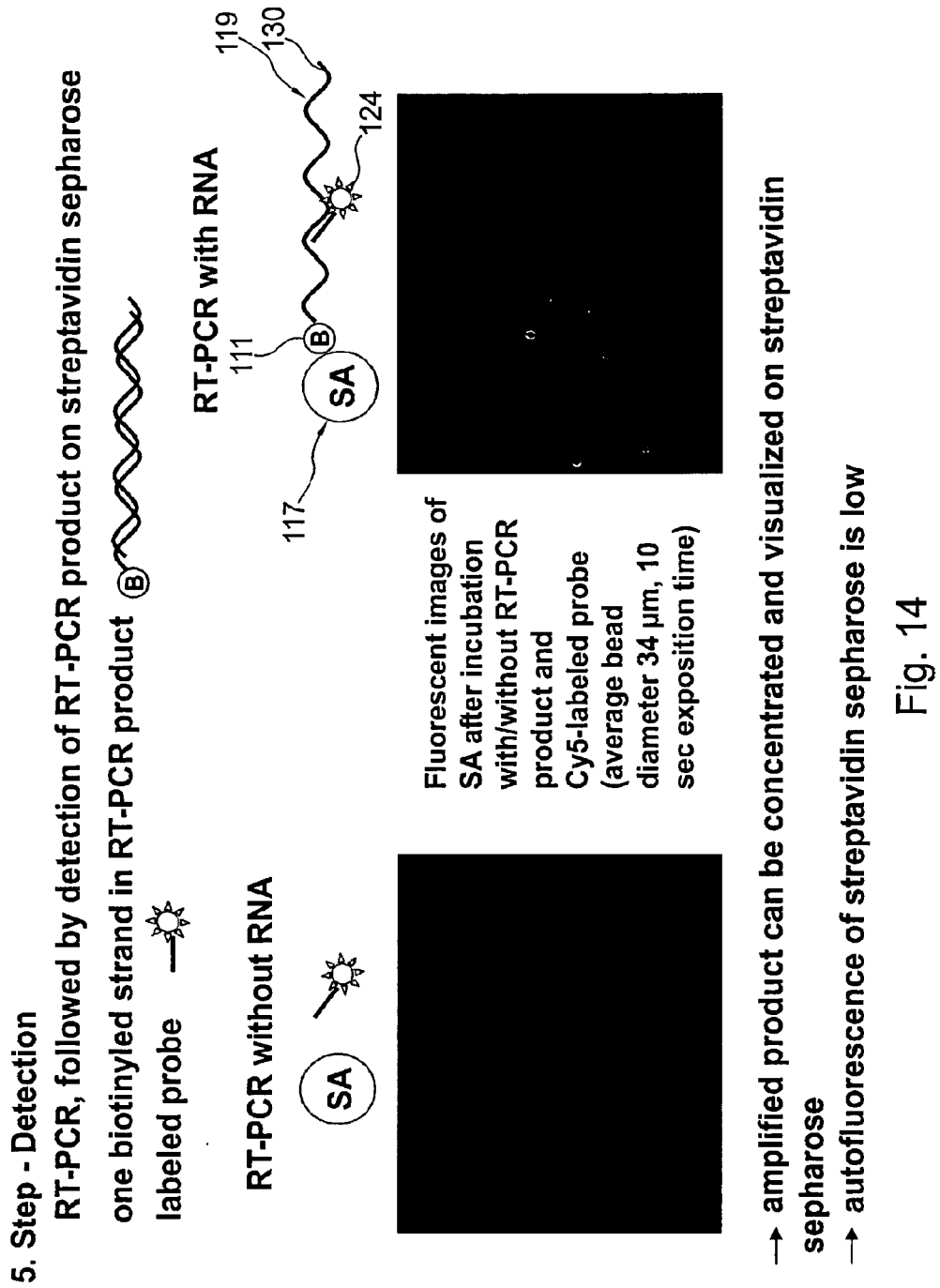
FIG. 14 shows fluorescent images of the detection of amplicons on strepavidin sepharose particles, wherein biotin-labelled amplicons were captured on strepavidin sepharose particles and visualized after hybridization of a fluorescently labelled probe to the captured amplicon.

Referring to FIG. 14, fluorescence from amplicons 130 is detected (for instance, using the reduced distance mode of an instrument such as that shown in FIG. 1b and FIG. 1c). Amplicons 130 can be detected after each of multiple different heating and cooling cycles of the amplification. In this way, the build up of amplicon concentration can be followed in time. Amplicons are typically detected while bound to particles 117.

While method 100 has been described as including a step of releasing polynucleotides from pathogens, method 100 can include other steps for providing polynucleotides. In some embodiments, polynucleotides are released from non-pathogenic cells (for instance, plant, human, animal, or the like). In some embodiments, the polynucleotides are products of a gene expression analysis. In some embodiments, polynucleotides are provided without requiring a releasing step and/or as polynucleotides already released from a cell or other biological sample.

Next, an embodiment of an assay system and a microfluidic cartridge will be discussed typically capable of performing most (for instance all) steps of method 100.

Figure 2:
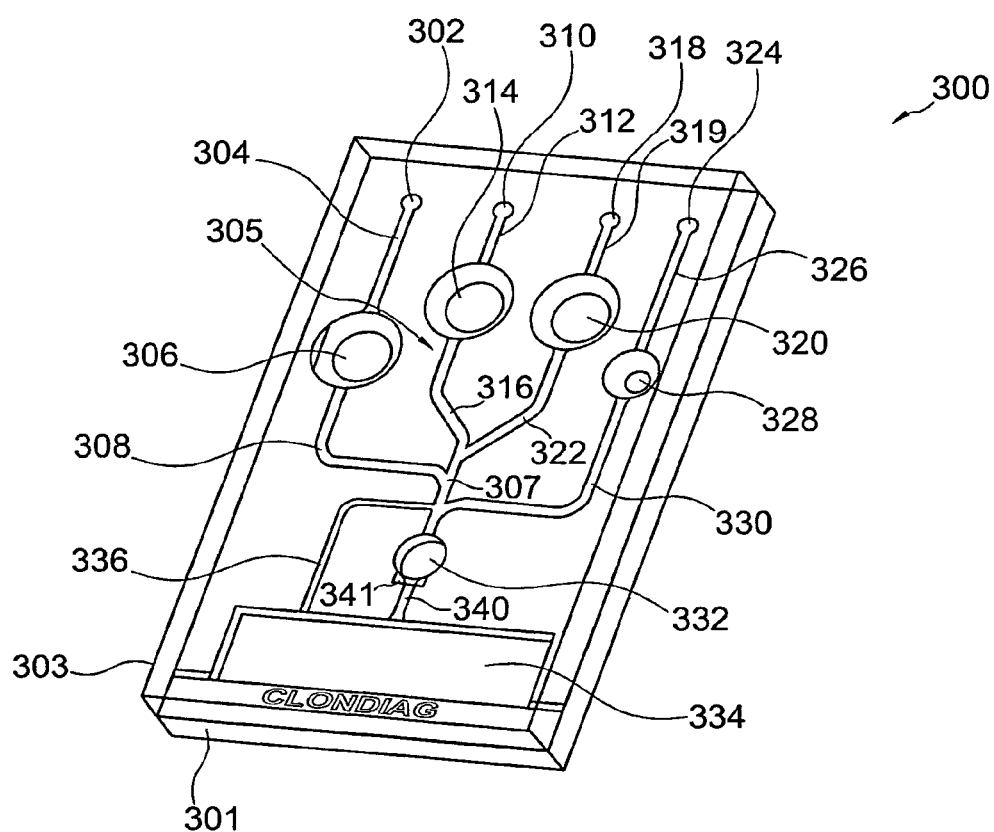
FIG. 2 illustrates an assay device suitable for use in the detection system of FIGS. 1b and 1c.

Referring to FIG. 2, a microfluidic cartridge 300 includes a first substrate 301, a second substrate 303 and a microfluidic network 305. First and second substrates 301, 303 can have properties similar to those described for substrates 206, 208 of cartridge 202.

Microfluidic network 305 is configured to receive a sample and various reagent materials, permit operations to be performed on these materials (for instance, mixing, transport, and incubation), and to facilitate detection of amplicons indicative of the presence of one or more target pathogens.

Microfluidic network 305 includes a sample inlet 302 connected by a channel 304 to a lysis chamber 306, which is connected by a channel 308 and a junction 307 to a detection chamber 332; a first liquid inlet 310 is connected by a channel 312 to a first reagent chamber 314, which is connected by a channel 316 to junction 307; a second liquid inlet 318 is connected by a channel 319 to a second reagent chamber 320, which is connected by a channel 322 to junction 307; and a third liquid inlet 324 is connected by a channel 326 to an amplification-labelling reagent chamber 328, which is connected by a channel 330 to junction 307. Junction 307 is connected to a waste chamber 334 via a waste channel 336. Detection chamber 332 is connected to waste chamber 334 via a waste channel 340, which includes a filter sized to prevent passage of particles 317 but to permit passage of un-captured material as described in wash step 118 of method 100.

Typically, reagent chambers 306, 314, 320, 328 include lyophilized reagents (for instance, as pellets) used to perform steps as described for method 100. In use, a liquid (for instance, water, buffer, aqueous solvent, or other liquid) is introduced to the inlet corresponding to a chamber. The liquid solubilises the lyophilized reagents to form a liquid. In an exemplary embodiment, lysis chamber 306 includes lyophilized reagents to facilitate lysing of target pathogens and capture molecules 308$i$ corresponding to polynucleotides of the pathogens. Typically, lyophilized reagents of chamber 306 are solubilised by the sample (for instance, a whole blood sample) alone or in combination with added liquid. In an exemplary embodiment, chamber 314 includes lyophilized reagents to form a wash liquid (for instance, a first wash liquid (buffer)) when combined with a liquid introduced to inlet 310. In an exemplary embodiment, chamber 320 includes lyophilized reagents to form a wash liquid (for instance, a second wash liquid (buffer)) when combined with a liquid introduced to inlet 318. In an exemplary embodiment, chamber 328 includes lyophilized reagents to form an amplification mixture (for instance, a second wash liquid (buffer)) when combined with a liquid introduced to inlet 324.

Prior to use of device 300, particles 116 are typically disposed within network 305 downstream of chamber 306. For example, particles 116 can be disposed within detection chamber 332 prior to use. Particles 116 can be washed with liquids from chambers 306,314,320,328 by appropriate actuation of stencils as discussed next.

Figure 3:
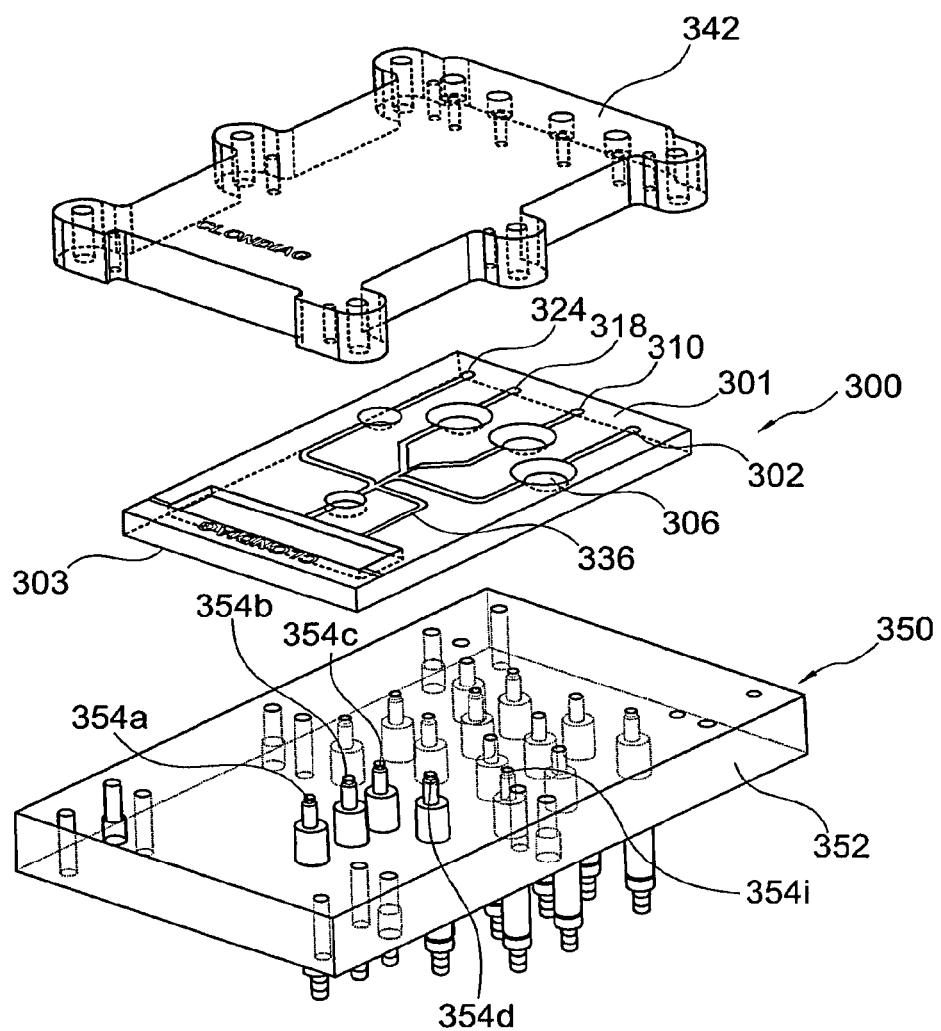
FIG. 3 is the assay device of FIG. 2 shown with a stencil actuator for operating the device.

Referring to FIG. 3, microfluidic cartridge 300 is shown in combination with a stencil actuator system 350 for operating cartridge 300. Actuator system 300 includes an actuator base 352 and multiple stencils 354$i$. Each stencil 354$i$ is actuated by a corresponding stencil driver similar to stencil driver 236. In use, cartridge 300 is positioned with flexible substrate 303 facing actuator base 352 and stencils 354$i$. Each stencil 354$i$ corresponds spatially to a different location of microfluidic network 305. For example, stencil 354$d$ corresponds to waste channel 336. When actuated, stencil 354$d$ compresses substrate 303 overlying channel 336 thereby obstructing channel 336 and preventing the passage of fluid there along.

Thus, the flexible property of the second substrate 303 or cover element ensures that it can be deformed in a reversible manner when a stencil 354$i$ exerts a mechanical force onto a dedicated portion of the flexible second substrate 303. In other words, if a reversible valve action is desired, the deformation of the second substrate 303 is reversible to that extent that when the force applied by the stencil 354$i$ is removed, the second substrate 303 returns towards its original position such that fluid can again pass along a corresponding channel 336.

In contrast to this, the rigid property of the first substrate 301 refers to the fact that the material of the first substrate 301 is configured in such a manner that, upon exertion of a force by a stencil 354$i$ onto the first substrate 301, no deformation of the first substrate 301 occurs which could have an influence on the valve function. Consequently, the second substrate 303 provides for flexibility, whereas the first substrate 301 provides for stability.

Other stencils correspond similarly to other channels of network 305. Stencils 354$a$, 354$c$ respectively correspond to waste channel 340 and junction 307. Actuation of stencils 354$a$, 354$c$ seals detection chamber 332 allowing multiple heating and cooling cycles to be performed without significant loss of liquid therein. Filter 341 permits particles 116 within chamber 332 to be washed with liquids from chambers 306,314,320,328 without loss of the particles. Still other stencils respectively correspond to chambers 306, 314, 320, 328, and 332. Repetitive actuation of these stencils can be used to agitate material (for instance, liquid) within the chambers to facilitate mixing (for instance, of samples and reagents). Sequential actuation of stencils along a channel can be used to move liquids along the channel. Contents of a chamber can be emptied by, for example, actuation of respective stencils operating upstream, downstream, and upon the chamber.

In one embodiment, the substrate is sufficiently reversible in that upon repeated stencil actuations and removals (e.g., at least ten actuations and removals, or at least fifty actuations and removals), the substrate returns toward its original position so that the portion of a microfluidic network underlying a particular stencil can be repeatedly obstructed and reopened.

Cartridge 300 can be operated as follows. An amount (for instance, between about 5-10 µL) of sample (for instance, whole blood) and an optional amount (for instance, between about 5 and 50 µL) of liquid (for instance, water) is introduced to chamber 306 network 305 via inlet 302. An amount of liquid (for instance, between about 20 and 200 µL) is introduced to chambers 314,320,328 via corresponding inlets. The respectively introduced sample and optional liquid resolublises lyophilized reagents present in chambers 306, 314, 320, 328. Stencils corresponding to each chamber are actuated to agitate the liquid reagent mixture therein to facilitate mixing. Within lysis chamber 306, the lysis buffer releases polynucleotides 106 from pathogens (for instance, as in lysing step 102). The released polynucleotides combine with capture molecules 108$i$ to form complexes 112 (for instance, as in complex formation step 110).

The lysing mixture of chamber 306 is moved to the detection chamber 332 and combined with particles 116 and incubated to form capture complexes 119 (for instance, as in capture step 114). The mixture within chamber 332 can be agitated for instance using a stencil. At the end of the capture step 114 incubation, liquid/supernatant is removed from detection chamber 332 to waste chamber 334 with the stencil actuator system 350 for operating cartridge 300.

After removal of liquid/supernatant from waste chamber 332, wash liquid from chambers 314, 320 is moved through chamber 332 to separate concomitants from complexes 119 (for instance, as in wash step 118). Chamber 332 can be agitated via stencil 354$b$ during washing.

After separating concomitants from complexes 119 within chamber 332, amplification reagents from chamber 328 are moved to detection chamber 332 and the resulting contents are subjected to multiple PCR cycles (for instance, as in amplification step 120).

After each of one or more amplification cycles, stencil 354$b$ is actuated to reduce a distance between opposed inner surfaces of detection chamber 332. Complexes 119, if present, remain trapped between the inner surfaces whereas other contents are relatively displaced as discussed with respect to device 200 in FIG. 1c. Detection is typically performed using a fluorescence detection system (for instance, as described for device 200). Detection is typically performed with amplicons 130 of complexes 112 in the hybridized state and bound to particles 117 as complexes 119 (for instance, as in detection step 126). After each cycle, the population of amplicons 130 increases. The fluorescence intensity resulting from capture complexes 119 increases accordingly. The fluorescence intensity increase with cycle number can be monitored to determine the threshold cycle at which the amplicons 130 can by quantitized. Because polynucleotides 106 are captured quantitatively (for instance, as in capture step 114), the quantitative detection of amplicons 130 permits the amount of polynucleotides 106 present in the sample to be determined quantitatively. Thus, for example, where the pathogen is a virus (for instance, HIV), the viral load within the sample (for instance, whole blood) can be determined.

Cartridge 300 can further include an array including multiple immobilized polynucleotides each corresponding to a polynucleotide sequence of a different pathogen subtype. After detection step 126, hybridization of amplicons 130 is performed to determine the pathogen subtype. In an exemplary embodiment, the array includes polynucleotides configured to determine a subtype of HIV.

While operation of cartridge 300 has been described as including the addition of liquid reagents, liquid reagents can be stored on the cartridge as in blister packs and released during use.

Other examples of systems suitable for optically determining the presence of label 124 are described in each of the following applications: the U.S. continuation of International Patent Application PCT/EP2005/004923, filed on Jan. 6, 2005, which designates the United States and claims priority to German Patent Application DE 10 2004 022 263, filed Jan. 6, 2004, the U.S. continuation having Ser. No. 11/593,021 and being filed Nov. 6, 2006, each of which is incorporated by reference in its entirety.

Next, referring to FIG. 4 to FIG. 16, various steps during an analysis procedure according to an exemplary embodiment will be explained.

Figure 4:
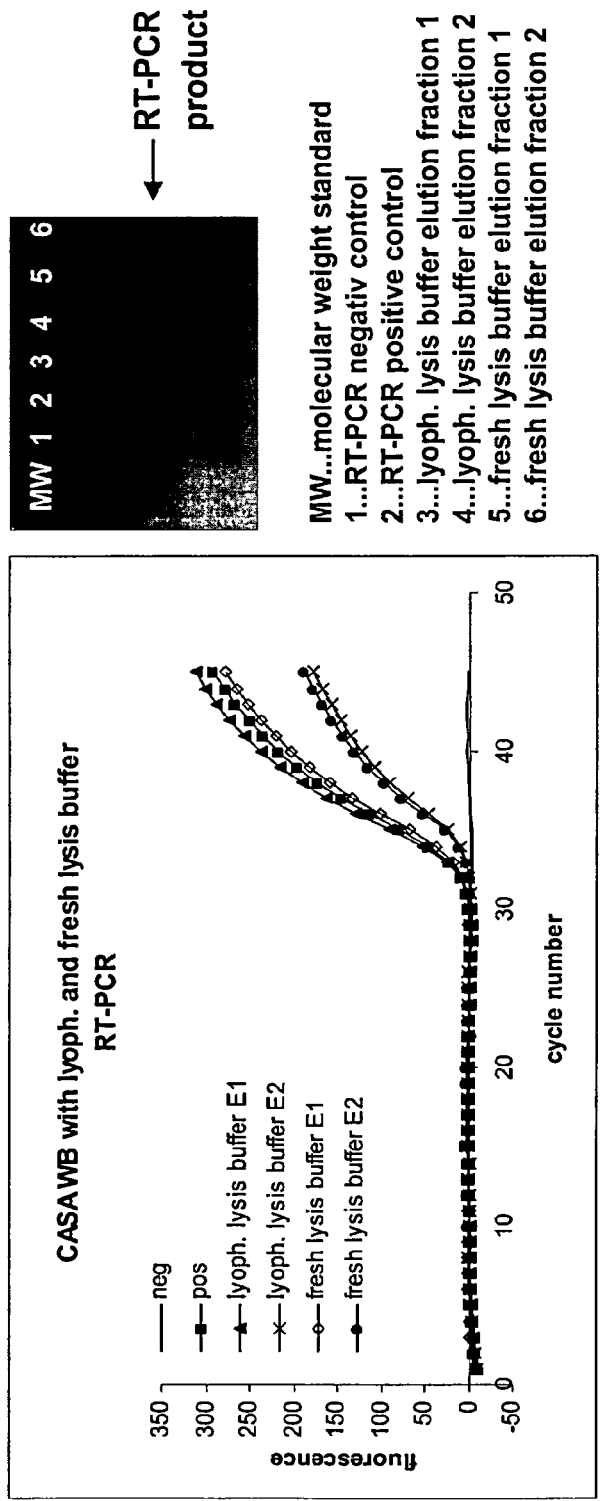
FIG. 4 shows the results (RT-PCR product curves and gel electrophoresis) of assays performed with either fresh or lyophilized lysis buffer, wherein the lysis buffer can be stored as lyophilized pellet without loss of function.
Figure 5:
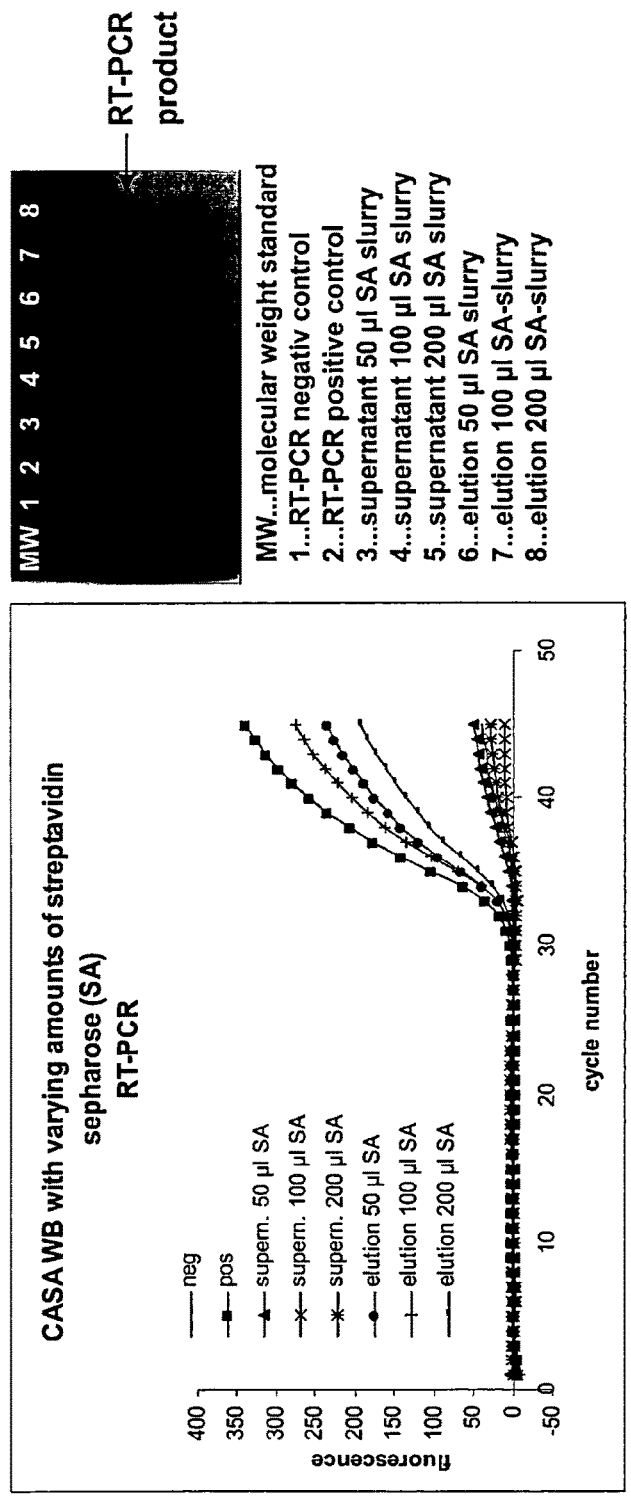
FIG. 5 shows the effect of the amount of streptavidin sepharose slurry used to capture an oligonucleotide (i.e., HIV RNA) from a blood-lysis mixture, wherein the results of assays performed with 200 µL, 100 µL, or 50 µL of streptavidin sepharose slurry reveal that binding capacity of 50 µL of slurry is sufficient to capture substantially all RNA molecules.
Figure 6:
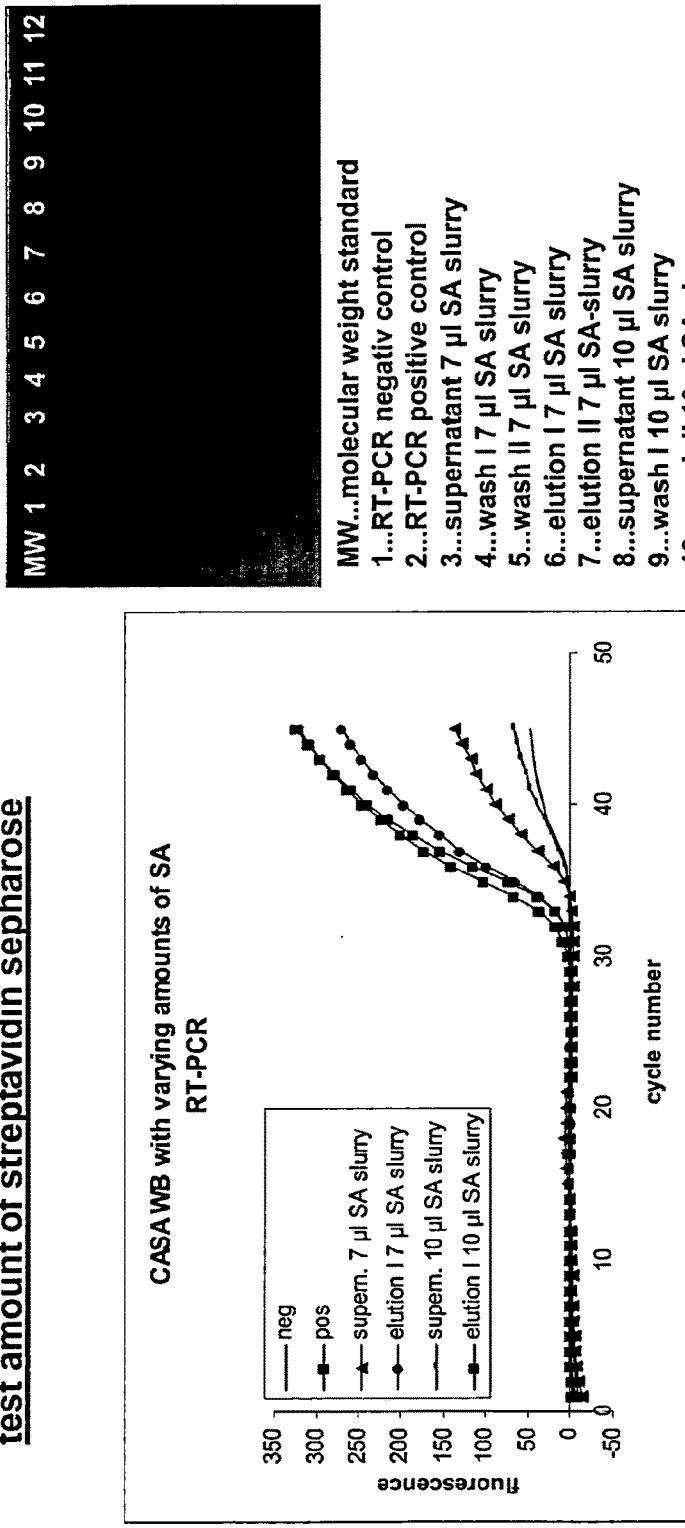
FIG. 6 shows the effect of the amount of streptavidin sepharose slurry used to capture an oligonucleotide (i.e., HIV RNA) from a blood-lysis mixture, wherein the results of assays performed with 10 µL and 7 µL of streptavidin sepharose slurry reveal that binding capacity of 10 µl of slurry is sufficient to capture substantially all RNA molecules.
Figure 7:
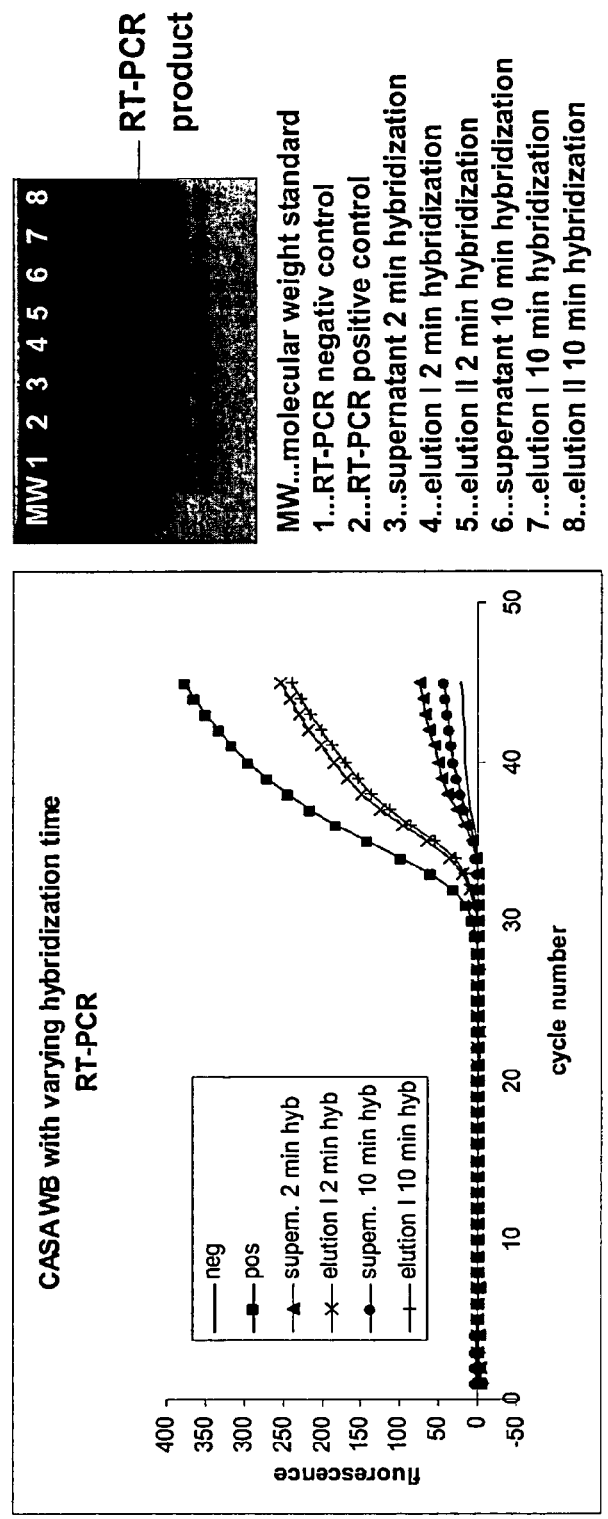
FIG. 7 shows the effect of the incubation time for the complex formation (i.e., hybridization) between the polynucleotide to be analyzed and the capture probes, wherein a substantial amount of polynucleotide is not recovered after 2 minutes of incubation time, while after 10 minutes of incubation no RNA can be detected in the supernatant.
Figure 8:
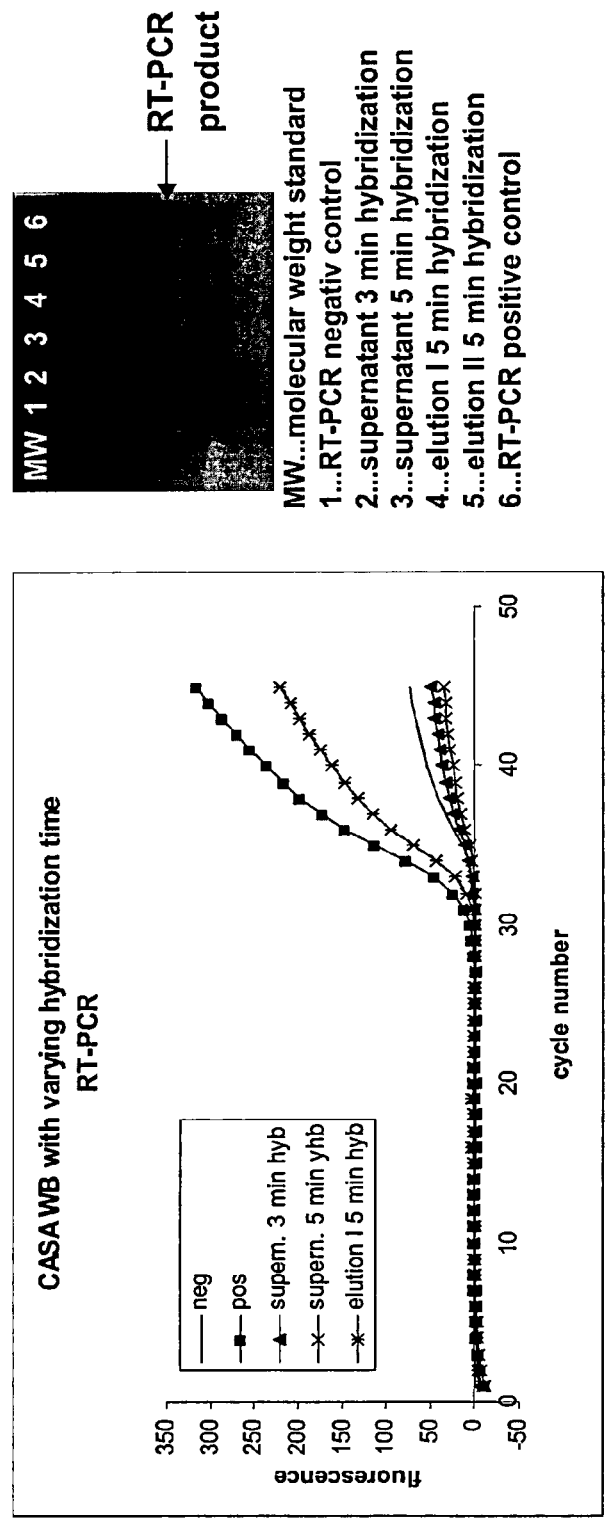
FIG. 8 shows the effect of the incubation time for the complex formation (i.e., hybridization) between the polynucleotide to be analysed and the capture probes.
Figure 9:
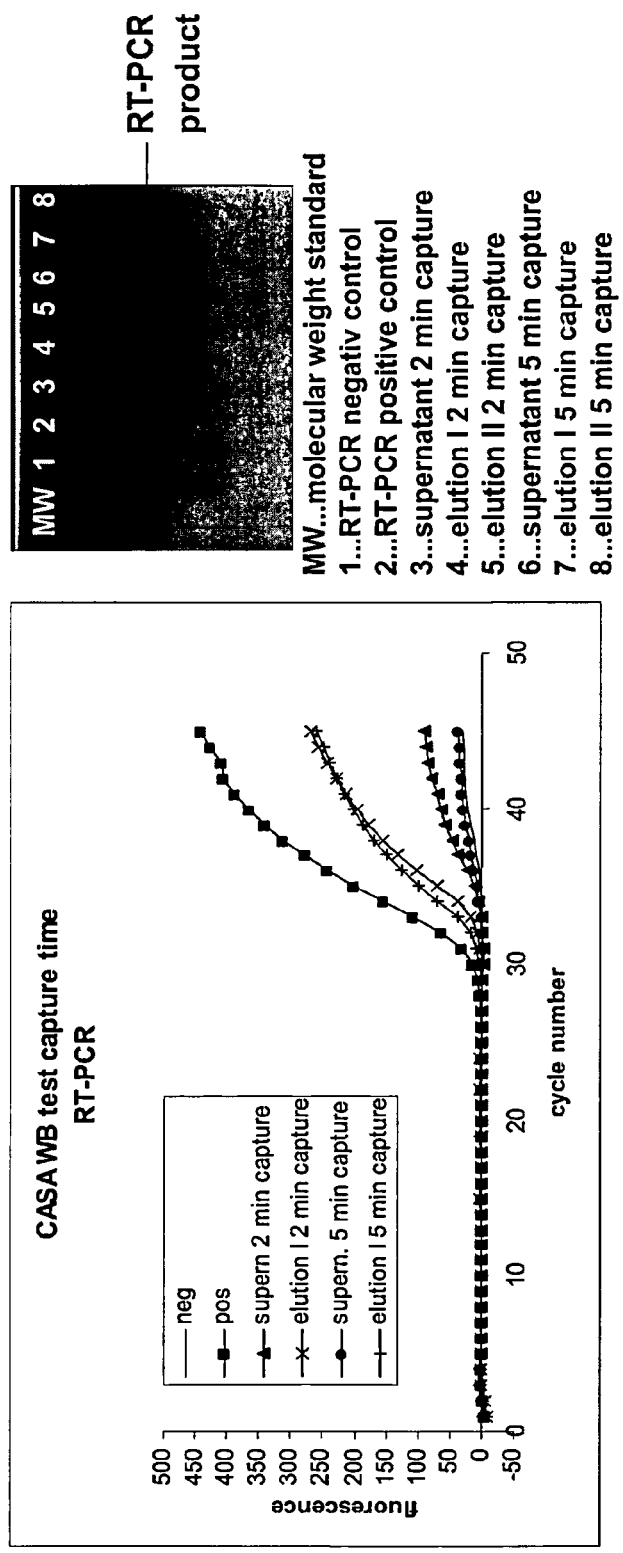
FIG. 9 shows the effect of the incubation time for the capture step (i.e., binding of the biotin anchor groups of the complexes to the streptavidin sepharose particles), wherein it is shown that 5 minutes of incubation time are sufficient to capture all polynucleotide molecules (i.e., no RNA molecules are detected in the supernatant).
Figure 10:
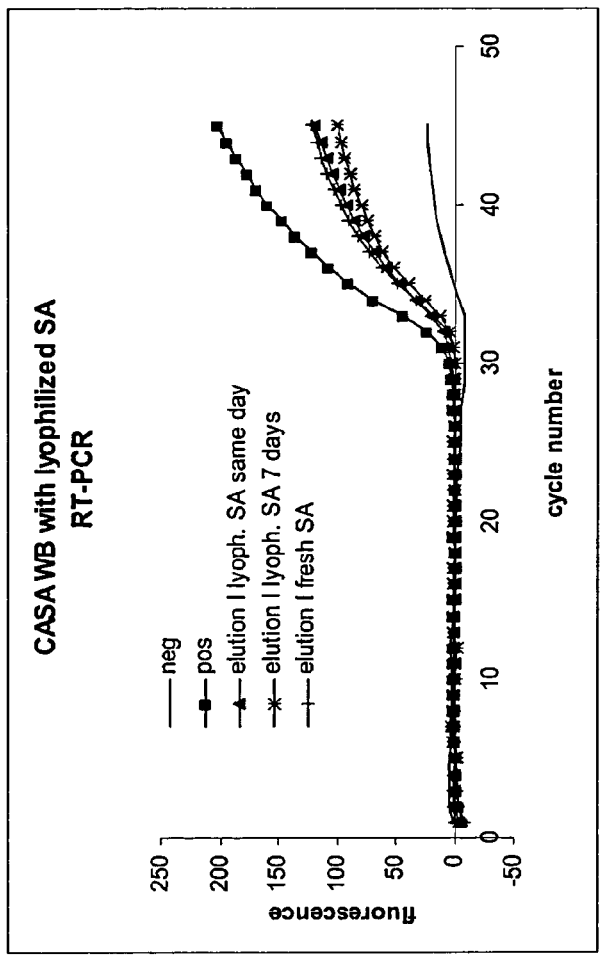
FIG. 10 show the results (RT-PCR product curves) of assays performed with either fresh or lyophilized strepavidin sepharose particles after storage of several hours or seven days, wherein the strepavidin sepharose particles can be lyophilized and reconstituted without loss of function.

FIG. 4 illustrates a lysis chamber.

FIG. 5 to FIG. 10 illustrate capturing of RNA complexes onto a solid matrix.

Figure 11:
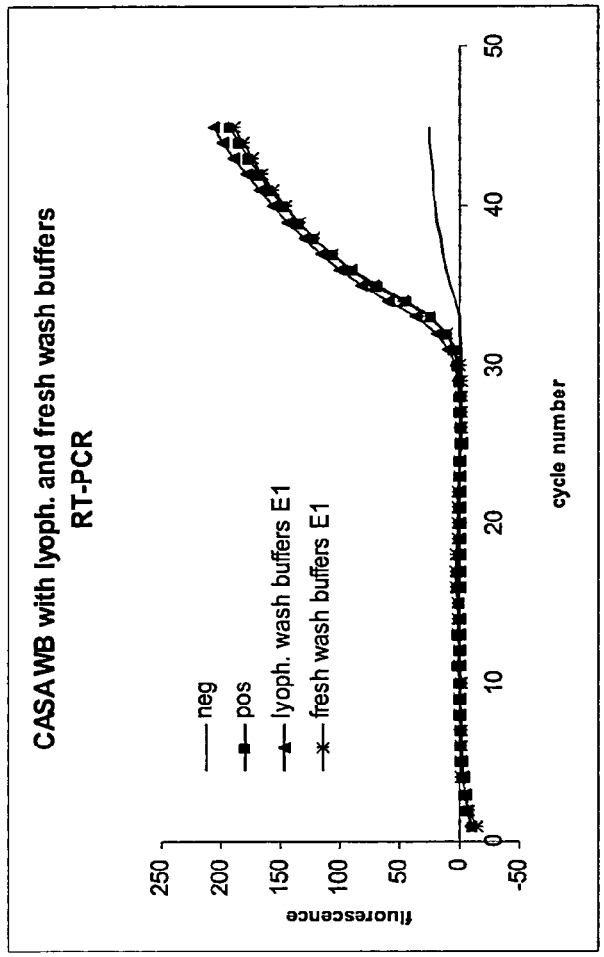
FIG. 11 show the results (RT-PCR product curves) of assays performed with either fresh or lyophilized wash buffers, wherein the wash buffers can be lyophilized and reconstituted without loss of function.

FIG. 11 illustrates washing.

Figure 12:
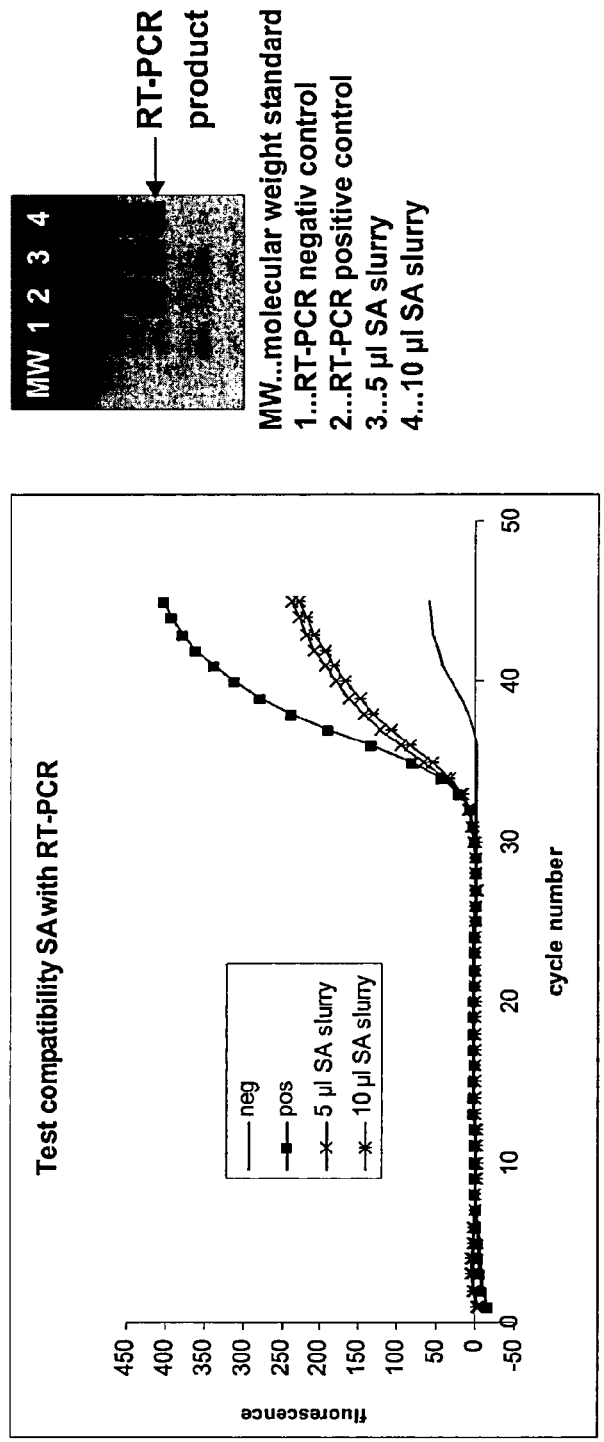
FIG. 12 show the results (RT-PCR product curves and agarose gel electrophoresis) of tests performed to show the compatibility of the strepavidin sepharose particles with RT-PCR, wherein 10 µl of strepavidin sepharose particle slurry can be applied to aRT-PCR amplification without loss of amplification efficiency.
Figure 13:
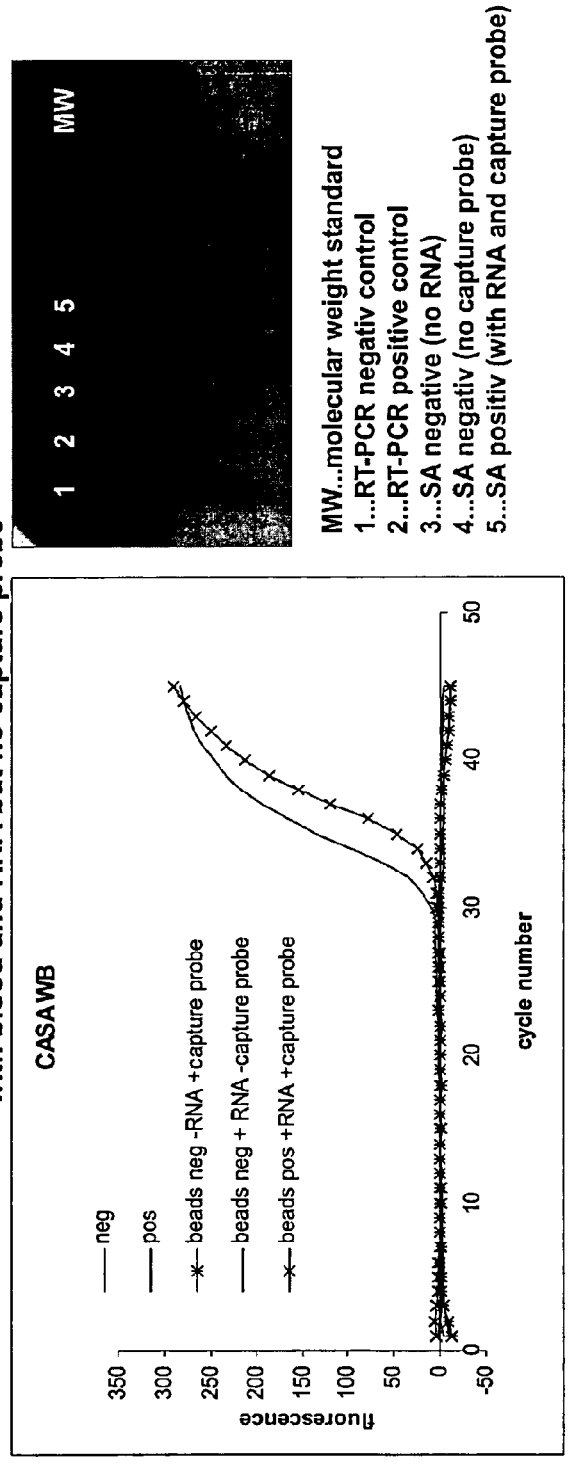
FIG. 13 shows the specificity of the assay according to an exemplary embodiment, wherein the results (RT-PCR product curves and agarose gel electrophoresis) show that neither the HIV-RNA binds non-specifically (i.e., in the absence of capture probes) to the strepavidin sepharose particles nor does any RNA of human blood cells which is also released during the lysis step is captured/amplified.

FIG. 12 and FIG. 13 illustrate amplification.

FIG. 14 to FIG. 16 illustrate detection.

Figure 17A:
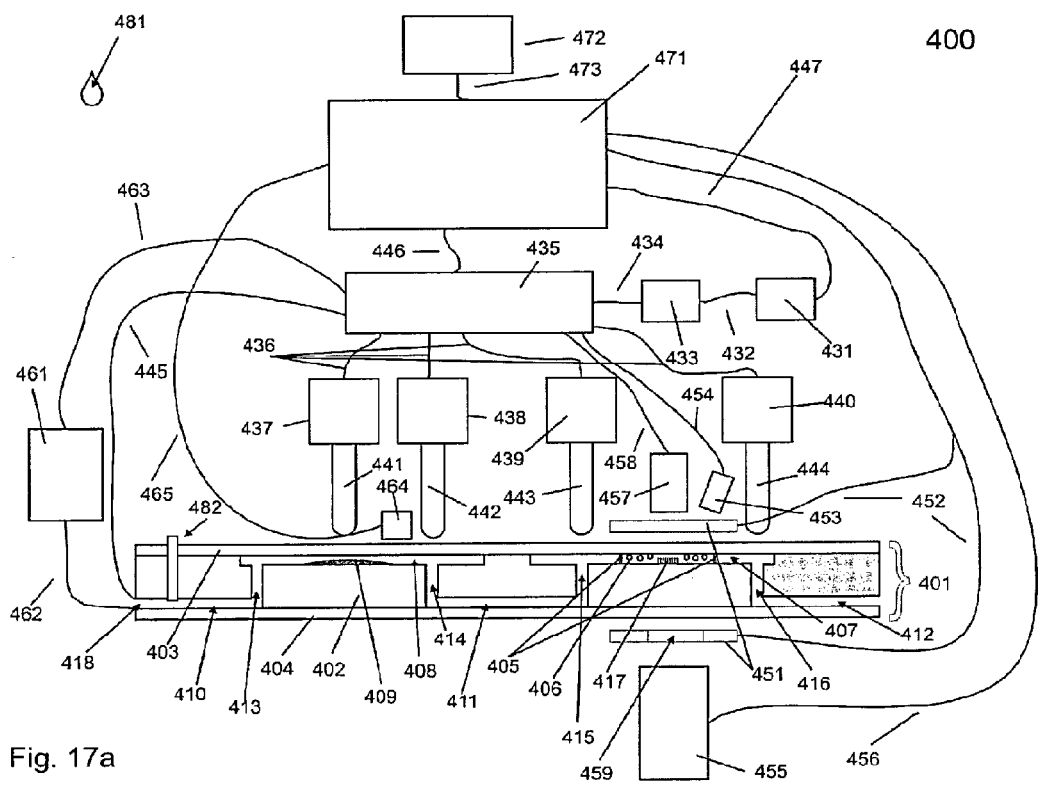
FIGS. 17A-D schematically illustrates a device.

FIG. 17a illustrates an exemplary system 400 for performing at least the steps of capturing targets from a sample, amplification of the target and detection of one or more values indicative of the presence of the target in the sample.

Figure 17B:
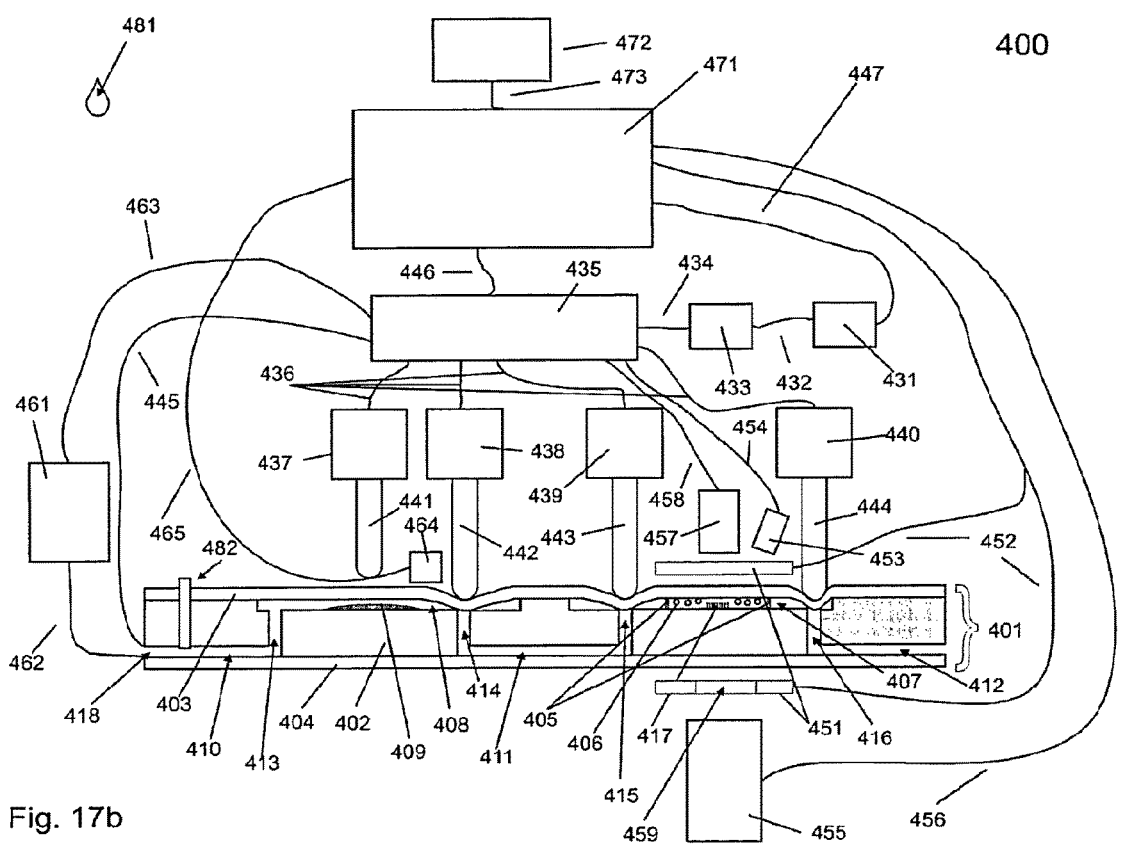

FIG. 17b illustrates an exemplary system 400 for performing at least the steps of capturing targets from a sample, amplification of the target and detection of one or more values indicative of the presence of the target in the sample in operated state.

Figure 17C:
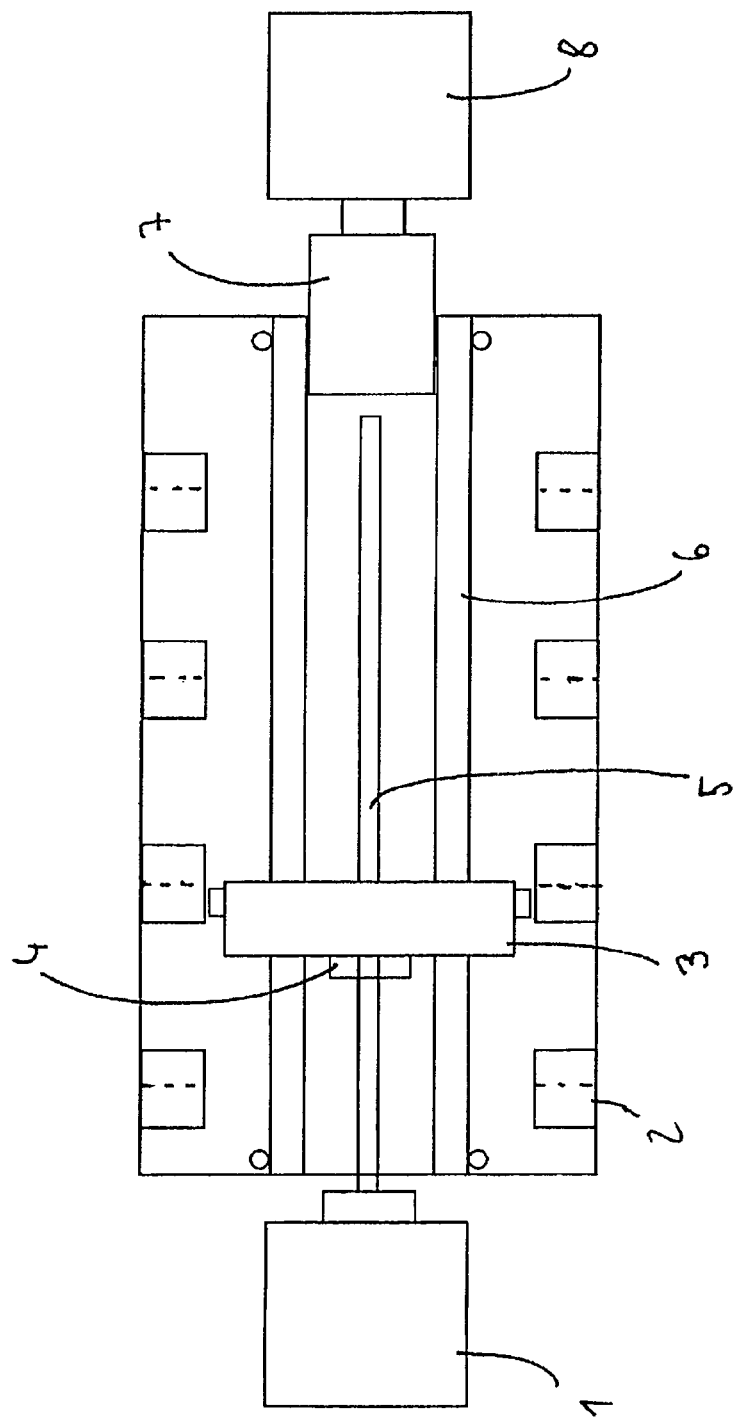

FIG. 17c illustrates an exemplary embodiment for valve unit 435 depicted in FIGS. 17a and 17b.

Figure 17D:
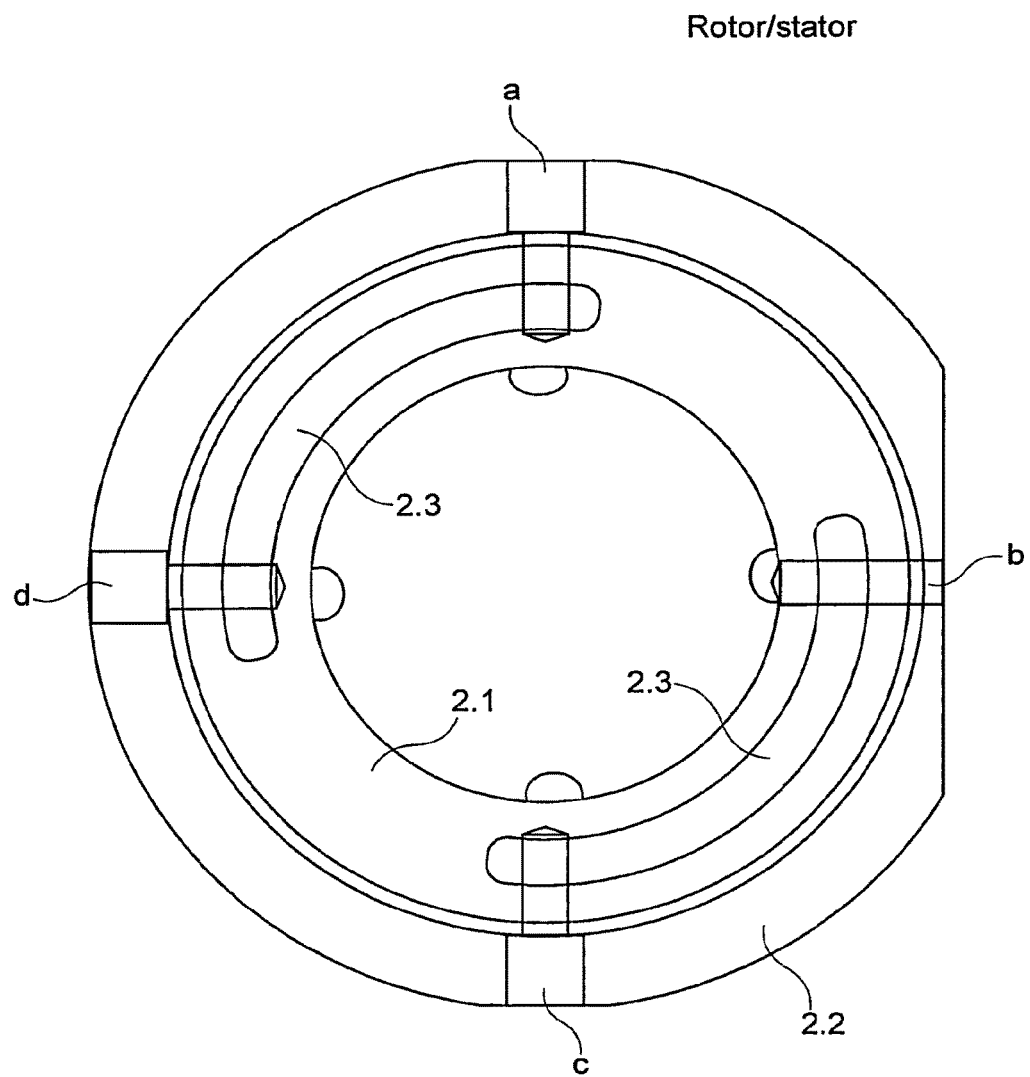

FIG. 17d illustrates an exemplary embodiment for valve 2 depicted in FIG. 17c.

Referring to FIGS. 17a and b, the exemplary system 400 includes a microfluidic cartridge 401, a detection system 455, a system for heating at least a part of the cartridge 451, actuator members 441-444 and actuators 437-440, a valve unit 435, a compressor 431, a liquid reservoir 461 and a processor 471.

Cartridge 401 includes a substrate 402 and a first cover element 403 which together define a first and a second well 408 and 407. The first cover element 403 is at least partially flexible to allow the cover element to be reversibly pressed towards substrate 402. The cartridge further includes a second cover element which defines together with substrate 402 channels 410, 411, 412. In some embodiments, the second cover element is also at least partially flexible. Channels and wells are interconnected by holes 413, 414, 415, 416 to form a microfluidic network.

In various embodiments, the substrate 402 can be any physical body made of any suitable material, such as plastics, glass, metal or a semiconductor. It can be any essentially planar (i.e., two-dimensional) or non-planar (i.e., three-dimensional) surface. An example for such a three-dimensional object is a physical body having a cavity or well including a reaction chamber (in which a biological, chemical or biochemical reaction can occur) including fluidic paths (like channels).

The first well 408 which can also be denoted as a lysis well is adapted for accommodating fluids and for releasing contents of cells, spores, or viruses, the contents including target molecules to be analyzed by the system 400. For example, the first well 408 can be adapted for releasing contents of cells, spores, or viruses by including lysing reagents 409 as described above. The lysing reagents 409 can be provided in dried form.

A second well 407 which also can be denoted as a central well is adapted for accommodating fluids and includes particles 406 as first binding members, the particles adapted for capturing target in complex with capture molecules and, optionally, a second binding member 417 adapted for capturing reporter molecules. The second well 407 further includes filter elements 405 to prevent passage of particles 406 but to permit passage of gases, liquids and substances solved in the liquids. Wells 407 and 408 are interconnected by channel 411 via through holes 415 and 414.

More generally, the first and second wells 408, 407 can be any structure, i.e., any physical entity which can serve as a carrier for receiving samples or substances. Particularly, such structures can include recesses such as grooves, wells or channels, or can also cover a material in which substances can be accommodated and through which the substances can be moved, such as gels.

In various embodiments, binding members include a component which is configured to bind molecules having a specific configuration. Such binding members can or can not be molecules immobilized on a surface. A binding capability can also result directly from a surface configuration (for instance a porous surface structure). It is also possible that binding members are provided as or on three-dimensional elements such as beads or a porous support. The surface of such a three-dimensional element or further molecules attached to the surface of the three-dimensional element, e.g., particles, can then serve as binding members. Different binding members being sensitive to different molecules can also be arranged (for instance in a matrix-like manner) on a surface of a structure. Examples for binding members are described above with respect to the various methods disclosed herein.

Volumes of the lysis well 408 and of the central well 407 can be 100 µL. In an exemplary embodiment, the width of the channels 410-412 is 200 µm, and a height of the channels 410-412 is 100 µm.

In various embodiments, such a microfluidic network can include one or more channels and/or wells, which can be interconnected to one another. For example, the various channels of such a microfluidic network can be bifurcated or branched to thereby allow for a transport of liquids through the microfluidic network along predefined paths (not shown).

The system 400 also includes an actuator system including actuator members 441, 442, 443, 444 driven by pneumatic actuators 437, 438, 439, 440, a valve unit 435, a compressor 431 and a reservoir for compressed air 433. Compressor 431 can constantly adjust a defined pressure in the reservoir for compressed air 433.

Each of the actuator members 441, 442, 443, 444 is actuated by a corresponding actuator. In use, cartridge 401 is positioned with the at least partially flexible cover element 403 facing the actuators and actuator members. Each actuator member corresponds spatially to a different location of microfluidic network of cartridge 401. For example, actuator member 442 corresponds to hole 414 leading to well 407 via channel 411 and hole 415. When actuated, actuator member 442 compresses the at least partially flexible cover 403 overlying hole 414 thereby obstructing hole 414 and preventing the passage of fluid there along. Other actuator members correspond similarly to other structures. E.g., actuator members 443 and 444 respectively correspond to holes 415 and 416. Actuation of actuator members 415, 416 seals second well 407 allowing e.g., multiple heating and cooling cycles to be performed without significant loss of liquid therein.

For exemplary actuation of actuator member 442 the control unit sends a signal to the valve unit. The valve unit opens the pneumatic connection 436 to actuator 438 thereby applying a pressure to the actuator 438. Thus, actuator member 442 moves out and compresses the at least partially flexible cover 403 overlying hole 414. To release the actuator member, the control unit sends a respective signal to the valve unit. The valve unit closes the pneumatic connection leading to actuator 438 thereby moving back the actuator member 442 and releasing the at least partially flexible cover 403 overlying hole 414.

The actuator member can be adapted to elastically deform the first flexible cover 403 to perform various tasks. For example, as described above actuator member 442 is adapted to compress the at least partially flexible cover 403 overlying hole 414 thereby obstructing hole 414 and preventing the passage of fluid there along while actuator member 441 is adapted to move a liquid within well 408 by repeatedly pressing and releasing the first flexible cover overlying well 408.

In one embodiment, an actuator member can be an element which is able to be moved to selectively open or close individual ones of the structures of the microfluidic network by mechanical forces. For example, such an actuator member can be a pin or a stencil which can be pressed against a flexible cover element to press the latter onto a surface of the substrate, thereby selectively opening or closing the channels.

In some embodiments, the tip of the actuator member 441, 442, 443, 444 is made of an elastic material such as silicone, gum or the like. The diameter of the actuator members 442, 443 and 444 maybe 1.5 times the diameter of holes 414, 415 and 416. A typical diameter for holes 414, 415 and 416 is 0.5 mm.

As described above, a pneumatic valve unit 435 is provided which is coupled to the actuators 437-440. The valve unit 435 receives drives signals from a control unit 471. Thus, the control unit 471 controls the operation of the actuator members 441-444.

The control unit 471 such as a microprocessor is provided and adapted for controlling an analysis of a fluidic sample in such a manner that target molecules of the fluidic samples are captured at the binding members 406. The control unit 471 further controls an amplification of the target molecules in the central well 407. Moreover, the control unit 471 controls a detection of compounds indicative of the presence and/or amount of the target molecules and captured at the binding members 417. All solid phase coupling procedures during an analysis of the target molecules occur at the binding members 406 in the central well 407. Particularly, no solid phase coupling procedures occur in the lysis well 408.

In an embodiment, a control unit can be an electronic component which is capable of controlling the function of one or more other components of the device, and which can particularly coordinate the function of the individual components. In the control unit, a code or an algorithm can be stored or can be user-defined in software, in hardware, or in hybrid form (i.e., including software and hardware components), in a manner to be capable of performing a specific analysis, experiment or assay. Particularly, such a control unit can include a processor having processing capability (optionally having also storage capability) and being configured to perform a specific experimental protocol. Particularly, such a control unit can be a microprocessor or a CPU (central processing unit).

The temperature of fluids in the central well 407 can be manipulated by a temperature manipulation unit including an pneumatic cooler 453, a temperature sensor (not shown) and a heating plate 451 arranged in vicinity of an upper surface of the substrate 402 and a second annular heating plate 451 having a central recess 459 to allow for an optical detection of molecules in the central well 407. In some embodiments, the heating plates include a temperature sensor for adjusting the temperature of the heating plates and/or of the second well. The control unit 471 can control the temperature distribution of the plates 451 to thereby manipulate the temperature of liquids in the central structure 407 (for instance in accordance with a temperature sequence for performing a polymerase chain reaction, to amplify target molecules during the analysis). Particularly, the temperature manipulation unit 451 has the capability to raise the temperature of the liquids located in the central well 407 up to 95° C.

Between the substrate 402 and the cover element 404, a fluid interface 418 is provided allowing inserting liquids such as water or buffers or gases such as air into the microfluidic system via channel 410 and hole 413. Another interface 482 can be provided which allows inserting a sample 481 into the microfluidic system.

In some embodiments, the substrate 402 is, at least partially, optically transparent to thereby allow for an optical radiation based detection of the components in the central well 407, as will be explained in the following.

A detector system 455 including an optical light source (not shown) such as a laser diode is adapted for generating an electromagnetic radiation beam impinging through the recess 459 in the second heating element 451 into the central chamber 407. In the presence of fluorescence markers in this chamber 407, a secondary electromagnetic light beam is generated which can propagate through the recess 459 in the second heating element 451 and can be detected by a detector (not shown) in the detector system 455 such as a photodiode. A detection signal of the detector system 455 indicative of the concentration of the target molecules can be provided to the control unit 471 for further processing via control unit interface 456. Thus, as can be taken from FIGS. 17A-D, the control unit 471 also coordinates the function of the detector system 455.

In some embodiments, during detection a detection actuator 457 compresses the central well to reduce the distance between the flexible cover elements 403 and 404 or between the flexible cover elements 403 and 404 and the substrate 402 thereby removing liquid including material which has not bound to one of the binding members 406 or 417 from the detection zone.

A liquid supply 461 is provided for pumping liquids such as water or buffers through the micro fluidic network formed by the wells 408, 407, by the through holes 413,414,415,416 and by the channels 410, 411, 412.

The transport of liquids through the device 400 can also be performed by sucking the liquid by a negative pressure (not shown). An optical sensor 464 can be provided to control the fluid level in chamber 408 as explained in the following. If well 408 is to be filled with liquid from liquid supply 461 the control unit 471 sends an according signal to valve unit 435 via interface 446. The valve unit opens a valve to apply pressure on liquid supply 461 via pneumatic connection 463 thereby pressing liquid from the liquid supply 461 into well 408 via liquid connection 462, channel 410 and hole 413.

When optical sensor 464 detects a signal indicative of the presence of the liquid in well 408, the sensor sends a signal to the control unit 471 via interface 465. The control unit 471 then sends a signal to valve unit 435. The valve unit closes the valve thereby stopping the pressure on liquid supply 461 thereby stopping the movement of the liquid out of well 408. Other optical sensors can be provided to control the liquid levels in other structures such as channels (410, 411, 412, sensors not shown) or wells (407, sensors not shown).

In various embodiments, the sample 481 can include any solid, liquid or gaseous substance, or a combination thereof. For instance, the substance can be a liquid or suspension, furthermore particularly a biological substance (such as blood, particularly whole blood). Such a substance can include proteins, polypeptides, nucleic acids, lipids, carbohydrates, viruses, bacteria, etc. In embodiments, a sample is a composition of matter possibly including a target.

As can be taken from FIG. 17A-D, the control unit 471 also controls the pump 431 via interface 447. A reservoir 433 for compressed air can be provided so as to harmonize the pumping procedure with the performance of the actuators 437-440, of the pneumatic cooler 453 and with the detection actuator 457.

The system 400 further includes a user interface unit 472 which can also be denoted as an input/output device. Via the user interface unit 472, a user can define an experiment run by the system 400. In other words, the user interface 472 can enable a user to program the system 400 so as to perform a specific assay. Such a user interface 472 can include a graphical user interface (GUI) having a display unit such as an LCD, a plasma device, or a cathode ray tube. Furthermore, input elements can be provided at the user interface 472 such as a keypad, joystick, buttons, a trackball or even a microphone of a voice recognition system. The user interface 472 is connected to the control unit via a data connection.

Referring to FIGS. 17*c* and *d*, in some embodiments the valve unit 435 consists of a number (n) of single valves (2). Each valve is made of a rotor (2.1) including channels (2.3) and a stator (2.2) both consecutive mounted and fixed with 4 springs to apply a constant pressure. Each valve has 4 holes (a, b, c, d), a is connected with the ventilation, b) is connected to the compressor, c) is connected with the pneumatic actuator and d) is connected to the ventilation site of the actuator.

The carrier (3) connected to a ball screw (4) that is placed inside the tube. A slot within the tube (6) enables the carrier to move. Rotation movement of the driving shaft (5) will result in a movement of the ball screw and the connected carrier in x-direction. That enables a movement of the carrier to the position of each valve (2). The carrier will lock into the rotor (2.1).

A 90° movement of the tube (6) will result in a 90° movement of the carrier (3) and rotor (2.1). The rotor and the pockets in the rotor disc will open or close the valve connections. (a,b and c,d; d,a and b,c).

In the following, referring to FIG. 18 and FIG. 19, a device 500 according to another exemplary embodiment will be explained. FIG. 18 shows a front view and FIG. 19 shows a back view of the device 500. The device 500 includes a groove 501, formed in a substrate 402, for inserting a cannula (not shown) via which a sample can be supplied to the device 500. A lysis chamber 502 is provided in which materials needed for lysing can be stored in a dried form. A central well 512 serves for performing all solid phase coupling procedures required for operating the device 500. Additional wells 504, 506, 508, and 510 are provided in which various further substances are provided in dried form and which can serve for washing procedures, a PCR procedure, etc. A waste chamber 514 is provided as a well in which liquids can be transported which are no longer needed for the analysis.

Although not shown in FIG. 18 and FIG. 19, a liquid absorbent material can be provided in the waste chamber 514 which can absorb fluids entering the waste chamber 514. By taking this measure, undesired back flow of liquids from the waste chamber 514 into other portions of the device 500 can be securely prevented to thereby avoid any contamination. For instance, swellable polymers (which can also be used in diapers) can be employed for such a purpose.

As can be taken particularly from FIG. 18, a plurality of fluid connection ports 520, 524, 521, 525, 540, 542, 544, 545, 548, 578, 580, 558, 562, 564, 560, 561, 552, 550, 516, 554, 530, 528, 532 and 526 are provided connecting various ones of channels, which will be explained in the following.

As can be taken from FIG. 19, additional fluid connection ports 541, 560, 566, 519, 512 are shown. Furthermore, a plurality of channels 538, 522, 518, 527, 529, 536, 572, 574, 576, 539, 562, 570, 546, 556, 568 and 534 are foreseen to connect the various fluid connection ports 520, 524, 521, 525, 540, 542, 544, 545, 548, 578, 580, 558, 562, 564, 560, 561, 552, 550, 516, 554, 530, 528, 532, 526, 541, 560, 566, 519 and wells 502, 504, 506, 508, 510 and 512. Beyond this, a fluid inlet port 593 is shown via which fluids such as water can be injected into the device 500. Via a fluid outlet port 594, fluid (such as air removed for reducing a pressure) can be removed from the device 500. A further fluid inlet/outlet port 597 is shown as well.

A first window portion 598 accessible by a light barrier and a second window portion 599 accessible by a light barrier are shown which can serve to detect optically when a meniscus of a fluid column within the device 500 passes transparent window portions 598, 599 related to the light barriers. When one of the light barriers detects that one of the chambers corresponding to the window portions 598, 599 is full with a liquid or overflows, this can be detected optically and can serve to generate a control signal for controlling a control unit (not shown in FIG. 18 and FIG. 19) to control the operation of the device 500 correspondingly.

When a first portion of a cannula is inserted into the groove 501, a second portion of the cannula can be inserted into a patient to take a blood sample from the patient and to directly inject the whole blood sample into the device 500.

Although not shown in FIG. 18 and FIG. 19, any one of the fluid connection ports 520, 524, 521, 525, 540, 542, 544, 545, 548, 578, 580, 558, 562, 564, 560, 561, 552, 550, 516, 554, 530, 528, 532, 526, 541, 560, 566, 519 can be covered by a flexible member which can be compressed by an actuator pin (not shown in FIG. 18 and FIG. 19) so that the pins can serve for selectively opening or closing any individual one of the fluid connection ports 520, 524, 521, 525, 540, 542, 544, 545, 548, 578, 580, 558, 562, 564, 560, 561, 552, 550, 516, 554, 530, 528, 532, 526, 541, 560, 566, 519, thus fulfilling a valve function.

Although not shown in FIG. 18 and FIG. 19, any one of the wells 502, 504, 506, 508, 510 and 512 can be covered by a flexible member which can be compressed by an actuator pin (not shown in FIG. 18 and FIG. 19) so that the pins can serve for selectively pressing on the wells 502, 504, 506, 508, 510 and 512, thus serving as mixers or pumps.

As can be taken from FIG. 18, a component 587 forming the central well 512 is a moulded plastic member which can be inserted into grooves 585, 583 of the substrate 402. This plastic member 587 can be patterned or structured from both sides so that components 590, 591, 578, 548, 580, 558, etc. are formed.

In the following, an assay performed in the device 500, particularly based on the central well 512, will be explained which can allow to perform a determination of HIV load in a fast manner, for instance in less than one hour.

Within the central chamber 512, beads can be provided. These beads can be configured to capture target molecules (for instance HIV RNA) from a previously lysed sample. E.g., the beads can be configured to bind an anchor group of a capture molecule to bind complexes including a target polynucleotide and the capture molecule, wherein the capture molecule includes a binding portion specific to a region of the target polynucleotide and the anchor group.

Reference numeral 541 denotes a connection to pressurized air (see arrow in FIG. 19) so that pressurized air can pass through elements 538, 518, 516 and will enter the well 502. Thus, it is possible to pump the well 502 empty using pressurized air. In case that a blood sample supplied via the groove 501 should be diluted with water, such water can be supplied via fluid inlet port 593.

In one embodiment, a whole blood sample (or any other sample) can be transported in the well 502, for instance for lysing. Blood can be soaked into the device 500 by first compressing the chamber, applying the blood to a capillary, the capillary in contact with the lysing chamber 502, then releasing the lysing chamber 502 thereby soaking the blood into the device 500.

For this purpose, the corresponding lysing agents as described above are provided in dried form in the lysis well 502. The lysis well can further include the capture molecules each including an anchor group and a binding portion specific to a region of the target polynucleotide. The sample which now can include complexes each including a target polynucleotide and a capture molecule can then be transported via components 554, 556 (via pressurized air) to the component 558. In this scenario, component 552 is closed by a corresponding actuator. Via components 558, 580, the sample can be transported into the central well 512. For this purpose, grooves 591, 590 of the central well 512 can be equipped with filters such as frits (not shown in FIG. 18 and FIG. 19) preventing beads in the central well 502 from being removed from this well 502 under the influence of the streaming force of the fluids. Thus, via the filter or frit in the grooves 591, 590, the lysed sample can be transported via component 576 into the central well 512.

In the central well 512, a first binding member such as beads or a surface functionalization can be provided so that targets or complexes including a target polynucleotide and a capture molecule can bind on solid capture structures in the central chamber 512. An incubation can be performed so that the beads properly mix with the sample material.

An air stream presses the liquid (i.e., non-captured components of the lysed sample) from the central well 512 via components 558, 560, 561 into the waste 514. Thus, many of the sample components which have not been captured by the beads in the central well 512 are transported into the waste chamber 514. Thus, only targets remain in the central well 512, and the remainder of the whole blood sample is now in the waste 514. Thus, the central well 512 now houses the beads together with complexes including capture probes and targets.

Subsequently, the central well 512 can be washed, wherein components for a wash buffer provided in a solid manner in a wash well 504 are used to produce a wash buffer. Such a washing procedure can be advantageous since, after the capturing procedure, some impurities can still be present in the chamber 502, particularly when a whole blood sample is used or the sample is supplied via a cannula inserted into the groove 501.

The wash liquid can be pumped, under the influence of air pressure, via components 541, 540, 542, 546, 548, 578, 591, 574, 512.

As already indicated above, a wash buffer is prepared in the wash well 504. In the wash well 504, salts for such a wash buffer can be present in dried form. For preparing the wash buffer, water can be transported from component 566 via components 564, 562, 570, 552 (while component 554 is closed), 527 (components 532, 525, 530 are closed), so that water is supplied to component 521 (open). Water can be pumped in the wash well 504 until a transparent window coupled to component 520 is filled with water, which can be detected by detecting a meniscus passing the light barrier adjacent the transparent window next to component 520. Upon receipt of a corresponding detection signal, the supply of water can be terminated.

An actuator (not shown) can then reciprocate upwardly and downwardly to compress a flexible cover element covering the wash well 504 to perform mixing to dissolve the salts provided therein.

Water filled channels can then be emptied by a corresponding control of the various valves and by supplying pressurized air, so that the water can be pumped into the waste chamber 514.

The prepared wash buffer in the wash well 504 can then be pressed into the central well 512 so that a washing procedure can be performed in the central well 512. After this washing, the wash solution can be pumped in the waste chamber 514.

Next, a reverse transcription can be performed to convert target RNA into a corresponding DNA. Such a procedure is specifically necessary in case of detecting Retroviridae such as HIV, and can be dispensable in other cases, for instance when DNA viruses are detected. To perform such a reverse transcription, components required for reverse transcription such as a primer, an enzyme and a buffer can be pumped from a reverse transcription well 508 into the central well 512.

Optionally, the components in the reverse transcription well 508 can also include another set of further capture molecules which can have the specific capability of capturing DNA molecules in the central well 512 produced during reverse transcription.

Since, after the reverse transcription, target DNA does not remain at the beads of the chamber 512, transporting the solution into the waste container 514 would reduce the amount of sample. For this purpose, the sample is now pumped from the central well 512 into the PCR well 510, and can dissolve the PCR salts within this sample, wherein the PCR buffer in the PCR well 510 can include polymerase, reporter molecules capable of forming complexes with the target polynucleotide, primer, and/or buffer. Alternatively, the reverse transcription buffer contains capture molecules directed to the synthesised DNA-Strands and capturing these strands takes place the same way like the initial capturing of HIV nucleic acids. After this, the sample can be pumped back into the central well 512.

However, the actual PCR amplification is then performed in the central well 512. For this purpose, a PCR is performed in the central well 512 by performing a temperature cycle, that is to say by repeating e.g., 40 times a procedure with 5 s at 95° C. and 10 s at 60° C. In another embodiment a temperature cycle including 3 or more different temperatures, e.g., including 30 cycles of 20 s at 95° C., 30 s at 55° C. and 30 seconds at 72° C., can be performed. However, other PCR cycling protocols can be performed in the central chamber, too.

In some embodiments, for adjusting the temperature in the central well 512 two heating plates can be provided above and below the central well 512. In another embodiment, one of the two heating wells can be continuous and the other one can have a recess to allow for a subsequent optical detection. In some embodiments, during the amplification the detection can take place as described above.

E.g., in a first embodiment, a competitive assay of capture molecules can be performed in the central well 512. Thus, in this embodiment, a first binding member such as beads are used for capturing the complexes each including a target molecule and a capture molecule, and a second binding member including an array of reporter specific capture molecules immobilized in the central well 512 is used for detection. The competitive assay includes forming complexes of a subset of the amount of reporter compound with at least a subset of the amount of target nucleic acid, the forming of these complexes inhibiting the capturing of the reporter compound by the array of reporter specific capture molecules immobilized in the central well 512. The reporter specific capture molecules immobilized in the central well 512 are capable of capturing at least a remaining subset of the amount of reporter compound not in complex with a target polynucleotide. By providing an array of different kinds of reporter specific capture molecules in the well 512 for detection, it is possible to distinguish between different types of the HI virus, for instance type 1 HIV and type 2 HIV, and it can be even possible to distinguish between different subtypes of the HI virus.

In a second embodiment, it is possible to use the same binding member, e.g., beads, which have already been used for the capturing procedure also for the detection. In this embodiment, a capture oligonucleotide being attached to the beads via an anchor group can hybridize with a complex of amplified target DNA, which itself can include a fluorescence label.

The captured reporter compounds or the captured target molecules can be detected by an optical detection for instance using the fluorescence label as described above. Particularly, an optical system having a light source (not shown) and a light detector (not shown) can be operated in a manner so as to measure the time dependence of the signal during the PCR, which allows deriving the viral load of HIV. In other words, the time dependence of the fluorescence signal can be acquired and evaluated.

In the following, referring to FIG. 20, a device 600 according to an exemplary embodiment will be explained.

Figures 20, 21:
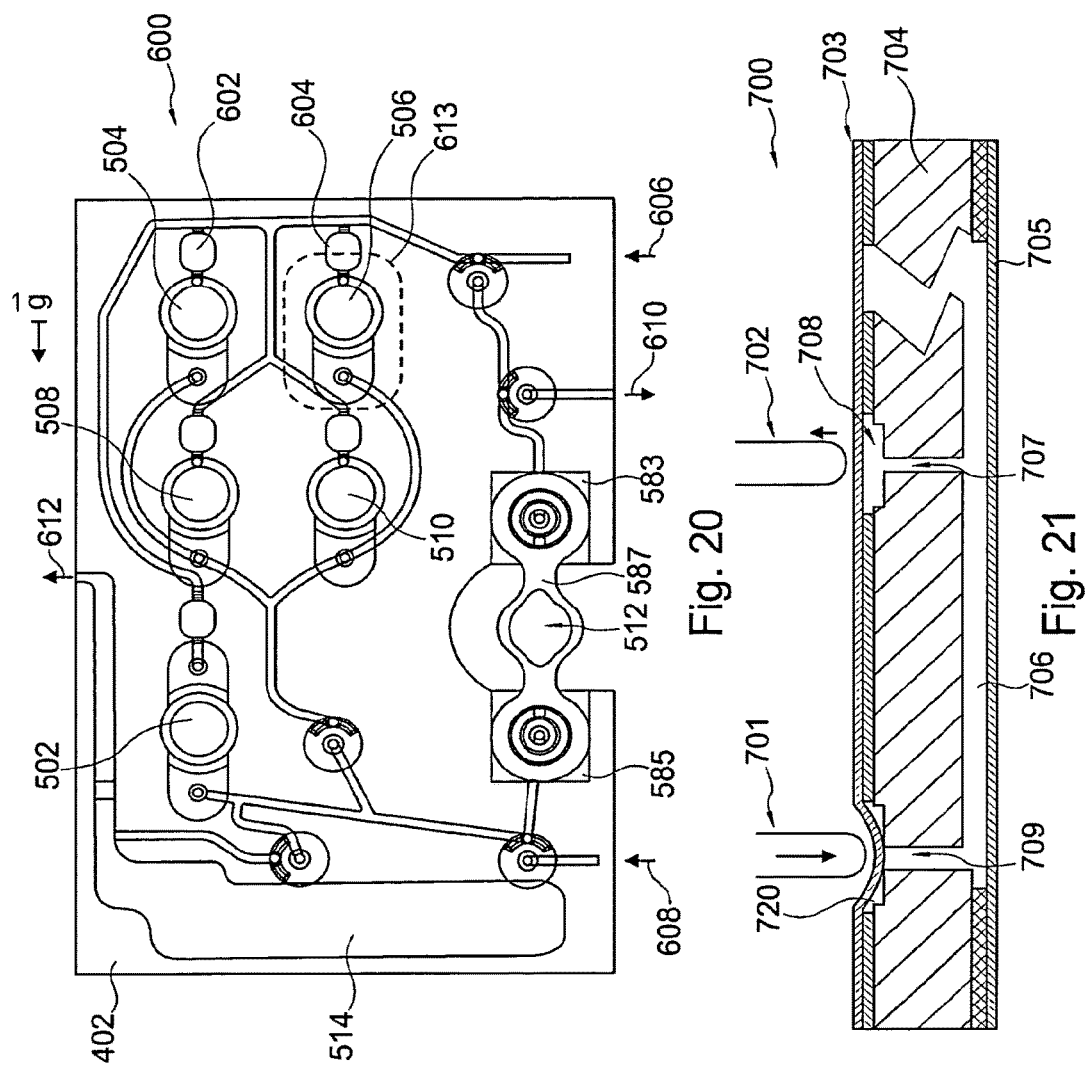
FIG. 20 illustrates a plan view of a device.
FIG. 21 illustrates a cross-sectional view of a device.

The embodiment of FIG. 20 is similar to the embodiments of FIG. 18, 19, so that corresponding components are denoted with the same reference numerals. For the sake of simplicity and clarity, the channels and fluid ports are not denoted with reference numerals in FIG. 20. For corresponding explanation, reference is made to FIG. 18 and FIG. 19.

FIG. 20 shows a window portion 602 related to the well 504 and a window portion 604 related to the well 506 to enable for a meniscus detection and therefore an overflow detection as a basis for determining control signals for controlling actuators acting on the wells 504, 506 and acting on the various fluid communication ports.

The direction of the gravity vector $\vec{g}$ is indicated to show in which position the device 600 can be operated in some embodiments. In these embodiments, the operation of the device 600 is based on a combination of the gravitational force and liquid transportation forces provided via a pressure air connection 606, and a water supply connection 608. Furthermore, a vent connection 610 and a vent connection 612 are provided for venting the corresponding fluidic structures.

FIG. 20 schematically shows a portion 613 which can be, as an alternative to the integral solution of FIG. 20, be provided as a separate module which can be combined with other modules to form a user-defined device in which the various modules are assembled together.

In the following, referring to FIG. 21, a device 700 according to another exemplary embodiment will be explained.

The device 700 includes a rigid substrate 704 in which a first through hole 709 and a second through hole 707 are formed. On a first main surface of the substrate 704, a first well 720 and a second well 708 are formed. On an opposing main surface of the substrate 704, a channel 706 is formed. The channel 706 is in fluid communication with the wells 720, 708 via the through holes 709, 707, respectively.

On an upper surface of the rigid substrate 704, a first flexible cover element 708 is formed and adhered to the rigid substrate 704. On a lower surface of the substrate 704, a second cover element 705 is formed and laminated to the rigid substrate 704.

As can further be taken from FIG. 21, a first actuator member 701 and a second actuator member 702 are provided, the first actuator member 701 being adapted for pressing on a first portion of the cover element 720 to selectively close the through hole channel 709 or the entire well 720. In a corresponding manner, the second actuator element 702 can selectively open or close the well 708 and/or the through hole 707. Thus, the flow of a fluid through channel 706 into one or both of the wells 720 or 708 can be controlled.

Figure 22:
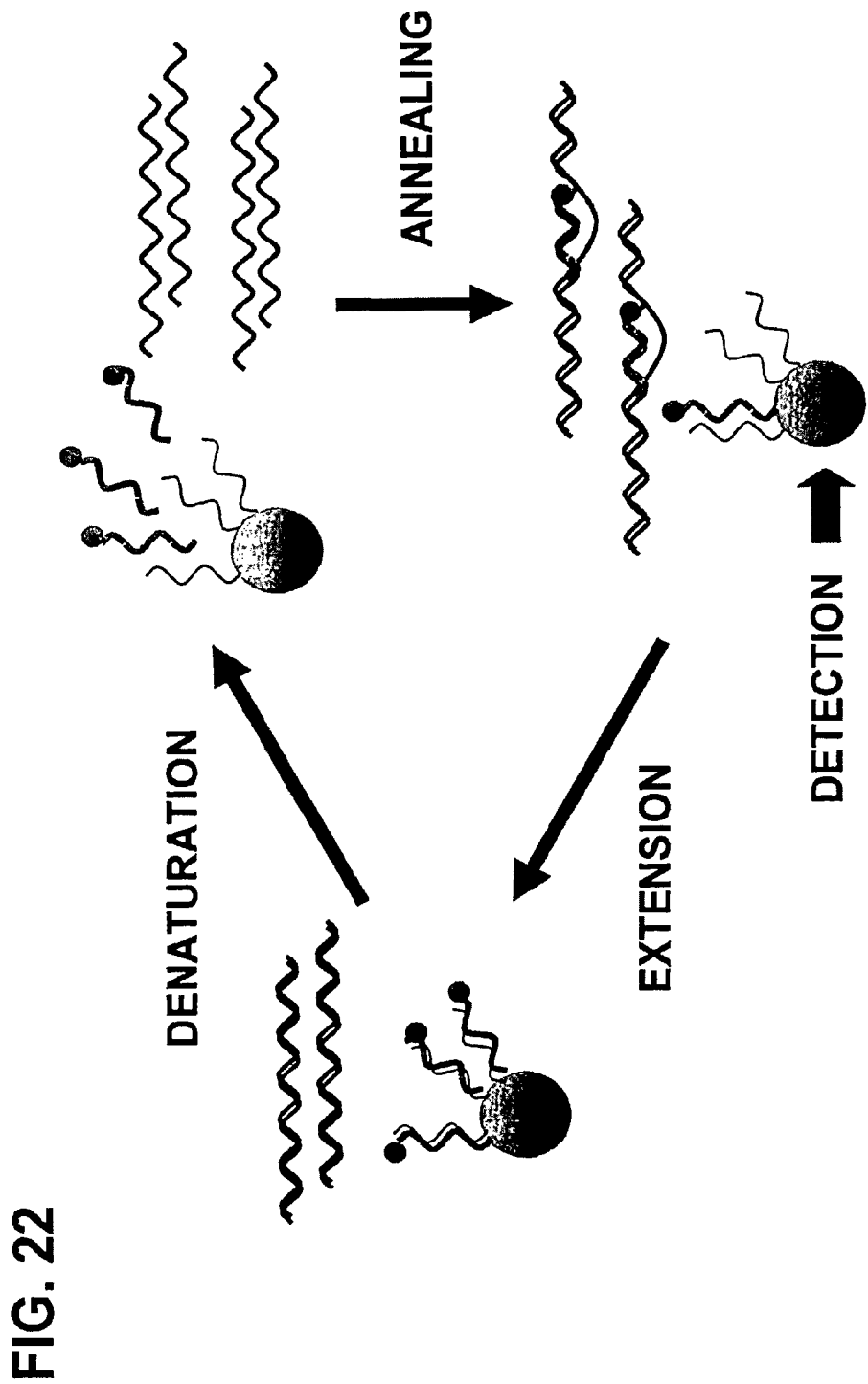
FIG. 22 schematically illustrates a competitive method for the detection of polynucleotides.

FIG. 22 represents a schematic illustration of an exemplary competitive assay according to the present invention. A labelled nucleic acid reporter molecule (shown as a grey sinuous line) is attached via a nucleic acid capture molecule (shown as a black sinuous line) on a binding member (here exemplified as a bead). The target nucleic acid to be detected is present in the sample in double-stranded form (the two strands are shown as light grey/black sinuous lines). Subjecting the sample to a denaturation step (of a cyclic amplification reaction) allows the strands of the target nucleic acid to dissociate and the reporter molecule to be released from the binding member. During the subsequent annealing step, a subset of the amount of reporter molecule is allowed to form complexes with at least a subset of the amount of the target nucleic acid, wherein the forming of target nucleic acid/reporter molecule complexes inhibits the capability of the reporter molecule of being captured on the binding member due to a competition of the capture molecule and the nucleic acid target for binding the reporter molecule. The remaining subset of the amount of reporter compound not in complex with a target nucleic acid is allowed to be re-captured on the binding member. At this stage, a value indicative of the presence and/or amount of reporter compound captured on the binding member, and based thereon a value indicative of the presence and/or amount of the target nucleic acid, is determined by detecting a signal generated by the label included in the receptor molecule. Consecutively or concomitantly to the annealing step, the extension step of the amplification reaction is performed. Then, the sample can be subjected to another amplification cycle.

Figure 23:
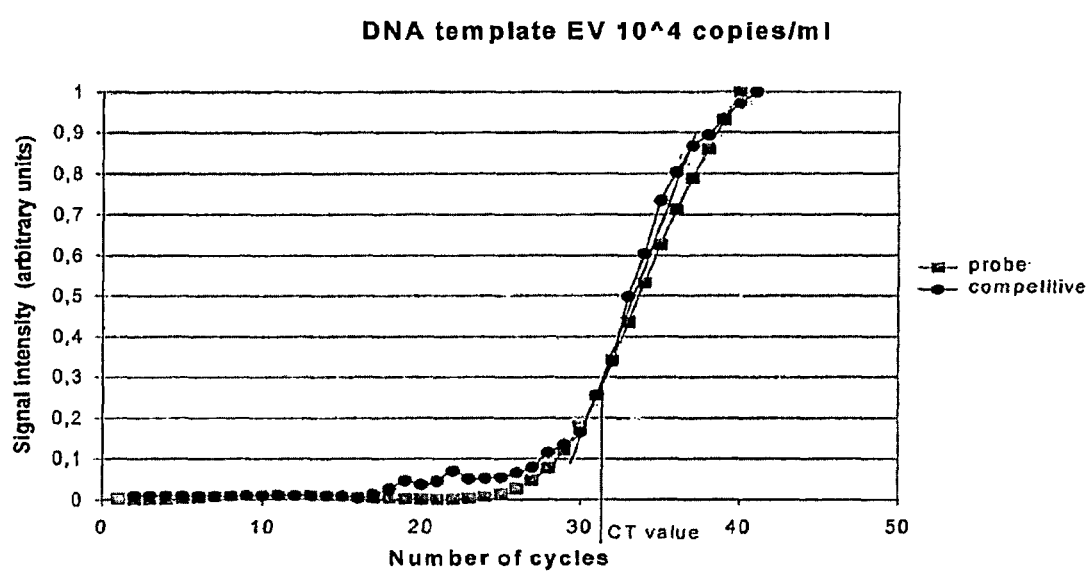
FIG. 23 shows the results of a competitive assay for determining the amount of human poliovirus 1 DNA in a sample.

FIG. 23 shows the results of an exemplary competitive assay according to the present invention for determining the amount of human poliovirus 1 DNA (designated "EV" for "enterovirus DNA") in a sample in comparison to a standard Taq-man assays performed with the same target. Two samples, each containing $10^4$ DNA copies were analyzed in parallel: the first sample (label "probe" in the diagram) was subjected to PCR amplification using a Rotor-Gene 6000 real-time rotary PCR analyzer (Corbett Life Sciences, Sydney, Australia) according to the manufactures instructions. The PCR primer employed resulted in the amplification of a 150 bp DNA fragment. Detection of the fragment was accomplished by means of a so-called Taqman® probe including a 6-carboxy-fluorescein (FAM) label at its 5' terminus and a 6-carboxytetramethylrhodamine-succinimidylester (TAMRA) label at its 3' terminus, respectively (Invitrogen Corporation, Carlsbad, Calif., USA). In total, 50 PCR cycles were performed. The second sample ("competitive assay") additionally included a reporter molecule having the same nucleotide sequence as the Taqman® probe but includes a CY3 carbocyanine label (Invitrogen Corporation, Carlsbad, Calif., USA) at its 3' terminus instead of FAM/TAMRA labels and was amplified using a device according to one embodiment of the present invention. The fluorescence signals obtained detected during amplification are shown in the diagram.

FIG. 24 illustrates the principle and shows the results of an exemplary array-based competitive assay according to the present invention for determining the amount of a HIV gag/env PCR product in a sample. FIG. 24A schematically illustrates the principle of the assay (cf. also FIG. 22). Initially, no amplified PCR product, i.e., target nucleic acid is present. Labelled fluorescent nucleic acid reporter molecules are bound to reporter-specific probes captured on the substrate of an array. If no PCR product is produced, the amount of reporter molecule hybridizing to the reporter-specific probes remains constant after each cycle of the amplification reaction and thus the fluorescence signal determined remains constant as well. If a PCR product is synthesized, the amount of reporter molecule hybridizing to the reporter-specific probes decreases after each PCR cycle and, as a result, the fluorescence signal determined decreases accordingly. FIG. 24B shows the results of an array-based competitive assay for determining the amount of a 151 bp HIV 1 gag/env PCR product. Different amounts of fragment (corresponding to $10^4$-$10^6$ copies) along with a reporter molecule ("anti_cdso29_5'CY3") including at its 5' terminus a CY3 carbocyanine label (Invitrogen Corporation, Carlsbad, Calif., USA) were subjected to 36 cycles of PCR amplification. Two different types of probe molecules—a non-specific one ("ara_54986_NH2") and a reporter-specific one ("cdso29_NH2")—were captured on an array substrate in an arrangement as shown in FIG. 25A and disposed within the reaction chamber of the assay device employed. The CT values ("threshold"; i.e., a measure for the onset of the exponential amplification phase, where the increase in fluorescence and thus DNA amount occurs in a linear manner) were determined using the Iconoclust software (Clondiag Chip Technologies GmbH, Jena, Germany) and plotted versus the respective DNA concentrations employed to generate a calibration curve (FIG. 24C). In all samples employing the receptor-specific probe a progressive decrease in fluorescence intensity was observed as the number of PCR cycles increased. In contrast, in the sample using the non-specific probe no fluorescence was observed (FIG. 24B).

FIG. 25 depicts the array employed in the assay shown in FIG. 24 at different stages of the PCR amplification. The arrangement of the different spots on the array substrate is schematically illustrated in FIG. 25A. The black circles denote spots (four parallel samples), where the specific probe (cf. FIG. 24) was used for capturing the reporter molecules, whereas the white circles refer to spots (four parallel samples), where the non-specific probe was used for capturing the reporter molecules. The grey circles represent positive controls, where the fluorescent label was spotted on the array substrate. FIG. 25B shows photographs of the array (corresponding to the $10^5$ DNA copies-samples in FIG. 24B) that were taken after amplification cycles 1, 12, 18, and 21, respectively. In the samples captured on the array via the specific probe molecules a decrease in fluorescence signal intensity can be observed during the course of the PCR amplification.

Figure 26A:
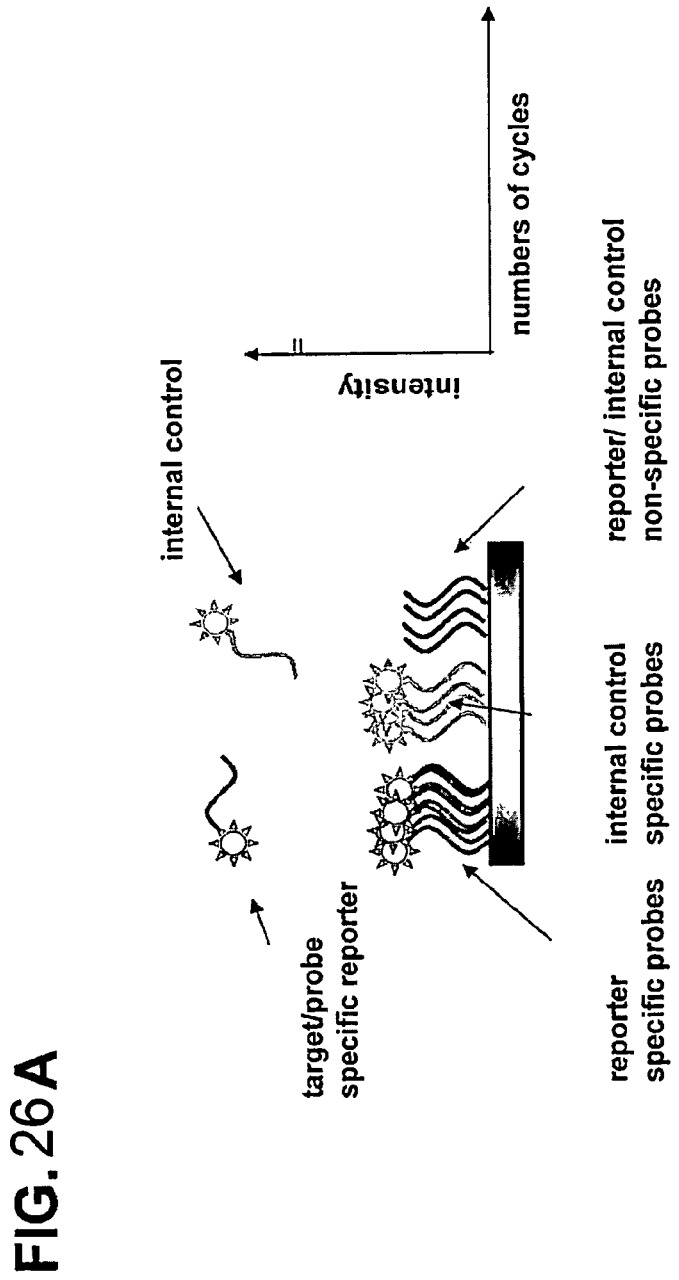
FIGS. 26A-D schematically illustrates the competitive method for the detection of polynucleotides.
Figure 26:
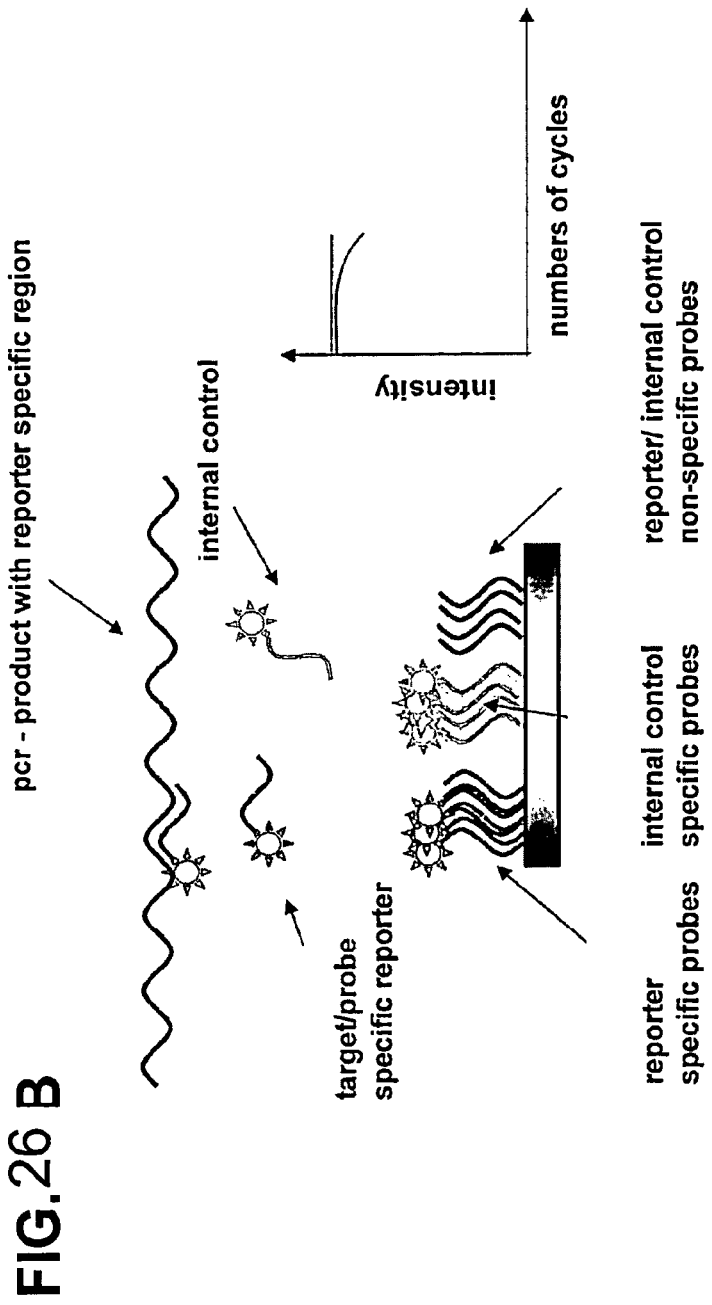
Figure 26:
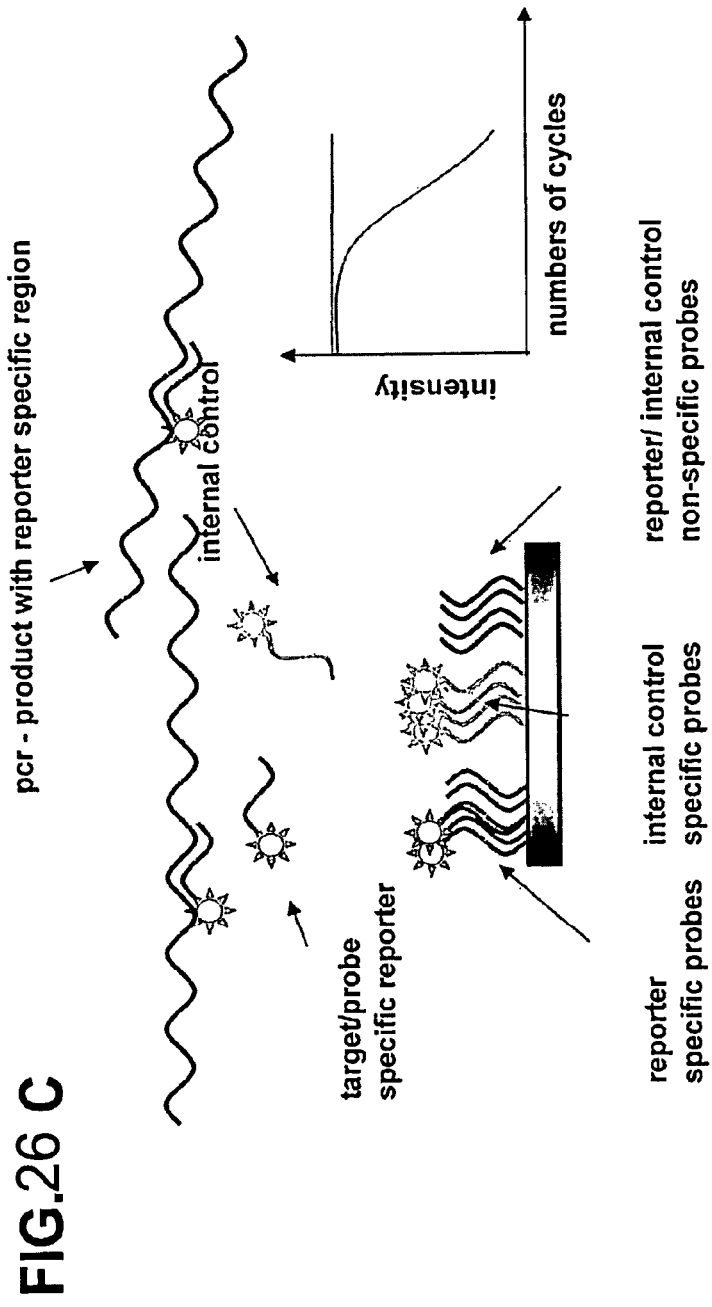
Figure 26:
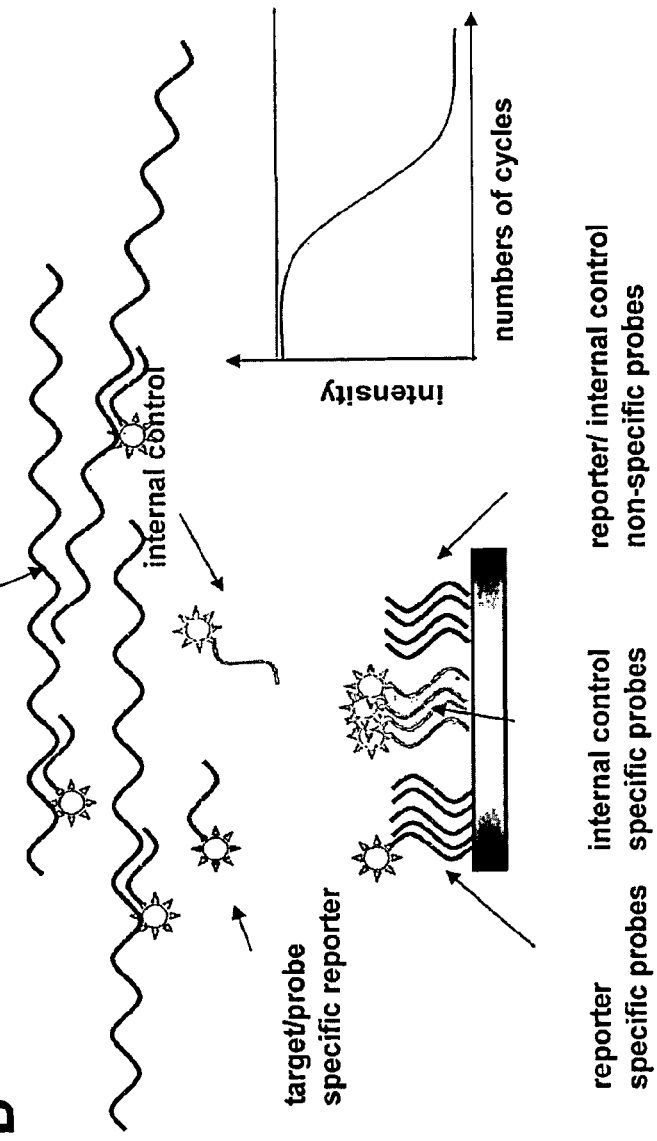

FIGS. 26A-D represent a schematic illustration of an exemplary embodiment of the competitive method for the detection of polynucleotides according to the present invention. As shown in FIG. 26A, initially, no amplified PCR product, i.e., target nucleic, acid is present. Labelled nucleic acid reporter molecules (shown as a black sinuous line and denoted as target/probe specific reporter) are bound to reporter-specific probes captured on the substrate of an array. The signal corresponds to that of labelled internal control molecules (shown as light grey sinuous line) which are bound to internal control-specific probes captured on the substrate of an array. As shown in FIG. 26B, if the PCR enters into the early exponential phase the reporter molecules not only bind to reporter-specific probes captured on the substrate but also bind to the reporter-specific region of the PCR product. Thus, if a PCR product is synthesized, the amount of reporter molecule hybridizing to the reporter-specific probes captured on the substrate decreases and, as a result, the signal determined decreases accordingly. The signal decreases significantly when the PCR is in the exponential phase (see FIG. 26C). The signal on the reporter-specific probes captured on the substrate remains low when the PCR reaches the plateau phase (see FIG. 26D).

Figures 27A, 27B:
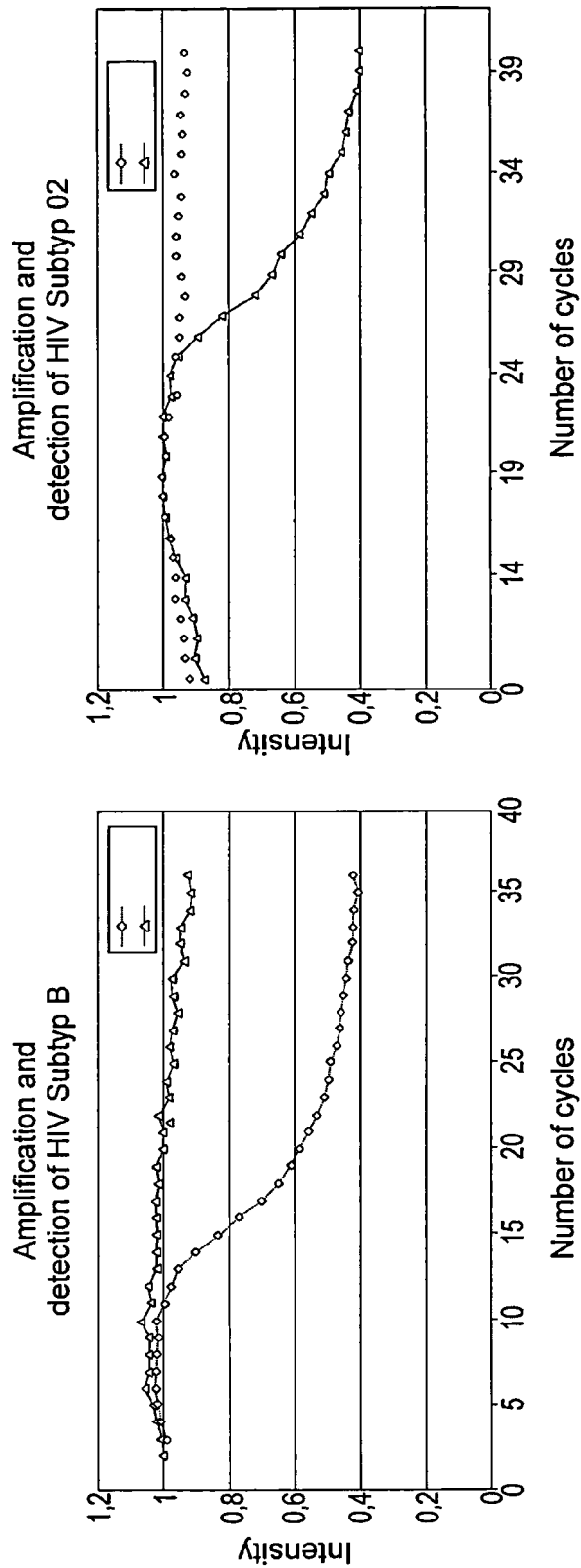
FIGS. 27A-B shows the results of a competitive assay for determining the amount of HIV subtype Band HIV subtype $O_2$ in a sample.

FIGS. 27A-B shows the results of an exemplary embodiment of the competitive assay according to the present invention for determining the amount of HIV subtype B and HIV subtype O2 in a sample. In the experiment underlying FIG. 27A, only HIV Subtype B was present in the sample. It can be seen that the signal corresponding to a labelled nucleic acid reporter molecule specific for HIV subtype $O_2$ (HIV sub $O_2$) remains constant whereas the signal corresponding to a labelled nucleic acid reporter molecule specific for HIV subtype B (HIV sub B) decreases significantly after about 13 cycles of the PCR (cf. FIGS. 26A-D). In the experiment underlying FIG. 27B, only HIV Subtype O2 was present in the sample. It can be seen that the signal corresponding to a labelled nucleic acid reporter molecule specific for HIV subtype B (HIV sub B) remains constant whereas the signal corresponding to a labelled nucleic acid reporter molecule specific for HIV subtype $O_2$ (HIV sub $O_2$) decreases significantly after about 25 cycles of the PCR (cf. FIGS. 26A-D).

Figure 28:
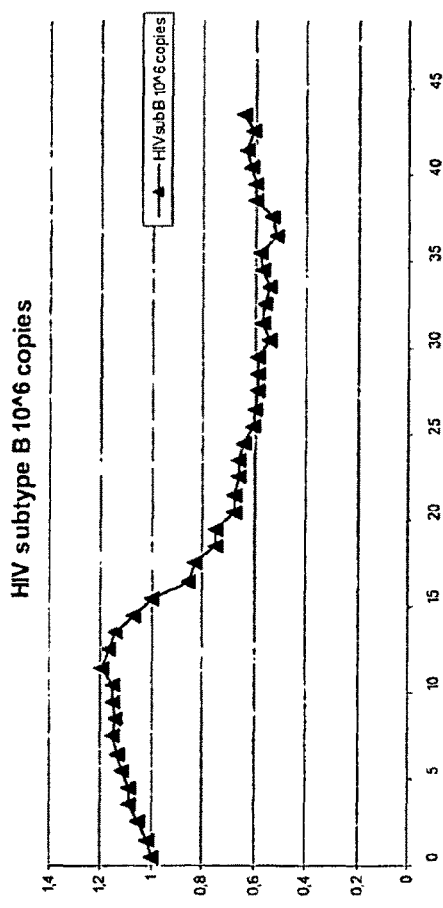
FIG. 28A-28B shows the results of a competitive assay for determining different amounts of HIV subtype B in a sample.
Figure 28B:
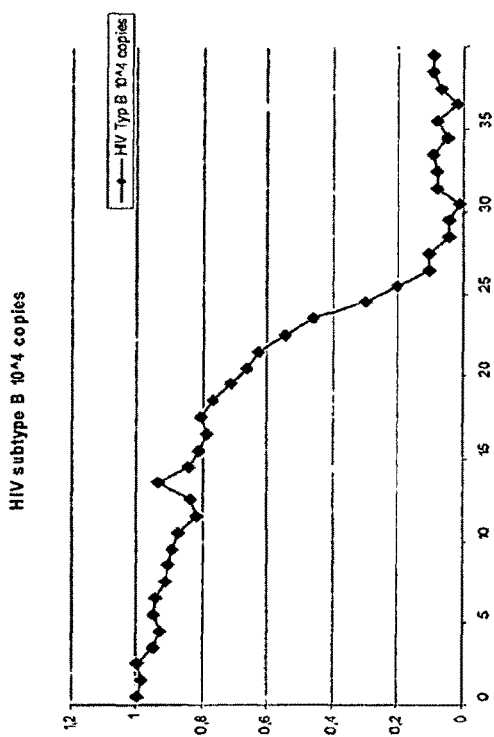

FIGS. 28A-B shows the results of an exemplary embodiment of the competitive assay according to the present invention for determining different amounts of HIV subtype B in a sample. If $10^6$ copies of HIV are present in the sample the signal corresponding to a labelled nucleic acid reporter molecule specific for HIV subtype B (HIV sub B) decreases significantly after about 13 cycles of the PCR (see FIG. 28A). If only $10^4$ copies of HIV are present in the sample the signal corresponding to a labelled nucleic acid reporter molecule specific for HIV subtype B (HIV sub B) decreases significantly after about 19 cycles of the PCR (see FIG. 28B). It is apparent from FIGS. 28A-B that the amount of PCR cycles required before a decrease in the signal is detectable allows conclusions as to the amount of target nucleic acid present in the sample to be analyzed.

The invention is further described by the following examples, which are solely for the purpose of illustrating specific embodiments of this invention, and are not to be construed as limiting the scope of the invention in any way.

EXAMPLES

Example 1

Competitive Assay for Determining Human Poliovirus 1 DNA

The principle of the competitive assay performed is schematically shown in FIG. 22. DNA of human poliovirus 1 isolate TCDC0I-861 (GenBank accession number AF538843) cloned into a suitable expression vector (pCR®2.1-TOPO®, Clontech, Inc. Palo Alto, Calif., USA) was used as a DNA template (herein also designated "EV" (enterovirus) DNA).

Two samples, each containing $10^4$ DNA copies were analyzed in parallel: the first sample was subjected to PCR amplification using a Rotor-Gene 6000 real-time rotary PCR analyzer (Corbett Life Sciences, Sydney, Australia) according to the manufactures instructions.

The second sample additionally included a reporter molecule having the same nucleotide sequence as the Taqman® probe but includes a CY3 carbocyaninc label (Invitrogen Corporation, Carlsbad, Calif., USA) at its 3' terminus instead of FAM/TAMRA labels and was amplified using directly in a reaction chamber of an assay device, in which the array was disposed on the heatable base surface.

The following PCR primers were used:

```
forward PCR primer:
                                        (SEQ ID NO: 1)
pr_for_EV_02:
5'-CAAACCAGTGATTGGCCTGTCGTAACG-3'
(corresponding to the nucleotide positions 492-
18 of AF538843)

reverse PCR primer:
                                        (SEQ ID NO: 2)
5'-TTCACCGGATGGCCAATCCAATTCG-3'
(corresponding to the nucleotide positions 617-
641 of AF538843)
```

Thus, PCR resulted in the amplification of a 150 bp DNA fragment. PCR samples contained 200 nM (final concentration) each of the PCR primers as well as the EnzymMix® and the reaction buffer of the Ultrasense RT-PCR Kit (Invitrogen Corporation, Carlsbad, Calif., USA) according to manufactures instructions.

Furthermore, for detecting the amplified PCR fragment using the Rotor-Gene 6000 real-time rotary PCR analyzer the according PCR sample contained 100 nM (final concentration) of a dual-labelled so-called Taqman® probe including a 6-carboxy-fluorescein (FAM) label at its 5' terminus (i.e., the fluorophor) and a 6-carboxy-tetramethyl-rhodamine-succinimidylester (TAMRA) label at its 3' terminus (i.e., the quencher), respectively (both labels were purchased from Invitrogen Corporation, Carlsbad, Calif., USA). The probe has the following sequence:

```
HP_EV2_001:
                                        (SEQ ID NO: 3)
FAM-5'-ACCGACTACTTTGGGTGTCCGTGTTT-3'-TAMRA
(corresponding to the nucleotide positions 536-
561 of AF538843)
```

For performing the competitive analysis, the PCR sample further contained 20 nM (final concentration) of a reporter molecule having the same sequence but a different label as the Taqman® probe, namely a CY3 carbocyanine label at its 3' terminus (Invitrogen Corporation, Carlsbad, Calif., USA):

```
EV2_02CY3:
                                        (SEQ ID NO: 3)
5'-ACCGACTACTTTGGGTGTCCGTGTTT-3'-CY3
(corresponding to the nucleotide positions 536-
561 of AF538843)
```

Real-time PCR was performed according to the following temperature profile: 2 minutes at 94° C., and subsequently 50 cycles of 5 seconds at 94° C., 30 seconds at 62° C., and 30 seconds at 72° C.

During PCR fluorescence signals for both reactions are shown in FIG. 23.

Example 2

Array-Based Competitive Assay for Determining HIV1 Gag/Env DNA

The principle of the competitive assay performed is schematically shown in FIG. 24A. DNA of a synthetic HIV1 gag/env fusion construct (EMBL accession number A06258) cloned into the EcoRI endonuclease restriction site of the expression vector pCR®2.1-TOPO® (Clontech, Inc. Palo Alto, Calif., USA) was used as a DNA template.

Furthermore, the following PCR primers were used:

```
forward PCR primer:
                                        (SEQ ID NO: 4)
cdia:
5'-TGAAGGGTACTAGTAGTTCCTGCTATGTC-3'
(corresponding to the nucleotide positions 214-
232 of A06258)

reverse PCR primer:
                                        (SEQ ID NO: 5)
cdis:
5'-ATCAAGCAGCCATGCAAATGTT-3'
(corresponding to the nucleotide positions 384-
405 of A06258)
```

Thus, PCR resulted in the amplification of a 151 by DNA fragment having the following sequence:

```
                                        (SEQ ID NO: 6)
5'-ATC AAG CAG CCA TGC AAA TGT TAA AAG AGA CCA TCA

ATG AGG AAG CTG CAG AAT GGG ATA GAT TGC ATC CAG

TCC ATG GAG GGC CTA TTG CAC CAG GCC AGA TGA GAG

AAC CAA GGG GAA GTG ACA TAG CAG GAA CTA CTA GTA

CCC TTC A-3'.
```

PCR was performed directly in the reaction chamber of the assay device, in which the array was disposed on the heatable base surface. PCR samples contained 200 nM (final concentration) each of the PCR primers as well as the EnzymMix® and the reaction buffer of the Ultrasense RT-PCR Kit (Invitrogen Corporation, Carlsbad, Calif., USA). For generating a calibration curve, different amounts of DNA template (in 1 µl) were used corresponding to 0, $10^4$, $10^5$, and $10^6$ DNA copies (each performed in quadruplicate).

For performing the competitive analysis, the PCR sample further contained 10 nM (final concentration) of a reporter molecule having a CY3 carbocyanine label at its 5' terminus (Invitrogen Corporation, Carlsbad, Calif., USA):

```
anti_cdso29_5' CY3:
                                        (SEQ ID NO: 7)
CY3-5'-TCCCATTCTGCAGCTTCCTCATTGATGGT-3'
(complementary to the cdso29 NH2 probe molecule
described below)
```

PCR was performed according to the following temperature profile: 30 seconds at 95° C., and subsequently 36 cycles of 5 seconds at 95° C., 30 seconds at 50° C., and 30 seconds at 72° C.

The interaction of the reporter molecule with the two types of probes was determined in each cycle at the end of the annealing step using an optical detection system positioned opposite to the top surface of the assay device and the Iconoclust software package (Clondiag Chip Technologies GmbH, Jena, Germany). The exposure time during data acquisition was 2.5 s.

Two different types of probe molecules were captured on the array substrate in an arrangement as shown in FIG. 25A. Fluorescent labels alone were used as positive controls. The following probes were employed:

```
non-specific probe:
                                        (SEQ ID NO: 8)
ara_54986_NH2:
5'-ACCAGCTTTGAACCCAACAC-3' receptor-specific probe:
                                        (SEQ ID NO: 9)
cdso29_NH2:
5'-ACCATCAATGAGGAAGCTGCAGAATGGGA-3'
```

The CT values ("thresholds"), as a measure for the onset of the exponential amplification phase, where the increase in fluorescence and thus DNA amount occurs in a linear manner, were determined using the Iconoclust software (Clondiag Chip Technologies GmbH, Jena, Germany) and plotted versus the respective DNA concentrations employed to generate a calibration curve (FIG. 24C). The mean CT values determined were as follows: 22.0 in the $10^4$ DNA copies-samples; 18.5 in the $10^5$ DNA copies-samples; and 15.0 in the $10^6$ DNA copies-samples.

In all samples employing the receptor-specific probe a progressive decrease in fluorescence intensity was observed as the number of PCR cycles increased. In contrast, in the sample using the non-specific probe no fluorescence was observed (FIG. 24B).

The arrangement of the different spots on the array substrate is schematically illustrated in FIG. 25A. The black circles denote spots (four parallel samples), where the specific probe (cf. FIG. 24) was used for capturing the reporter molecules, whereas the white circles refer to spots (four parallel samples), where the non-specific probe was used for capturing the reporter molecules. The grey circles represent positive controls, where the fluorescent label was spotted on the array substrate.

FIG. 25B shows photographs of the array (corresponding to the $10^5$ DNA copies-samples in FIG. 24B) that taken after amplification cycles 1, 12, 18, and 21, respectively. In the samples captured on the array via the specific probe molecules a progressive decrease in fluorescence signal intensity can be observed during the course of the PCR amplification that, in turn, corresponds to a concomitant increase of the amount of PCR product amplified that can be quantified by comparison with a corresponding calibration curve.

It should be noted that the term "including" does not exclude other elements or features and the "a" or "an" does not exclude a plurality. Also elements described in association with different embodiments can be combined.

It should also be noted that reference signs in the claims shall not be construed as limiting the scope of the claims.

The invention claimed is:

1. A method, comprising:
   (a) providing: an amount of a reporter compound; a first binding member being configured to bind an anchor group of a capture molecule; a second binding member capable of capturing the reporter compound; an amount of a target nucleic acid capable of forming complexes with the reporter compound, the forming of complexes with the reporter compound inhibiting capturing of the reporter compound by the second binding member; and an amount of capture molecules wherein each capture molecule comprises a binding portion specific to a region of the target nucleic acid and an anchor group;
   (b) forming complexes each comprising the target nucleic acid and the capture molecule;
   (c) contacting the complexes with the first binding member to bind the complexes to the first binding member;
   (d) releasing at least a subset of the amount of target nucleic acid from the first binding member;
   (e) forming complexes of a subset of the amount of reporter compound with at least a subset of the amount of target nucleic acid;
   (f) capturing a remaining subset of the amount of reporter compound not in complex with the target nucleic acid on the second binding member:
   (g) determining a value indicative of the amount of reporter compound captured on the second binding member; and
   (h) determining a value indicative of the amount of target nucleic acid based on the value indicative of the amount of reporter compound captured on the second binding member; and
   (i) wherein the value indicative of the amount of reporter compound captured on the second binding member is determined before forming complexes of the subset of the amount of reporter compound with at least the subset of the amount of target nucleic acid.

2. The method of claim 1, further comprising determining a value indicative of the amount of target nucleic acid based on the value indicative of the amount of reporter compound captured on the binding member.

3. The method of claim 2, wherein the value indicative of the amount of target nucleic acid is determined based on a calibration curve correlating the value indicative of the presence and/or amount of reporter compound with the value indicative of the presence and/or amount of target nucleic acid.

4. The method of claim 1, further comprising releasing the remaining subset of the amount of reporter compound from the binding member after the steps of forming complexes of a subset of the amount of reporter compound with at least a subset of the amount of target nucleic acid, capturing a remaining subset of the amount of reporter compound not in complex with a target nucleic acid on the binding member, and determining the value indicative of the amount of reporter compound captured on the binding member.

5. The method of claim 4, further comprising performing the steps of releasing, forming complexes, capturing, and determining a number N additional times, where N is an integer greater than or equal to 1.

6. The method of claim 4, further comprising performing the steps of releasing, forming complexes, capturing, and determining a number N additional times, wherein N ≥5 .

7. The method of claim 4, further comprising performing the steps of releasing, forming complexes, capturing, and determining a number N additional times, wherein N ≥10 .

8. The method of claim 4, further comprising performing the steps of releasing, forming complexes, capturing, and determining a number N additional times, wherein N ≥20 .

9. The method of claim 1, further comprising, prior to the step of forming complexes: capturing at least a subset of the amount of reporter compound on the binding member; determining a value indicative of the amount of reporter compound captured on the binding member; and releasing captured reporter compounds from the binding member.

10. The method of claim 1, wherein the step of forming complexes of a subset of the amount of reporter compound with at least a subset of the amount of target nucleic acid and the step of capturing a remaining subset of the amount of reporter compound not in complex with a target nucleic acid on the binding member are performed concomitantly.

11. The method of claim 1, wherein the value indicative of the amount of reporter compound captured on the binding member is determined 1seconds to 120 seconds after initiating the steps of forming complexes of a subset of the amount of reporter compound with at least a subset of the amount of target nucleic acid and of capturing a remaining subset of the amount of reporter compound not in complex with a target nucleic acid on the binding member.

12. The method of claim 1, wherein a reporter compound comprises one or more detectable labels.

13. The method of claim 12, wherein the one or more detectable labels are fluorescent labels.

14. The method of claim 12, wherein the label is a compound that includes a chemical substance that generates a detectable signal in a physical reaction.

15. The method of claim 12, wherein the label is an enzyme that generates a detectable signal in an enzymatic reaction.

16. The method of claim 1, wherein the reporter compounds are oligonucleotides.

17. The method of claim 1, wherein forming a composition of matter comprises forming a composition of matter comprising: an amount of a first reporter compound, an amount of a first target nucleic acid capable of forming complexes with the first reporter compound, the forming of complexes with the first reporter compound inhibiting capturing of the first reporter compound by the binding member, an amount of a second reporter compound, and an amount of a second target nucleic acid capable of forming complexes with the second reporter compound, the forming of complexes with the second reporter compound inhibiting capturing of the second reporter compound by the binding member.

18. The method of claim 1, wherein the binding member comprises one or more different capture molecules being capable of capturing a reporter compound on the binding member.

19. The method of claim 18, wherein the capture molecules are oligonucleotides.

20. The method of claim 18, wherein different capture molecules are arranged on different locations with respect to the binding member.

21. The method of claim 18, wherein the reporter compound is captured on the binding member by forming complexes with the capture molecules.

22. The method of claim 1, wherein determining the value indicative of the amount of reporter compound captured on the binding member comprises time-dependent monitoring of the indicative value.

23. The method of claim 1, further comprising subjecting the target nucleic acid to thermal cyclic amplification.

24. The method of claim 23, wherein the thermal cyclic amplification comprises at least 10 cycles.

25. The method of claim 23, wherein the thermal cyclic amplification comprises at least 20cycles.

26. The method of claim 23 wherein the thermal amplification is a PCR.

27. The method of claim 26, wherein performing the PCR comprises using a polymerase having exonuclease activity.

* * * * *

SEQUENCE LISTING

```
<160> NUMBER OF SEQ ID NOS: 9

<210> SEQ ID NO 1
<211> LENGTH: 27
<212> TYPE: DNA
<213> ORGANISM: artificial
<220> FEATURE:
```

<223> OTHER INFORMATION: Primer

<400> SEQUENCE: 1
caaaccagtg attggcctgt cgtaacg                                27

<210> SEQ ID NO 2
<211> LENGTH: 25
<212> TYPE: DNA
<213> ORGANISM: artificial
<220> FEATURE:
<223> OTHER INFORMATION: Primer

<400> SEQUENCE: 2
ttcaccggat ggccaatcca attcg                                  25

<210> SEQ ID NO 3
<211> LENGTH: 26
<212> TYPE: DNA
<213> ORGANISM: artificial
<220> FEATURE:
<223> OTHER INFORMATION: Probe

<400> SEQUENCE: 3
accgactact ttgggtgtcc gtgttt                                 26

<210> SEQ ID NO 4
<211> LENGTH: 29
<212> TYPE: DNA
<213> ORGANISM: artificial
<220> FEATURE:
<223> OTHER INFORMATION: Primer

<400> SEQUENCE: 4
tgaagggtac tagtagttcc tgctatgtc                              29

<210> SEQ ID NO 5
<211> LENGTH: 22
<212> TYPE: DNA
<213> ORGANISM: artificial
<220> FEATURE:
<223> OTHER INFORMATION: Primer

<400> SEQUENCE: 5
atcaagcagc catgcaaatg tt                                     22

<210> SEQ ID NO 6
<211> LENGTH: 151
<212> TYPE: DNA
<213> ORGANISM: artificial
<220> FEATURE:
<223> OTHER INFORMATION: Synthetic HIV1 gag/env fusion fragment

<400> SEQUENCE: 6
atcaagcagc catgcaaatg ttaaaagaga ccatcaatga ggaagctgca gaatgggata    60
gattgcatcc agtccatgga gggcctattg caccaggcca gatgagagaa ccaagggaa   120 gtgacatagc aggaactact agtacccttc a                                 151

<210> SEQ ID NO 7
<211> LENGTH: 29
<212> TYPE: DNA
<213> ORGANISM: artificial
<220> FEATURE:
<223> OTHER INFORMATION: Reporter molecule

<400> SEQUENCE: 7

```
tcccattctg cagcttcctc attgatggt                                      29

<210> SEQ ID NO 8
<211> LENGTH: 20
<212> TYPE: DNA
<213> ORGANISM: artificial
<220> FEATURE:
<223> OTHER INFORMATION: Probe

<400> SEQUENCE: 8
accagctttg aacccaacac                                                20

<210> SEQ ID NO 9
<211> LENGTH: 29
<212> TYPE: DNA
<213> ORGANISM: artificial
<220> FEATURE:
<223> OTHER INFORMATION: Probe

<400> SEQUENCE: 9
accatcaatg aggaagctgc agaatggga                                      29
```